(12) United States Patent
Ayre et al.

(10) Patent No.: US 6,866,625 B1
(45) Date of Patent: Mar. 15, 2005

(54) ROTARY BLOOD PUMP AND CONTROL SYSTEM THEREFOR

(75) Inventors: Peter Joseph Ayre, Neutral Bay (AU); Geoffrey Douglas Tansley, Mi-Colah (AU); Peter Andrew Watterson, West Ryde (AU); John Campbell Woodard, Thornleigh (AU)

(73) Assignees: Ventrassist Pty Ltd, Chatswood (AU); University of Technology, Sydney (AU)

( * ) Notice: Subject to any disclaimer, the term of this patent is extended or adjusted under 35 U.S.C. 154(b) by 0 days.

(21) Appl. No.: 09/980,682

(22) PCT Filed: Apr. 20, 2000

(86) PCT No.: PCT/AU00/00355
§ 371 (c)(1),
(2), (4) Date: Aug. 15, 2002

(87) PCT Pub. No.: WO00/64509
PCT Pub. Date: Nov. 2, 2000

(30) Foreign Application Priority Data

Apr. 23, 1999 (AU) .............................................. PP9959

(51) Int. Cl.$^7$ ............................. A61M 1/10; A61M 1/12
(52) U.S. Cl. ...................................... 600/16; 415/182.1
(58) Field of Search ........................................... 600/16

(56) References Cited

U.S. PATENT DOCUMENTS

| | | | |
|---|---|---|---|
| 3,957,389 A | 5/1976 | Rafferty et al. ................. 415/1 |
| 4,382,199 A | 5/1983 | Isaacson ...................... 310/87 |
| 4,625,712 A | 12/1986 | Wampler ..................... 600/16 |
| 4,688,998 A | 8/1987 | Olsen et al. ................. 417/356 |
| 4,779,614 A | 10/1988 | Moise .......................... 600/16 |
| 4,781,525 A | 11/1988 | Hubbard et al. ............... 415/30 |
| 4,908,012 A | 3/1990 | Moise et al. .................. 600/16 |
| 4,944,748 A | 7/1990 | Bramm et al. .............. 623/3.14 |
| 5,112,200 A | 5/1992 | Isaacson et al. ............. 417/356 |
| 5,211,546 A | 5/1993 | Isaacson et al. ............. 417/356 |
| 5,275,580 A | 1/1994 | Yamazaki ..................... 600/16 |
| 5,324,177 A | 6/1994 | Golding et al. ........... 417/423.1 |
| 5,326,344 A | 7/1994 | Bramm et al. .............. 623/314 |
| 5,350,283 A | 9/1994 | Nakazeki ................. 417/423.7 |
| 5,399,074 A | 3/1995 | Nosé et al. ............... 417/423.1 |
| 5,443,503 A | 8/1995 | Yamane ..................... 623/3.14 |
| 5,470,208 A | 11/1995 | Kletschka ................... 417/356 |
| 5,507,629 A | 4/1996 | Jarvik ...................... 417/423.3 |
| 5,527,159 A | 6/1996 | Bozeman, Jr. et al. ........ 417/45 |
| 5,695,471 A | 12/1997 | Wampler .................... 604/131 |
| 5,725,357 A | 3/1998 | Nakazeki et al. ............. 417/18 |
| 5,840,070 A | 11/1998 | Wampler .................... 604/131 |
| 6,074,180 A * | 6/2000 | Khanwilkar et al. ........ 417/356 |
| 6,080,133 A | 6/2000 | Wampler .................... 604/131 |
| 6,234,772 B1 | 5/2001 | Wampler et al. ....... 417/423.12 |
| 6,234,998 B1 | 5/2001 | Wampler .................... 604/131 |
| 6,302,661 B1 * | 10/2001 | Khanwilkar et al. ..... 417/423.7 |

FOREIGN PATENT DOCUMENTS

| | | | |
|---|---|---|---|
| JP | 8284841 | 10/1996 | ........... F04B/44/06 |
| JP | 08284841 a2 | 10/1996 | ........... F04B/49/06 |
| WO | WO 91/19103 | 12/1991 | ........... A61M/1/10 |
| WO | WO/94/13955 | 6/1994 | ........... F04B/17/00 |
| WO | WO 95/09305 | 4/1995 | ........... F04B/49/06 |
| WO | WO 99/12587 | 3/1999 | ........... A61M/1/12 |

* cited by examiner

Primary Examiner—Carl Layno
(74) Attorney, Agent, or Firm—Knobbe, Martens, Olson & Bear, LLP

(57) ABSTRACT

A pump assembly and estimation and control system therefor, the pump adapted for continuous flow pumping of blood. In a particular form, the pump is a centrifugal pump wherein the impeller is entirely sealed within the pump housing and is exclusively hydrodynamically suspended therein against movement in three translational and two rotational degrees of freedom as the impeller rotates within the fluid urged by electromagnetic means external to the pump cavity. Hydrodynamic suspension is assisted by the impeller having deformities therein such as blades with surfaces tapered from the leading edges to the trailing edges of bottom and top surfaces thereof.

88 Claims, 39 Drawing Sheets

Sketch of the pump cross-section.

Cover coil superimposed by rectangular magnets.

FIG. 5.1. Pump efficiency versus specific speed and pump size (Worthington).

Source: From Stepanoff, A.J. 1993. "Centrifugal and Axial Flow Pumps" (2nd Edition), Krieger Publishing Co. Fl. USA.

HQ curves for the pump and a typical centrifugal pump which exhibits a peak in the HQ curve.

Normal cardiac cycle and decreasing LVP with over pumping.

Pressure Head Estimate for CB #2 RBP 2.8 #6 impeller in 42% HCT

$$z = a+bx+cx^2+dy+ey^2$$

$r^2$ = 0.99280491
a = 77.92812
b = -0.0818024
c = 4.0719548e-05
d = 1.8190222
e = 0.05091337

Pressure Head Estimate for CB#2 RBP 2.8#6 impeller in 42% HCT

$$z = a+bx+cx^{1.5}+dx^2+ey+fy^{0.5}\ln y+gy^{0.5}$$

$r^2 = 0.99107652$
$a = 31.539398$
$b = -0.27608721$
$c = 0.0077887314$
$d = 6.4212762e\text{-}05$
$e = 9.8953353$
$f = 25.194915$
$g = 56.85923$ RBP Flow rate estimate as a function of motor speed and input power.

ROTARY BLOOD PUMP AND CONTROL SYSTEM THEREFOR

This application is a national phase entry in the U.S. of the International Application PCT/AU00/00355 filed Apr. 20, 2000 and claims the priority benefits of U.S. application Ser. No. 09/299,038 filed Apr. 23, 1999 (issued Jun. 26, 2001 as U.S. Pat. No. 6,250,880) and Australian PP 9959 filed Apr. 23, 1999, all of which are incorporated herein by reference in their entireties.

FIELD OF THE INVENTION

This invention relates to rotary pumps adapted, but not exclusively, for use as artificial hearts or ventricular assist devices and, in particular, discloses in preferred forms a seal-less shaft-less pump featuring open or closed (shrouded) impeller blades with at least parts of the impeller used as hydrodynamic thrust bearings and with electromagnetic torque provided by the interaction between magnets embedded in the blades or shroud and a rotating current pattern generated in coils fixed relative to the pump housing.

In addition, a non-contact estimation and control system is described for use in conjunction with the rotary pumps of the invention.

BACKGROUND ART

This invention relates to the art of continuous or pulsatile flow rotary pumps and, in particular, to electrically driven pumps suitable for use although not exclusively as an artificial heart or ventricular assist device. For permanent implantation in a human patient, such pumps should ideally have the following characteristics: no leakage of fluids into or from the bloodstream; parts exposed to minimal or no wear; minimum residence time of blood in pump to avoid thrombosis (clotting); minimum shear stress on blood to avoid blood cell damage such as haemolysis; maximum efficiency to maximise battery duration and minimise blood heating; and absolute reliability.

Several of these characteristics are very difficult to meet in a conventional pump configuration including a seal, i.e. with an impeller mounted on a shaft which penetrates a wall of the pumping cavity, as exemplified by the blood pumps referred to in U.S. Pat. No. 3,957,389 to Rafferty et al., U.S. Pat. No. 4,625,712 to Wampler, and U.S. Pat. No. 5,275,580 to Yamazaki. Two main disadvantages of such pumps are firstly that the seal needed on the shaft may leak, especially after wear, and secondly that the rotor of the motor providing the shaft torque remains to be supported, with mechanical bearings such as ball-bearings precluded due to wear. Some designs, such as U.S. Pat. No. 4,625,712 to Wampler and U.S. Pat. No. 4,908,012 to Moise et al., have overcome these problems simultaneously by combining the seal and the bearing into one hydrodynamic bearing, but in order to prevent long residence times they have had to introduce means to continuously supply a blood-compatible bearing purge fluid via a percutaneous tube.

In seal-less designs, blood is permitted to flow through the gap in the motor, which is usually of the brushless DC type, i.e. comprising a rotor including permanent magnets and a stator in which an electric current pattern is made to rotate synchronously with the rotor. Such designs can be classified according to the means by which the rotor is suspended: contact bearings, magnetic bearings or hydrodynamic bearings, though some designs use two of these means.

Contact or pivot bearings, as exemplified by U.S. Pat. No. 5,527,159 to Bozeman et al. and U.S. Pat. No. 5,399,074 to Nose et al., have potential problems due to wear, and cause very high localised heating and shearing of the blood, which can cause deposition and denaturation of plasma proteins, with the risk of embolisation and bearing seizure.

Magnetic bearings, as exemplified by U.S. Pat. No. 5,350,283 to Nakazeki et al., U.S. Pat. No. 5,326,344 to Bramm et al. and U.S. Pat. No. 4,779,614 to Moise et al., offer contactless suspension, but require rotor position measurement and active control of electric current for stabilisation of the position in at least one direction, according to Earnshaw's theorem. Position measurement and feedback control introduce significant complexity, increasing the failure risk. Power use by the control current implies reduced overall efficiency. Furthermore, size, mass, component count and cost are all increased.

U.S. Pat. No. 5,507,629 to Jarvik claims to have found a configuration circumventing Earnshaw's Theorem and thus requiring only passive magnetic bearings, but this is doubtful and contact axial bearings are included in any case. Similarly, passive radial magnetic bearings and a pivot point are employed in U.S. Pat. No. 5,443,503 to Yamane.

Prior to the present invention, pumps employing hydrodynamic suspension, such as U.S. Pat. No. 5,211,546 to Isaacson et al. and U.S. Pat. No. 5,324,177 to Golding et al., have used journal bearings, in which radial suspension is provided by the fluid motion between two cylinders in relative rotation, an inner cylinder lying within and slightly off axis to a slightly larger diameter outer cylinder. Axial suspension is provided magnetically in U.S. Pat. No. 5,324,177 and by either a contact bearing or a hydrodynamic thrust bearing in U.S. Pat. No. 5,211,546.

U.S. Pat. No. 4,944,748 discloses a magnetically suspended impeller within a pump. It does not disclose an exclusively hydrodynamically suspended impeller within a pump.

U.S. Pat. No. 4,688,998 again discloses a magnetically suspended impeller. It does not disclose a hydrodynamically suspended impeller, much less an exclusively hydrodynamically suspended impeller within a pump.

WO 91/19103 to NU-TECH discloses an axial flow blood pump having a hydrodynamically suspended rotor assisted by magnetic or mechanical stabilisation.

U.S. Pat. No. 5,112,200 to NU-TECH discloses hydrodynamic support in at least one dimension, but utilising prior art hydrodynamic lift surfaces which do not include the deformed surfaces of the present invention.

WO 94/13955 discloses a fluid pump which relies on a magnetically levitated impeller.

U.S. Pat. No. 4,382,199 to NU-TECH discloses a rotor and impeller combination which employs "squeeze film effects, dash pot effects and hydrodynamic effects, all of which combine and co-operate to prevent metal-to-metal contact between the rotor and the stator and to lubricate the rotor as it rotates within the stator" (column 6). There is no disclosure of exclusive hydrodynamic support in all dimensions by the use of deformed surfaces.

A purging flow is needed through the journal bearing, a high shear region, in order to remove dissipated heat and to prevent long fluid residence time. It would be inefficient to pass all the fluid through the bearing gap, of small cross-sectional area, as this would demand an excessive pressure drop across the bearing. Instead a leakage path is generally provided from the high pressure pump outlet, through the bearings and back to the low pressure pump inlet, implying a small reduction in outflow and pumping efficiency. U.S.

Pat. No. 5,324,177 provides a combination of additional means to increase the purge flow, namely helical grooves in one of the bearing surfaces, and a small additional set of impellers.

U.S. Pat. No. 5,211,546 provides 10 embodiments with various locations of cylindrical bearing surfaces. One of these embodiments, the third, features a single journal bearing and a contact axial bearing.

Embodiments of the present invention offer a relatively low cost and/or relatively low complexity means of suspending the rotor of a seal-less blood pump, thereby overcoming or ameliorating the problems of existing devices mentioned above.

SUMMARY OF THE INVENTION

According to one aspect of the present invention there is disclosed a rotary blood pump for use in a heart assist device or like device, said pump having an impeller suspended in use within a pump housing exclusively by hydrodynamic thrust forces generated by relative movement of said impeller with respect to and within said pump housing; and wherein at least one of said impeller or said housing includes at least one deformed surface lying on at least part of a first face and a second deformed surface lying on at least part of a second face which, in use, move relative to respective facing surfaces on the other of said impeller or said housing thereby to form at least two relatively moving surface pairs which generate relative hydrodynamic thrust between said impeller and said housing which includes everywhere a localized thrust component substantially and everywhere normal to the plane of movement of said first deformed surface and said second deformed surface with respect to said facing surfaces; and wherein the combined effect of the localized normal forces generated on the surfaces of said impeller is to produce resistive forces against movement in three translational and two rotational degrees of freedom.

In yet a further broad form of the invention there is provided an estimation and control system for a pump; said pump of the type having an impeller located within a pump cavity in a pump housing; said housing having a fluid inlet in fluid communication with said cavity; said housing having a fluid outlet in fluid communication with said pump cavity; said impeller urged to rotate about an impeller axis so as to cause fluid to be urged from said inlet through said pump cavity to said pump outlet; said impeller urged to rotate by impeller urging means; said impeller supported for rotational movement by impeller support means; said impeller maintained at or near a predetermined speed of rotation by control means acting on said impeller urging means; said control means receiving as input variables a first input variable comprising power consumed by said urging means; said control means receiving a second input variable comprising actual speed of rotation of said impeller; said control means thereby estimating head across the pump and/or rate of flow of said fluid to an approximation of predetermined accuracy relying on signals available from said urging means; said control system adapted to maintain speed of rotation of said impeller within a range whereby said impeller, in use, substantially resists five degrees of freedom of movement with respect to said pump housing predominantly without any external intervention from said control system to control the position of said impeller with respect to said housing.

In yet a further broad form of the invention there is provided a rotary blood pump and an estimation and control system therefor, said pump having an impeller suspended hydrodynamically within a pump housing by thrust forces generated by the impeller during movement in use of the impeller as it rotates about an impeller axis; said estimation and control system as described above.

In yet a further broad form of the invention there is provided a rotary blood pump having a housing within which an impeller acts by rotation about an impeller axis to cause a pressure differential between an inlet side of the pump housing of said pump and an outlet side of the pump housing said pump; said impeller suspended hydrodynamically by thrust forces generated by the impeller during movement in use of the impeller; said pump controlled by the estimation and control system as described above.

In yet a further broad form of the invention there is provided a seal-less, shaft-less pump comprising a housing defining a chamber therein and having a liquid inlet to said chamber and a liquid outlet from said chamber, said pump further including an impeller located within said chamber; the arrangement between said impeller, said inlet, said outlet and the internal walls of said chamber being such that upon rotation of said impeller about an impeller axis relative to said housing, liquid is urged from said inlet through said chamber to said outlet; and wherein thrust forces are generated by relative movement of said impeller with respect to said housing; said pump controlled by the estimation and control system as described above.

In yet a further broad form of the invention there is provided a pump having a housing within which an impeller acts by rotation about an axis to cause a pressure differential between an inlet side of a housing of said pump and an outlet side of the housing of said pump; said impeller suspended hydrodynamically in at least one of a radial or axial direction by thrust forces generated by the impeller during movement in use of the impeller, said pump controlled by the estimation and control system as described above.

In yet a further broad form of the invention there is provided a method of hydrodynamically suspending and controlling an impeller within a rotary pump for support in at least one of a radial or axial direction; said method comprising incorporating a deformed surface in at least part of said impeller so that, in use, a thrust in created between said deformed surface and the adjacent pump casing during relative movement therebetween; said method further including the step of maintaining speed of rotation of said impeller within a range whereby said impeller, in use, substantially resists five degrees of freedom of movement with respect to said pump housing without any external intervention.

In yet a further broad form of the invention there is provided an estimation and control system for a pump; said pump of the type having an impeller located within a pump cavity in a pump housing; said housing having a fluid inlet in fluid communication with said cavity; said housing having a fluid outlet in fluid communication with said pump cavity, said impeller urged to rotate about an impeller axis so as to cause fluid to be urged from said inlet through said pump cavity to said pump outlet; said impeller urged to rotate by impeller urging means; said impeller supported for rotational movement by impeller support means; said pump maintained at or near a predetermined operating point by control means acting on said impeller urging means; said control means receiving as input variables at least a first input variable derived from said urging means; said control means receiving at least a second input variable also derived from said urging means, said control means thereby calculating an estimate of said operating point to an approximation of predetermined accuracy relying on signals available from said urging means; said control means controlling said pump by comparing said predetermined operating point with said estimate of said operating point; and wherein instantaneous pump speed and electrical input power are allowed to be modulated by the heart, in use, by appropriate selection of a control time constant.

In yet a further broad form of the invention there is provided a physiological controller for use in association with a pump; said controller monitoring estimated flow of fluid within said pump and pressure across said pump by non-contact means thereby to control speed of rotation of an impeller within said pump; and wherein said controller permits impeller speed to vary under a pulsating fluid load thereby to assist in calculation and adjustment of impeller speed set point.

Preferably said pump comprises a ventricular assist device adapted to assist operation of a ventricle of a heart and wherein said control means adjusts pump output so that, in alternating fashion, said ventricle in conjunction with said aortic valve is allowed to eject blood over a predetermined number of cardiac cycles and then said ventricle in conjunction with said aortic valve is caused to not eject blood over a following predetermined number of cardiac cycles.

In yet a further broad form of the invention there is provided an estimation and control system for a pump; said pump of the type having an impeller located within a pump cavity in a pump housing; said housing having a fluid inlet in fluid communication with said cavity; said housing having a fluid outlet in fluid communication with said pump cavity; said impeller urged to rotate about an impeller axis so as to cause fluid to be urged from said inlet through said pump cavity to said pump outlet; said impeller urged to rotate by impeller urging means; said impeller supported for rotational movement by impeller support means; said pump maintained at or near a predetermined operating point by control means acting on said impeller urging means, said control means receiving as input variables at least a first input variable derived from said urging means; said control means receiving at least a second input variable also derived from said urging means; said control means thereby calculating an estimate of said operating point to an approximation of predetermined accuracy relying on signals available from said urging means; said control means controlling said pump by comparing said predetermined operating point with said estimate of said operating point; and wherein said pump is arranged to operate according to a relatively flat HQ characteristic.

Preferably there is no inflexion point in said HQ characteristic at or near said predetermined operating point.

Preferably said pump includes near-radial off-flow from said impeller.

Preferably said pump has a low specific speed.

Preferably said pump is a low specific speed pump.

Preferably said pump has a specific speed in the range 100–2000 rev/min (gal/min)$^{1/2}$ft$^{-3/4}$.

Preferably said pump has a specific speed of approximately 900–1000 rev/min (gal/min)$^{1/2}$ft$^{-3/4}$.

Preferably instantaneous pump speed and electrical input power are allowed to be modulated by the heart, in use, by appropriate selection of time constant.

Preferably the time constant of the control system is greater than the rotational, inertial time constant of the impeller.

Preferably said time constant is at least one cardiac cycle.

Preferably said first input variable comprises instantaneous pump speed.

Preferably said second input variable comprises electrical input power to said impeller urging means.

Preferably said pump is arranged to operate according to a relatively flat HQ characteristic.

Preferably variation in speed of said impeller, in use, is utilized to calculate an estimate of said operating point to an improved level of accuracy.

In a particular preferred form said HQ characteristic is sufficiently flat that head will remain constant to a sufficient approximation over a predetermined operating range whereby, over said operating range, said system can assume that pump speed will be proportional to flow rate.

Preferably said predetermined operating point is calculated so as to maintain minimum pump speed such that the minimum head pressure across the pump does not increase.

Preferably said system ensures that minimum pump speed is always greater than or equal to the minimum speed at which non-regurgitant flow will occur.

Preferably the speed at which regurgitant or negative flow will begin to occur is determined as that pump set point speed where levels and phase lags between pump outlet and inlet pressures fall during diastole cause flow reversal.

In a particular preferred form the pump speed at which regurgitation is calculated to occur is calculated according to:

$$N\text{regurg}=N(t) \text{ for Q}_\text{diastole}=0\text{L/min}$$

BRIEF DESCRIPTION OF THE DRAWINGS

Embodiments of the present invention will now be described, with reference to the accompanying drawings, wherein.

DETAILED DESCRIPTION OF PREFERRED EMBODIMENTS

The pump assemblies according to various preferred embodiments to be described below all have particular, although not exclusive, application for implantation in a mammalian body so as to at least assist, if not take over, the function of the mammalian heart. In practice this is performed by placing the pump assembly entirely within the body of the mammal and connecting the pump between the left ventricle and the aorta so as to assist left side heart function. It may also be connected to the right ventricle and pulmonary artery to assist the right side of the heart.

In this instance the pump assembly includes an impeller which is fully sealed within the pump body and so does not require a shaft extending through the pump body to support it. The impeller is suspended, in use, within the pump body by the operation of hydrodynamic forces imparted as a result of the interaction between the rotating impeller, the internal pump walls and the fluid which the impeller causes to be urged from an inlet of the pump assembly to an outlet thereof.

Figure 1:
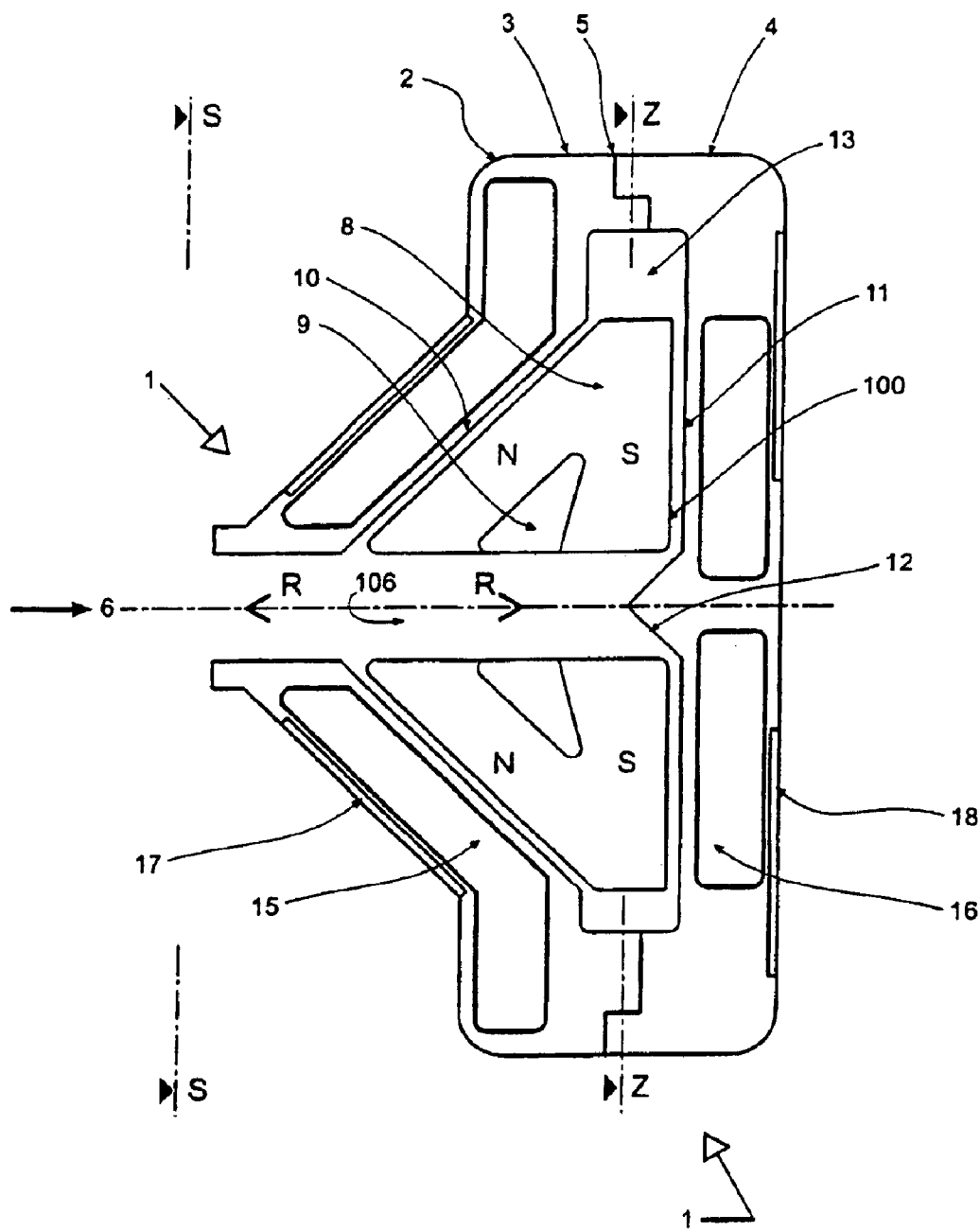
FIG. 1 is a longitudinal cross-sectional view of a preferred embodiment of the invention.
Figure 2:
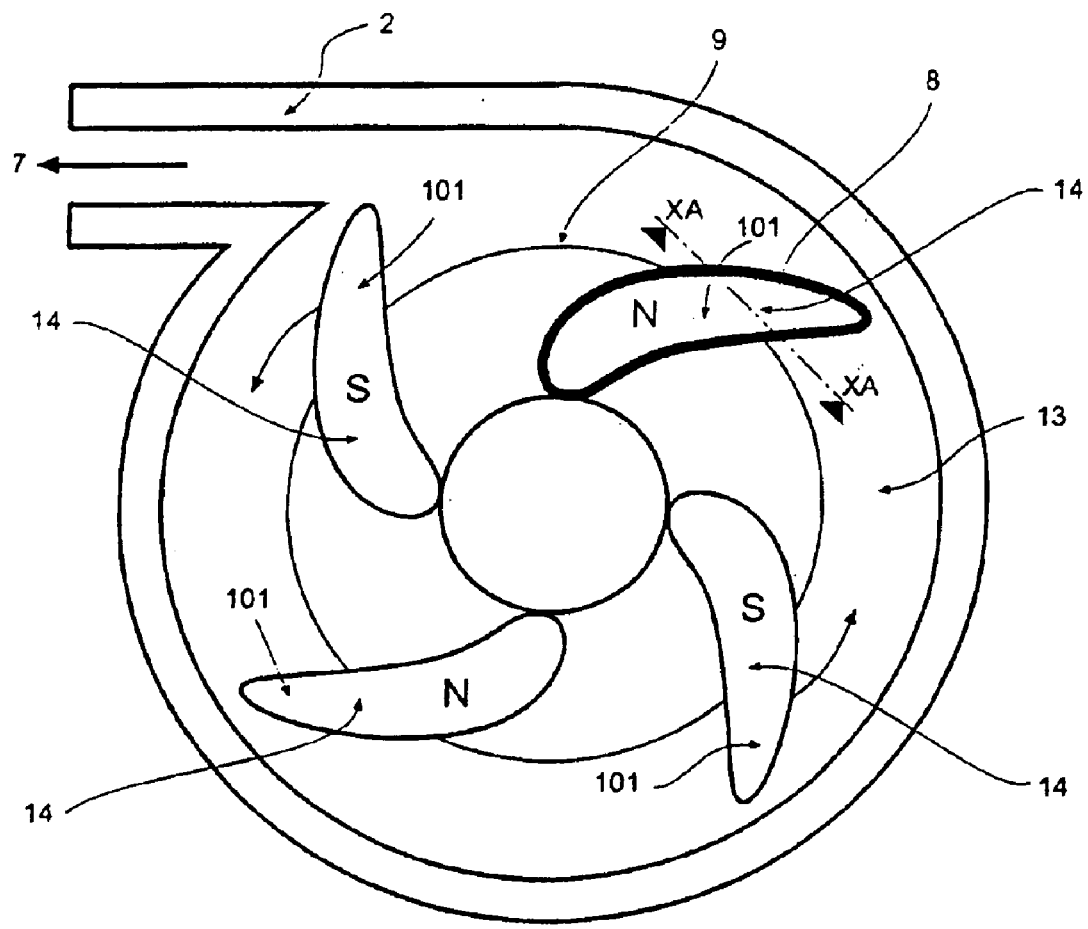
FIG. 2 is a cross-sectional view taken generally along the line Z—Z of FIG. 1.

A preferred embodiment of the invention is the centrifugal pump 1, as depicted in FIGS. 1 and 2, intended for implantation into a human, in which case the fluid referred to below is blood. The pump housing 2, can be fabricated in two parts, a front part 3 in the form of a housing body and a back part 4 in the form of a housing cover, with a smooth join therebetween, for example at 5 in FIG. 1. The pump 1 has an axial inlet 6 and a tangential outlet 7. The rotating part 100 is of very simple form, comprising only blades 8 and a blade support 9 to hold those blades fixed relative to each other. The blades may be curved as depicted in FIG. 2, or straight, in which case they can be either radial or backswept, i.e. at an angle to the radius. This rotating part 100 will hereafter be called the impeller 100, but it also serves as a bearing component and as the rotor of a motor configuration as to be further described below whereby a torque is applied by electromagnetic means to the impeller 100. Note that the impeller has no shaft and that the fluid enters the impeller from the region of its axis RR. Some of the fluid passes in front of the support 9 and some behind it, so that the pump 1 can be considered of two-sided open type, as compared to conventional open centrifugal pumps, which are only open on the front side. Approximate dimensions found adequate for the pump 1 to perform as a ventricular assist device, when operating at speeds in the range 1,500 rpm to 4,000 rpm, are outer blade diameter 40 mm, outer housing average diameter 60 mm, and housing axial length 40 mm.

Figures 3A, 3C:
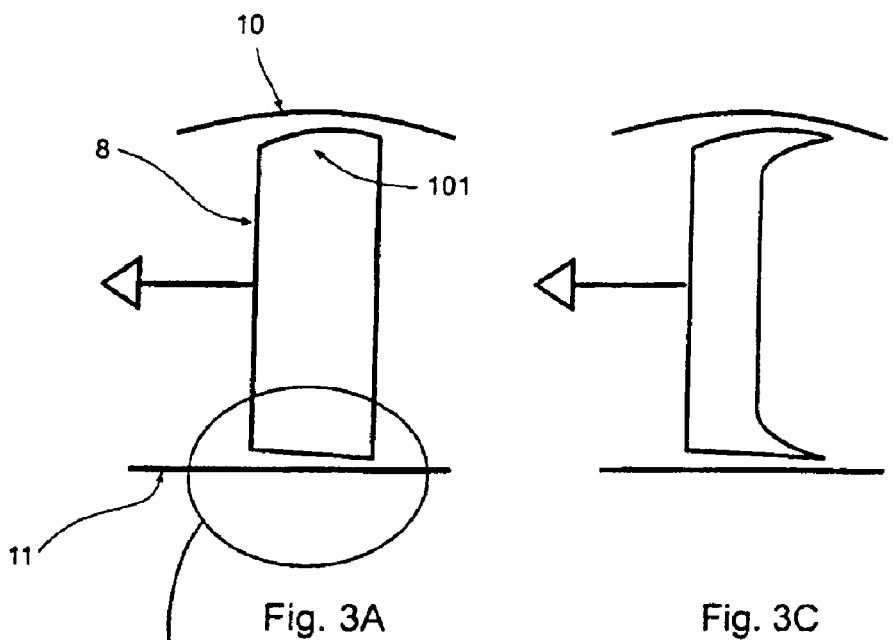
FIG. 3A is a cross-sectional view of an impeller blade taken generally along the line A—A of FIG. 2.
FIG. 3C is an alternative impeller blade shape.
Figure 3B:
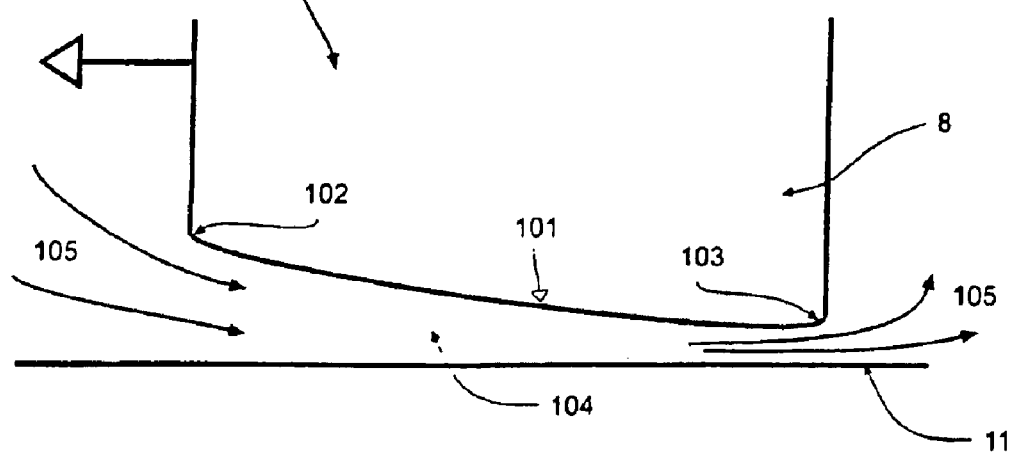
FIG. 3B is an enlargement of the blade-pump housing interface portion of FIG. 3A.

As the blades 8 move within the housing, some of the fluid passes through the gaps, much exaggerated in FIGS. 1 and 3, between the blade bearing faces 101 and the housing front face 10 and housing back face 11. In all open centrifugal pumps, the gaps are made small because this leakage flow lowers the pump hydrodynamic efficiency. In the pump disclosed in this embodiment, the gaps are made smaller than is conventional in order that the leakage flow can be utilised to create a hydrodynamic bearing. For the hydrodynamic forces to be sufficient, the blades may also be tapered as depicted in FIGS. 3A and 3B, so that the gap 104 is larger at the leading edge 102 of the blade 8 than at the trailing edge 103 thereby providing one example of a wedge-shaped restriction defined by at least one "deformed surface" as described elsewhere in this specification and a corresponding opposing surface. The fluid 105 which passes through the gap thus experiences a wedge shaped restriction which generates a thrust, as described in Reynolds' theory of lubrication (see, for example, "Modern Fluid Dynamics, Vol. 1 Incompressible Flow", by N. Curle and H. J. Davies, Van Nostrand, 1968). For blades considerably thinner than their length, the thrust is proportional to the square of the blade thickness at the bearing face, and thus in this embodiment thick blades are favoured, since if the proportion of the pump cavity filled by blades is constant, then the net thrust force will be inversely proportional to the number of blades. However, the blade bearing faces can be made to extend as tails from thin blades as depicted in FIG. 3C in order to increase the blade face area adjacent the walls.

In one particular form, the tails join adjacent blades so as to form a complete shroud with wedges or tapers incorporated therein. An example of a shroud design as well as other variations on the blade structure will be described later in this specification.

For manufacturing simplicity, the housing front face 10 can be made conical, with an angle of around 45° so that it provides both axial and radial hydrodynamic forces. Other angles are suitable that achieve the functional requirements of this pump including the requirements for both axial and radial hydrodynamic forces.

Other curved surfaces are possible provided both axial and radial hydrodynamic forces can be produced as a result of rotation of the blades relative to the housing surfaces.

In one form the housing back face 11 may include a roughly conical extension 12 pointing into the pump cavity 106, to eliminate or minimise the effect of the flow stagnation point on the axis of the back housing.

Alternatively extension 12 can resemble an impeller eye to make the flow mixed.

In an alternative form the extension 12 can be omitted for ease of manufacture.

In this preferred embodiment, for manufacturing simplicity and for uniformity in the flow axial direction RR, the housing back face 11 is made flat over the bearing surfaces, i.e. under the blade bearing faces. With this the case, a slacker tolerance on the alignment between the axes of the front part 3 and back part 4 of the housing 2 is permissible. An alternative is to make the back face 11 conical at the bearing surfaces, with taper in the opposite direction to the front face 10, so that the hydrodynamic forces from the back face will also have radial components. Tighter tolerance on the axes alignment would then be required, and some of the flow would have to undergo a reversal in its axial direction.

There are many profiles of bearing surface which will generate the wedge-shaped restriction. In the preferred embodiment the amount of material removed simply varies linearly or approximately linearly across the blade between the body and trailing edges. Alternatively tapered shaped can include a radiused leading edge or a step in the blade bearing face, though the corner in that step may represent a stagnation line posing a thrombosis risk.

For a given minimum gap, at the trailing blade edge, the hydrodynamic force is maximal if the gap at the leading edge of the blade end face is approximately double that at the railing edge of the blade end face. Thus the taper, which equals the blade face leading edge gap minus the trailing edge gap, should be chosen to match a nominal minimum gap, once the impeller has shifted towards that edge. Dimensions which have been found to give adequate thrust forces are a taper of around 0.05 mm for a nominal minimum gap of around 0.05 mm, and an average circumferential blade bearing face thickness of around 6 mm for 4 blades. For the front face, the taper is measured within the plane perpendicular to the axis. The axial length of the housing between the front and back faces at any position should then be made about 0.2 mm greater than the axial length of the blade, when it is coaxial with the housing, so that the minimum gaps are both about 0.1 mm axially when the impeller 100 is centrally positioned within the housing 2. Then, for example, if the impeller shifts axially by 0.05 mm, the minimum gaps will be 0.05 mm at one face and 0.15 mm at the other face. The thrust increases with decreasing gap and would be much larger from the 0.05 mm gap than from the 0.15 mm gap, about 14 times larger for the above dimensions. Thus there is a net restoring force away from the smaller gap.

Similarly, for radial shifts of the impeller the radial component of the thrust from the smaller gap on the conical housing front face would offer the required restoring radial force. The axial component of that force and its torque on the impeller would have to be balanced by an axial force and torque from the housing back face, and so the impeller will also have to shift axially and tilt its axis to be no longer parallel with the housing axis. Thus as the person moves and the pump is accelerated by external forces, the impeller will continually shift its position and alignment, varying the gaps in such a way that the total force and torque on the impeller 100 match that demanded by inertia. The gaps are so small, however, that the variation in hydrodynamic efficiency will be small, and the pumping action of the blades will be approximately the same as when the impeller is centrally located.

While smaller gaps imply greater hydrodynamic efficiency and greater bearing thrust forces, smaller gaps also demand tighter manufacturing tolerances, increase frictional drag on the impeller, and impose greater shear stress an the fluid. Taking these points in turn, for the above 0.05 mm tapers and gaps, tolerances of around 0.005 mm are needed, which imposes some cost penalty but is achievable. A tighter tolerance is difficult, especially if the housing is made of a plastic, given the changes in dimension caused by temperature and possible absorption of fluid by plastic materials which may be in contact with the blood such as Acrylic of polyurethane. The frictional drag for the above gaps produces much smaller torque than the typical motor torque. Finally, to estimate the shear stress, consider a rotation speed of 3,000 rpm and a typical radius of 15 mm, at which the blade speed is 4.7 ms$^{-1}$ and the average velocity shear for an average gap of 0.075 mm is $6.2 \times 10^4$ s$^{-1}$. For blood of dynamic viscosity $3.5 \times 10^{-3}$ kgm$^{-1}$s$^{-1}$, the average shear stress would be 220 Nm$^{-2}$. Other prototype centrifugal blood pumps with closed blades have found that slightly larger gaps, e.g. 0.15 mm, are acceptable for haemolysis. A major advantage of the open blades of the present invention is that a fluid element that does pass through a blade bearing face gap will have very short residence time in that gap, around $2 \times 10^{-3}$ s, and the fluid element will most likely be swept though the pump without passing another blade bearing face.

With particular reference to FIGS. 3A and 3B typical working clearances and working movement for the impeller 8 with respect to the upper and lower housing surfaces 10, 11 is of the order of 100 microns clearance at the top and at the bottom. In use gravitational and other forces will bias the impeller 8 closer to one or other of the housing walls resulting, typically in a clearance at one interface of the order of 50 microns and a corresponding larger clearance at the other interface of the order of 150 microns. In use, likely maximum practical clearances will range from 300 microns down to 1 micron.

Typical restoring forces for a 25 gram rotor mass spinning at 2200 rpm are 1.96 Newtons at a 20 micron clearance extending to 0.1 Newtons at an 80 micron clearance.

To minimise the net force required of the hydrodynamic bearings, the net axial and radial hydrodynamic forces on the impeller from the bulk fluid flow should be minimised, where "bulk" here means other than from the bearing thrust surfaces.

The radial force on the impeller depends critically on the shape of the output flow collector or volute 13. The shape should be designed to minimise the radial impeller force over the desired range of pump speeds, without excessively lowering the pump efficiency. The optimal shape will have a roughly helical perimeter between the "cutwater" and outlet. The radial force can also be reduced by the introduction of an internal division in the volute 13 to create a second output flow collector passage, with tongue approximately diametrically opposite to the tongue of the first passage.

An indicative plan view of impeller 100 relative to housing 2 is shown in FIG. 2 having a concentric volute 13.

Figure 17:
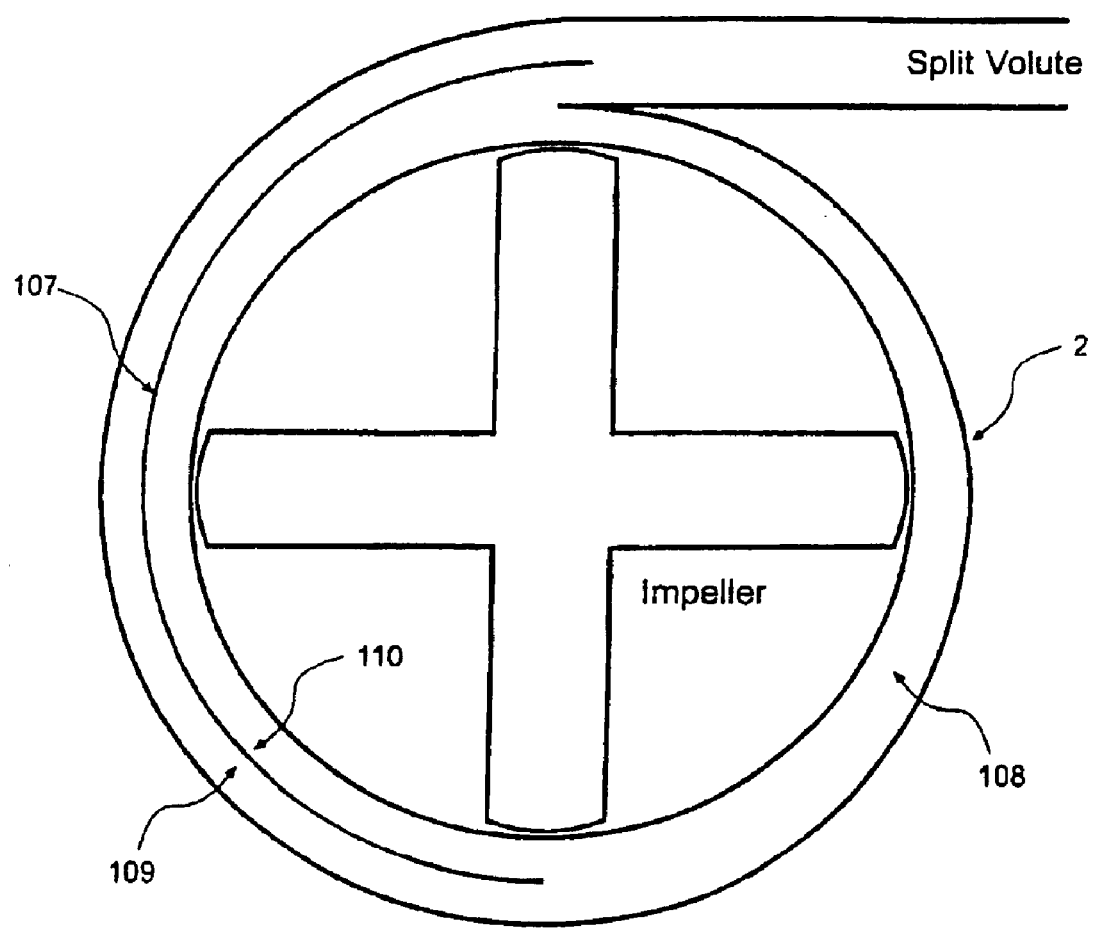
FIG. 17 is a plan, section view of a pump assembly showing an alternative volute arrangement.

FIG. 17 illustrates the alternative volute arrangement comprising a split volute created by volute barrier 107 which causes volute 108 in a first hemisphere of the housing 2 to split into first half volute 109 and second half volute 110 over the second hemisphere. The hemispheres are defined respectively on each side of a diameter of the housing 2 which passes through or near exit point 111 of outlet 7.

In alternative forms concentric volutes can be utilised, particularly where specific speed is relatively low.

In a further particular form a vaneless diffuser may also reduce the radial force.

In regard to the bulk hydrodynamic axial force, if the blade cross-section is made uniform in the axial direction along the rotational axis, apart from the conical front edge surface, then the pressure acting on the blade surface (excluding the bearing surfaces) will have no axial component. This also simplifies the blade manufacture. The blade support 9 should then be shaped to minimise axial thrust on the impeller and minimise disturbance to the flow over the range of speeds, while maintaining sufficient strength to prevent relative blade movement. The key design parameter affecting the axial force is the angle of the support. The support is drawn in FIG. 1 as having the same internal diameter as the blades, which may aid manufacture. However, the support could be made with larger or smaller internal diameter to the blades. There may be advantage in using a non-axisymmetric support, e.g. with larger radius on the trailing surface of a blade than the radius at the leading surface of the next blade. If the blades are made with non-uniform cross-section to increase hydrodynamic efficiency, then any bulk hydrodynamic axial force on them can be balanced by shaping the support to produce an opposite bulk hydrodynamic axial force on it.

Alternatively, by careful manufacture of taper axial thrust can be engineered.

Careful design of the entire pump, employing computational fluid dynamics, is necessary to determine the optimal shapes of the blades 8, the volute 13, the support 9 and the housing 2, in order to maximise hydrodynamic efficiency while keeping the bulk fluid hydrodynamic forces, shear and residence times low. All edges and the joins between the blades and the support should be smoothed.

The means of providing the driving torque on the impeller 100 of the preferred embodiment of the invention is to encapsulate permanent magnets 14 in the blades 8 of the impeller 100 and to drive them with a rotating magnetic field pattern from oscillating currents in windings 15 and 16, fixed relative to the housing 2. Magnets of high remanence such as sintered rare-earth magnets should be used to maximise motor efficiency. The magnets can be aligned axially but greater motor efficiency is achieved by tilting the magnetisation direction to an angle of around 15° to 30° outwards from the inlet axis, with 22.5° tilt suitable for a body of conical angle 45°. The magnetisation direction must alternate in polarity for adjacent blades. Thus there must be an even number of blades. Since low blade number is preferred for the bearing force, and since two blades would not have sufficient bearing stiffness to rotation about an axis through the blades and perpendicular to the pump housing (unless the blades are very curved), four blades are recommended. A higher number of blades, for example 6 or 8 will also work.

Figures 4A, 4B, 4C:
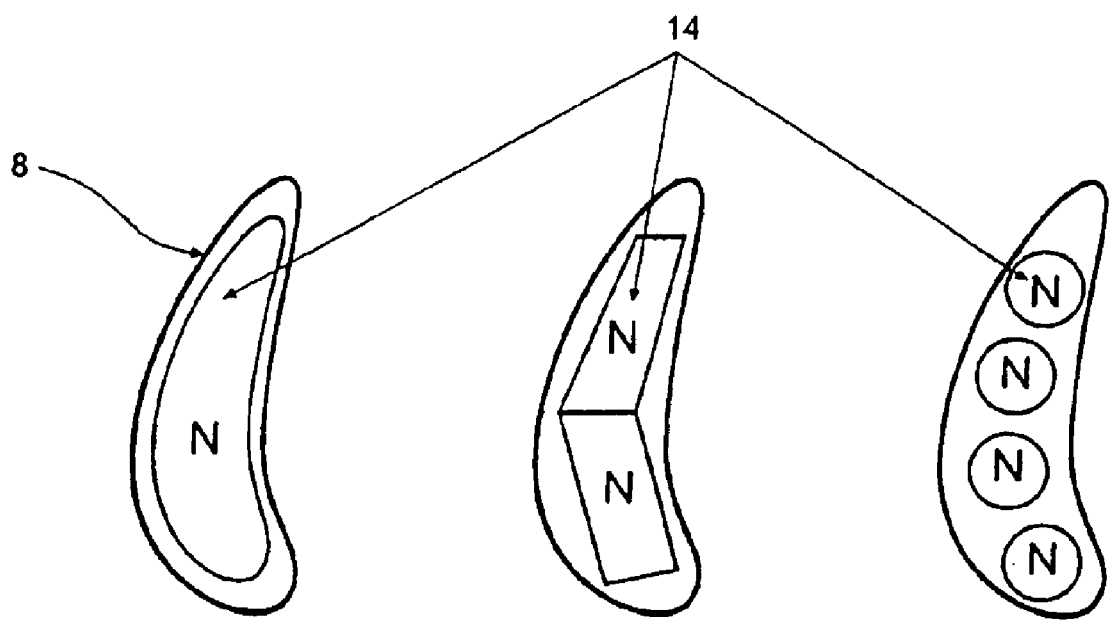
FIGS. 4A, B, C illustrate various possible locations of magnet material within a blade.

Some possible options for locating the magnets 14 within the blades 8 are shown in FIG. 4. The most preferred which is depicted in FIG. 4A, is for the blade to be made of magnet material apart from a biocompatible shell or coating to prevent fluid corroding the magnets and to prevent magnet material (which may be toxic) entering the blood stream. The coating should also be sufficiently durable especially at blade corners to withstand rubbing during start-up or during inadvertent bearing touch down.

In one particular form the inside walls of the pump housing 2 are also coated with a biologically compatible and wear resistant material such as titanium nitride so that wear on both of the touching surfaces is minimised.

An acceptable coating thickness is approximately 1 micron.

In one form the magnet material can be potted in titanium or a polymeric housing which is then, in turn, coated with a biologically compatible and tough material such as titanium nitride.

In an alternative form a suitable impeller manufacturing method is to die-press the entire impeller, blades and support, as a single axially aligned magnet. The die-pressing is much simplified if near axially uniform blades are used (blades with an overhang such as in FIG. 3C are precluded). During pressing, the crushed rare-earth particles must be aligned in an axial magnetic field. This method of die-pressing with parallel alignment direction is cheaper for rare-earth magnets, although it produces slightly lower remanence magnets. The tolerance in die-pressing is poor, and grinding of the tapered blade surfaces is required. Then the magnet impeller can be coated, for example by physical vapour deposition, of titanium nitride for example, or by chemical vapour deposition, of a teflon coating.

Finally, to create the alternating blade polarity the impeller may be placed in a special pulse magnetisation fixture, with an individual coil surrounding each blade. The support of a die-pressed magnet impeller acquires some magnetisation near the blades, with negligible influence.

Alternative magnet locations are sketched in FIG. 4B and FIG. 4C in which quadrilateral or circular cross-section magnets 14 are inserted into the blades. Sealing and smoothing of the blade bearing surfaces over the insertion holes is then required to reinstate the taper.

All edges in the pump should be radiused and surfaces smoothed to avoid possible damage to formed elements of the blood.

The windings 15 and 16 of the preferred embodiment are slotless or air-gap windings with the same pole number as the impeller, namely four poles in the preferred embodiment.

A ferromagnetic iron yoke 17 of conical form for the front winding and an iron ferromagnetic yoke 18 of annular form for the back winding may be placed on the outside of the windings to increase the magnetic flux densities and hence increase motor efficiency. The winding thicknesses should be designed for maximum motor efficiency, with the sum of their axial thicknesses somewhat less than but comparable to the magnet axial length. The yokes can be made of solid ferromagnetic material such as iron. To reduce "iron" losses, the yokes 17 can be laminated, for example in layers or by helically winding thin strip, or can be made of iron/powder epoxy composite. The yokes should be positioned such that there is zero net axial magnetic force on the impeller when it is positioned centrally in the housing. The magnetic force is unstable and increases linearly with axial displacement of the impeller away from the central position, with the gradient being called the negative stiffness of the magnetic force. This unstable magnetic force must be countered by the hydrodynamic bearings, and so the stiffness should be made as small as possible. Choosing the yoke thickness such that the flux density is at the saturation level reduces the stiffness and gives minimum mass. An alternative can be to have no iron yokes, completely eliminating the unstable axial magnetic force, but the efficiency of such designs may be lower and the magnetic flux density in the immediate vicinity of the pump may violate safety standards and produce some tissue heating. In any case, the stiffness is acceptably small for slotless windings with the yokes present. Another alternative would be to insert the windings in slots in laminated iron stators which would increase motor efficiency and enable use of less magnet material and potentially lighter impeller blades. However, the unstable magnetic forces would be significant for such slotted motors. Also, the necessity for fat blades to generate the required bearing forces in this embodiment allows room for large magnets, and so slotless windings are chosen in the preferred embodiment.

Instead of determining the yoke positions so that the impeller has zero magnetic axial force in the central position, it may be possible to provide a bias axial magnetic force on the impeller, which can counteract other forces such as any average bulk hydrodynamic axial force. In particular, by ensuring a net axial force into the conical body, the thrust bearings on the cover surface can be made superfluous. However, such a bias would demand greater average thrust forces, smaller gaps and increased blood damage, and so the recommended goal is to zero both the magnetic and bulk hydrodynamic axial forces on the impeller when centrally positioned.

The overall design requirement for exclusive hydrodynamic suspension requires control of the external force balance to make the relative magnitude of hydrodynamic thrust sufficient to overcome the external forces. Typical external forces include gravitational forces and net magnetic forces arising as a result of the motor drive.

Figure 5A:
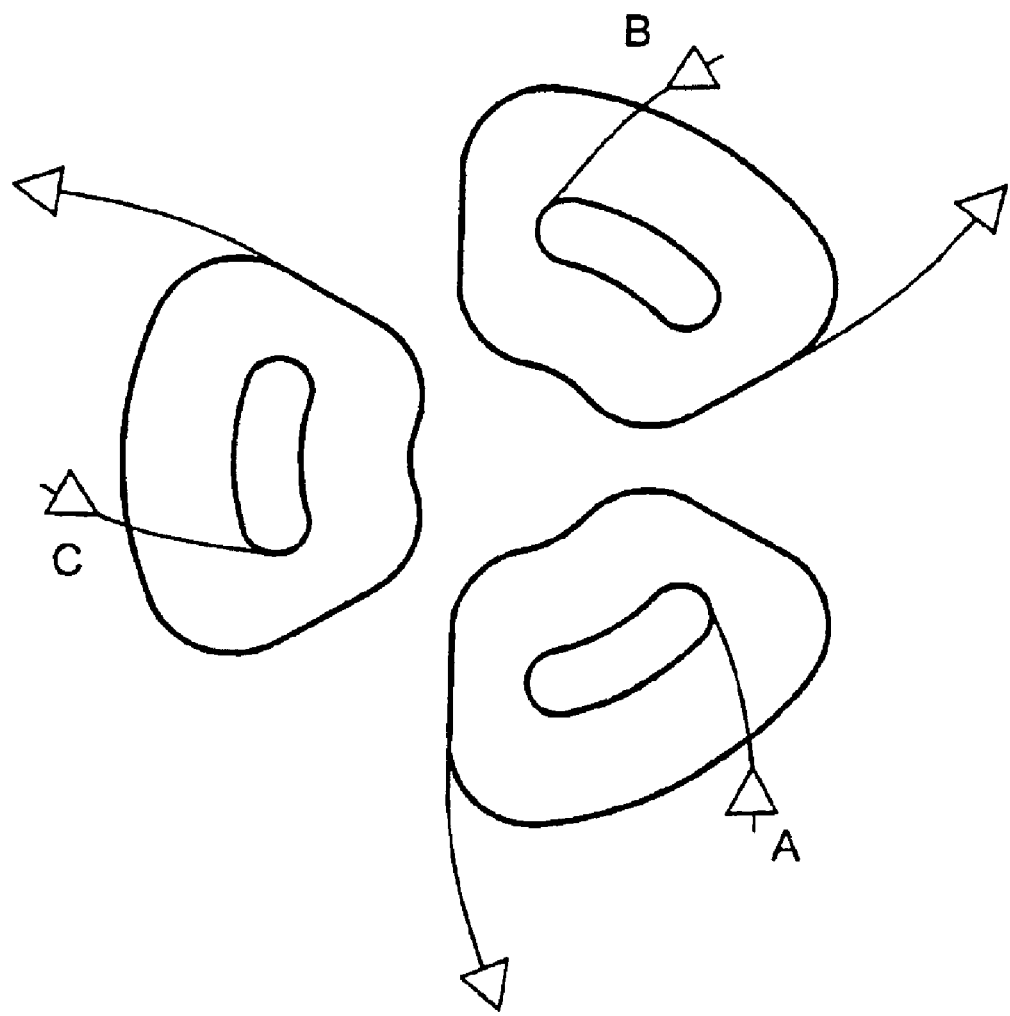
FIGS. 5A, B and C are left-hand end views of possible winding geometries taken generally along the line S—S of FIG. 1.

There are many options for the winding topology and number of phases. FIG. 5A depicts the preferred topology for the body winding 15, viewed from the inlet axis.

The cover winding 16 looks similar but the coils need not avoid the inlet tube and so they appear more triangular in shape. The body winding has a more complex three-dimensional shape with bends at the ends of the body support section. Each winding consists of three coils. Each coil is made from a number of turns of an insulated conductor such as copper with the number of turns chosen to suit the desired voltage. The coil side mid-lines span an angle of about 50°–100° at the axis when the coils are in position. The coils for body and cover are aligned axially and the axially adjacent coils are connected in either parallel or series connection to form one phase of the three phase winding. Parallel connection offers one means of redundancy in that if one coil fails, the phase can still carry current through the other coil. In parallel connection each of the coil and body winding has a neutral point connection as depicted in FIG. 5A, whereas in series connection, only one of the windings has a neutral point.

Figure 5B:
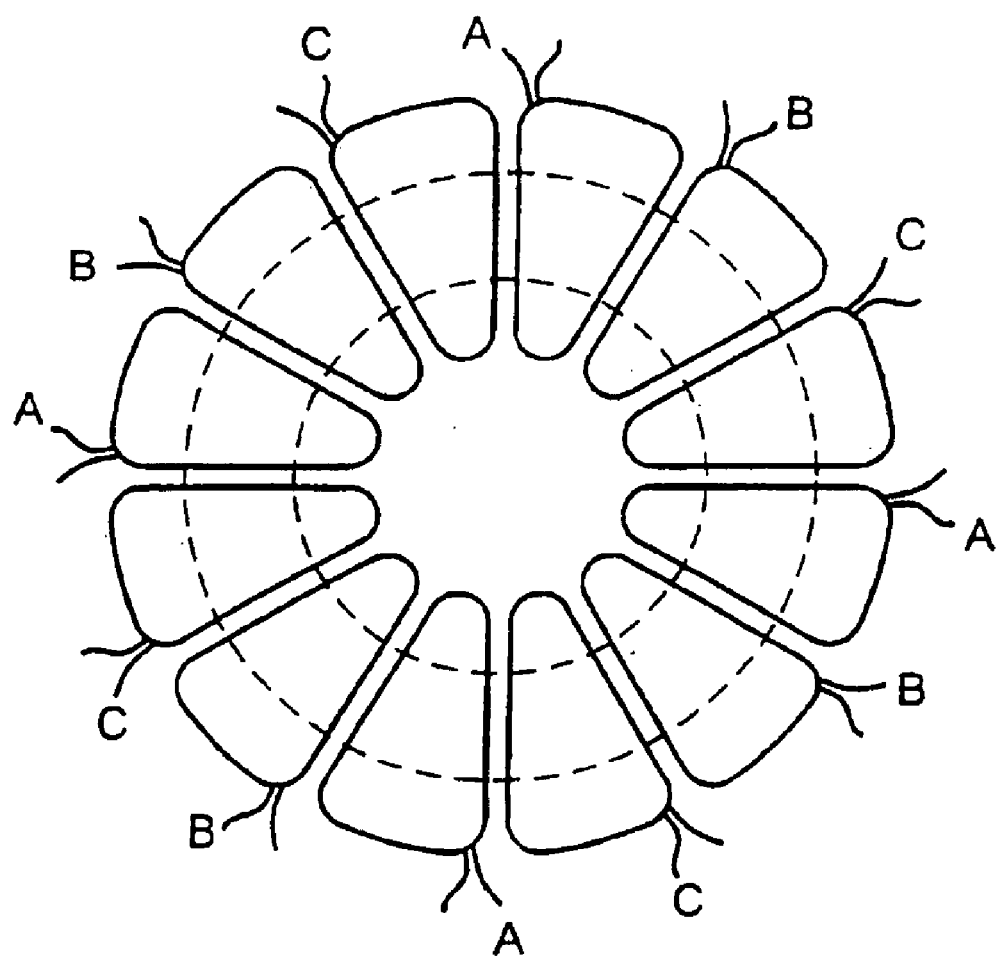

An alternative three phase winding topology, depicted in FIG. 5B, uses four coils per phase for each of the body and cover windings, with each coil wrapping around the yoke, a topology called a "Gramm ring" winding.

Figure 5C:
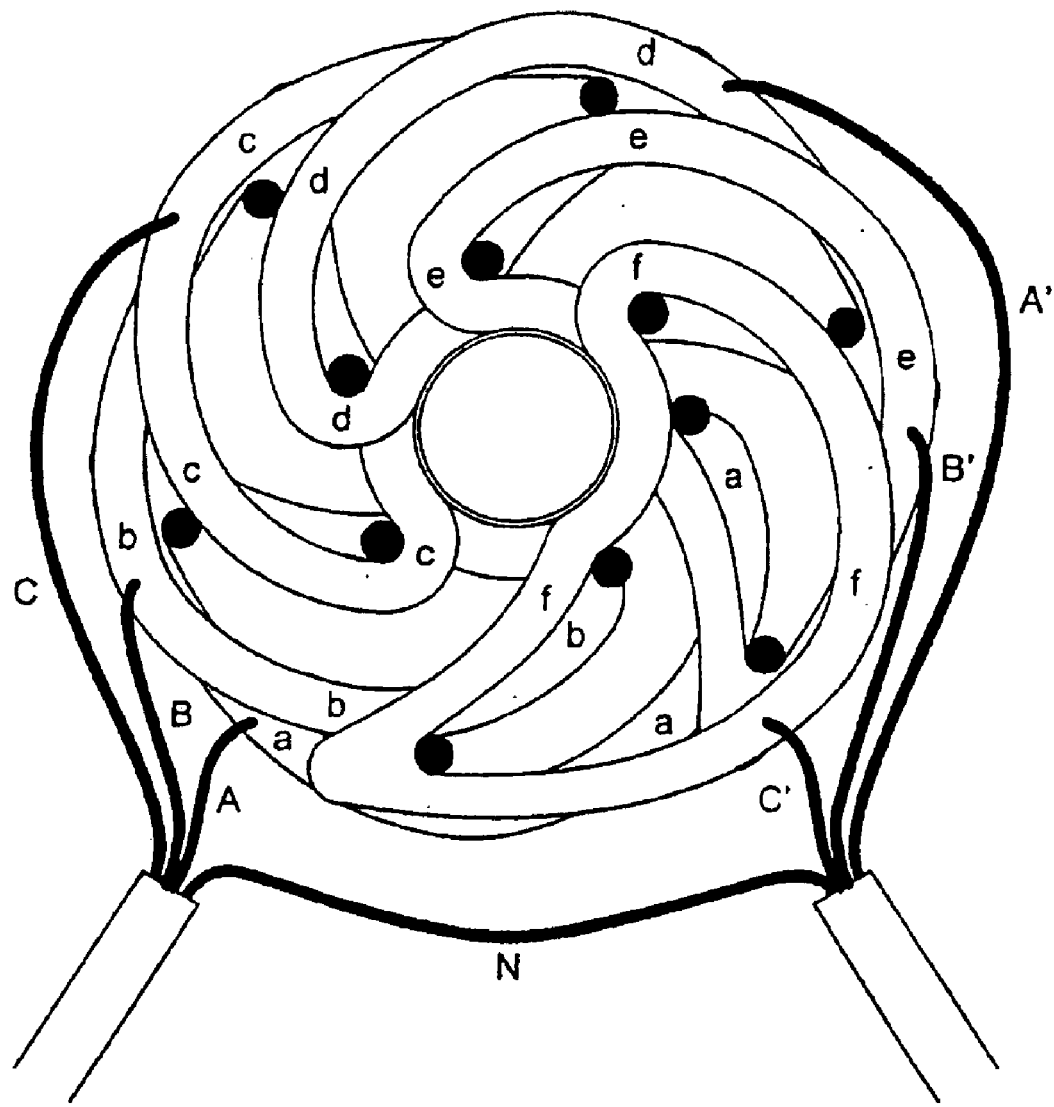

Yet another three phase winding topology, depicted in FIG. 5C, uses two coils per phase for each of the body and cover windings, and connects the coil sides by azimuthal end-windings as is standard motor winding practice. The coils are shown tilted to approximately follow the blade curvature, which can increase motor efficiency, especially for the phase energising strategy to be described below in which only one phase is energised at a time. The winding construction can be simplified by laying the coils around pins protruding from a temporary former, the pins shown as dots in 2 rings of 6 pins each in FIG. 5C. The coils are labelled alphabetically in the order in which they would be layed, coils a and d for phase A, b and e for phase B, and c and f for phase C. Instead of or as well as pins, the coil locations could be defined by thin fins, running between the pins in FIG. 5C, along the boundary between the coils. The coil connections depicted in FIG. 5C are those appropriate for the winding nearest the motor terminals for the case of series connection, with the optional lead from the neutral point on the other winding included.

The winding topologies depicted in FIGS. 5B and C allow the possibility of higher motor efficiency but only if significantly higher coil mass is allowed, and since option FIG. 5A is more compact and simpler to manufacture, it is the preferred option. Material ribs between the coils of option FIG. 5A can be used to stiffen the housing.

Multi-stranded flexible conductors within a suitable biocompatible cable can be used to connect the motor windings to a motor controller. The energisation of the three phases can be performed by a standard sensorless controller, in which two out of six semiconducting switches in a three phase bridge are turned on at any one time. Alternatively, because of the relatively small fraction of the impeller cross-section occupied by magnets, it may be slightly more efficient to only activate one of the three phases at a time, and to return the current by a conductor from the neutral point in the motor. Careful attention must be paid to ensure that the integrity of all conductors and connections is failsafe.

In one embodiment, the two housing components 3 and 4 are made by injection moulding from non-electrically conducting plastic materials such as Lexan polycarbonate plastic. Alternatively the housing components can be made from ceramics. The windings and yokes are ideally encapsulated within the housing during fabrication moulding. In this way, the separation between the winding and the magnets is minimised, increasing the motor efficiency, and the housing is thick, increasing its mechanical stiffness. Alternatively, the windings can be positioned outside the housing, of thickness at least around 2 mm for sufficient stiffness.

If the housing material plastic is hygroscopic or if the windings are outside the housing, it may be necessary to first enclose the windings and yoke in a very thin impermeable shell. Ideally the shell should be non-conducting (such as ceramic or plastic). Titanium of around 0.1 mm to 0.2 mm thickness gives sufficiently low eddy losses. Encapsulation within such a shell is needed to prevent winding movement.

Alternatively, and in a particularly preferred embodiment the housing components 3 and 4 may be made from a biocompatible metallic material of low electrical conductivity, such as Ti-6Al-4V. To minimise the eddy current loss, the material must be as thin as possible, e.g. 0.1 mm to 0.5 mm, wherever the material experiences high alternating magnetic flux densities, such as between the coils and the housing inner surfaces 10 and 11.

The combining of the motor and bearing components into the impeller in the preferred embodiment provides several key advantages. The rotor consequently has very simple form, with the only cost of the bearing being tight manufacturing tolerances. The rotor mass is very low, minimising the bearing force needed to overcome weight. Also, with the bearings and the motor in the same region of the rotor, the bearings forces are smaller than if they had to provide a torque to support magnets at an extremity of the rotor.

A disadvantage of the combination of functions in the impeller is that its design is a coupled problem. The optimisation should ideally link the fluid dynamics, magnetics and bearing thrust calculations. In reality, the blade thickness can be first roughly sized to give adequate motor efficiency and sufficient bearing forces with a safety margin. Fortuitously, both requirements are met for four blades of approximate average circumferential thickness 6 mm or more. The housing, blade, and support shapes can then be designed using computational fluid dynamics, maintaining the above minimum average blade thickness. Finally the motor stator, i.e. winding and yoke, can be optimised for maximum motor efficiency.

Figure 6:
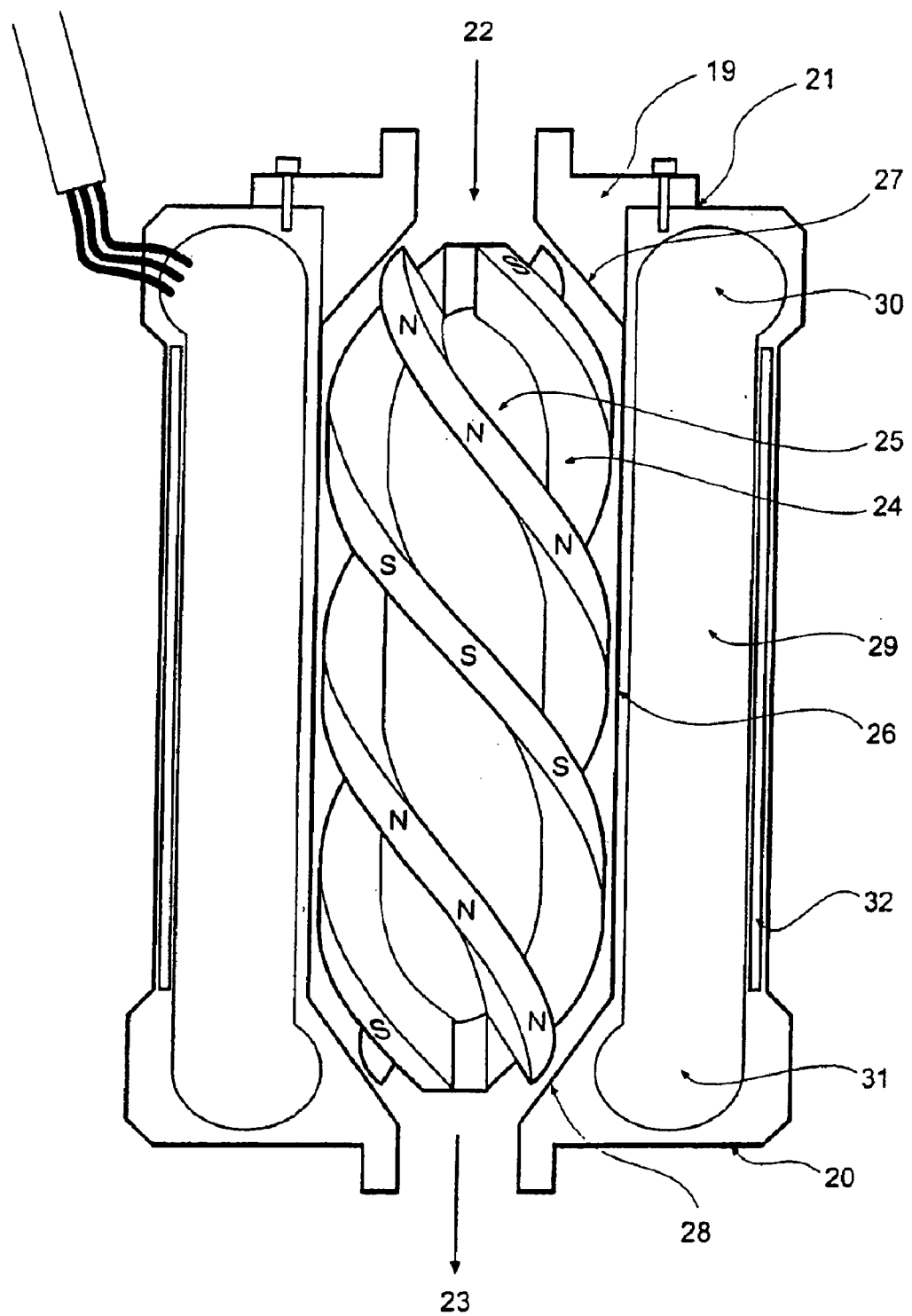
FIG. 6 is a diagrammatic cross-sectional view of an alternative embodiment of the invention as an axial pump.

FIG. 6 depicts an alternative embodiment of the invention as an axial pump. The pump housing is made of two parts, a front part 19 and a back part 20, joined for example at 21. The pump has an axial inlet 22 and axial outlet 23. The impeller comprises only blades 24 mounted on a support cylinder 25 of reducing radius at each end. An important feature of this embodiment is that the blade bearing surfaces are tapered to generate hydrodynamic thrust forces which suspend the impeller. These forces could be used for radial suspension alone from the straight section 26 of the housing, with some alternative means used for axial suspension, such as stable axial magnetic forces or a conventional tapered-land type hydrodynamic thrust bearing. FIG. 6 proposes a design which uses the tapered blade bearing surfaces to also provide an axial hydrodynamic bearing. The housing is made with a reducing radius at its ends to form a front face 27 and a back face 28 from which the axial thrusts can suspend the motor axially. Magnets are embedded in the blades with blades having alternating polarity and four blades being recommended. Iron in the outer radius of the support cylinder 25 can be used to increase the magnet flux density. Alternatively, the magnets could be housed in the support cylinder and iron could be used in the blades. A slotless helical winding 29 is recommended, with outward bending end-windings 30 at one end to enable insertion of the impeller and inward bending windings 31 at the other end to enable insertion of the winding into a cylindrical magnetic yoke 32. The winding can be encapsulated in the back housing part 20.

Third Embodiment

With reference to FIGS. 7 to 15 inclusive there is shown a further preferred embodiment of the pump assembly 200.

Figure 7:
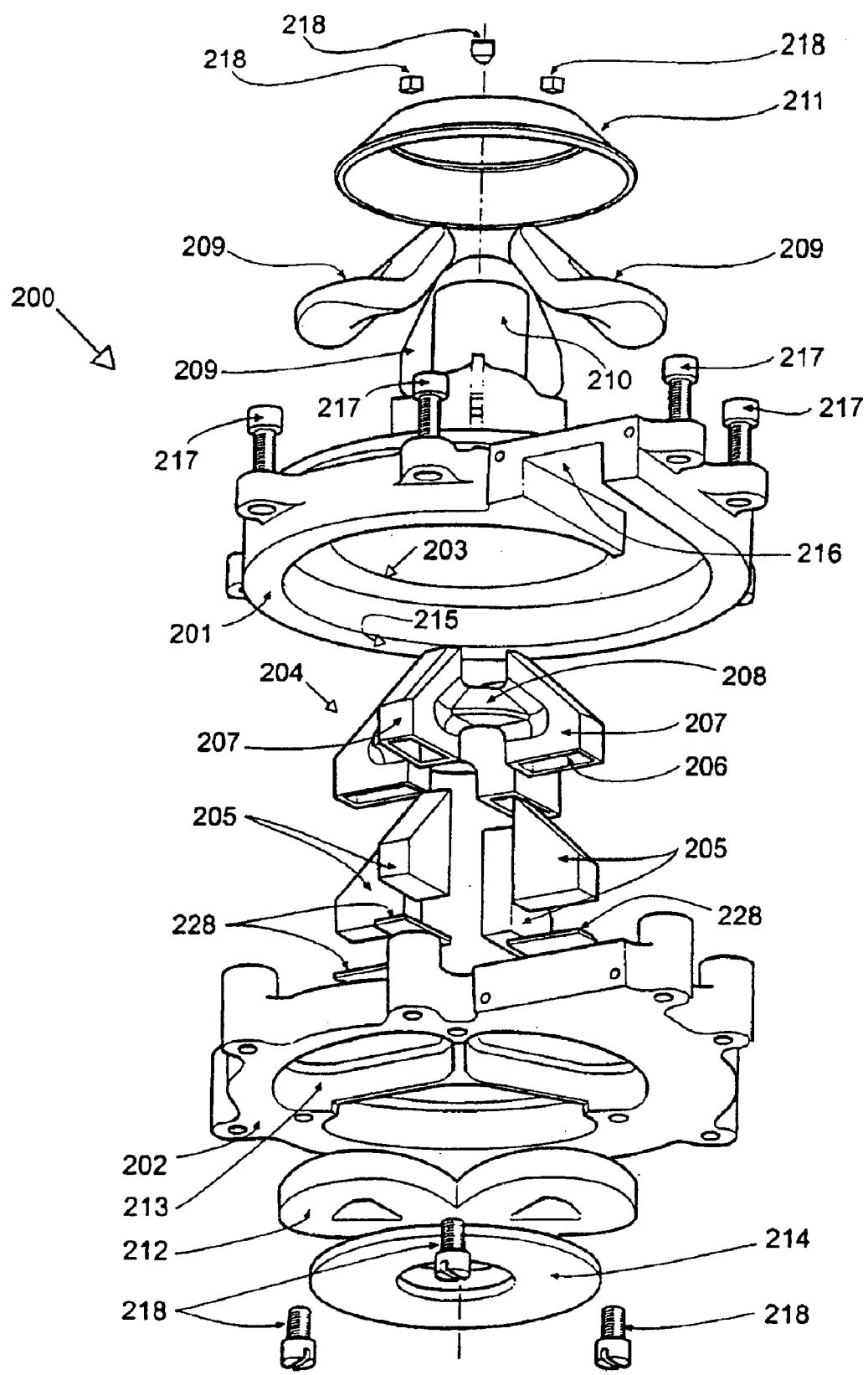
FIG. 7 is an exploded, perspective view of a centrifugal pump assembly according to a further embodiment of the invention.

With particular reference initially to FIG. 7 the pump assembly 200 comprises a housing body 201 adapted for bolted connection to a housing cover 202 and so as to define a centrifugal pump cavity 203 therewithin.

The cavity 203 houses an impeller 204 adapted to receive magnets 205 within cavities 206 defined within blades 207. As for the first embodiment the blades 207 are supported from a support 208.

Exterior to the cavity 203 but forming part of the pump assembly 200 there is located a body winding 209 symmetrically mounted around inlet 210 and housed between the housing body 201 and a body yoke 211.

Also forming part of the pump assembly 200 and also mounted external to pump cavity 203 is cover winding 212 located within winding cavity 213 which, in turn, is located within housing cover 202 and closed by cover yoke 214.

Figure 12:
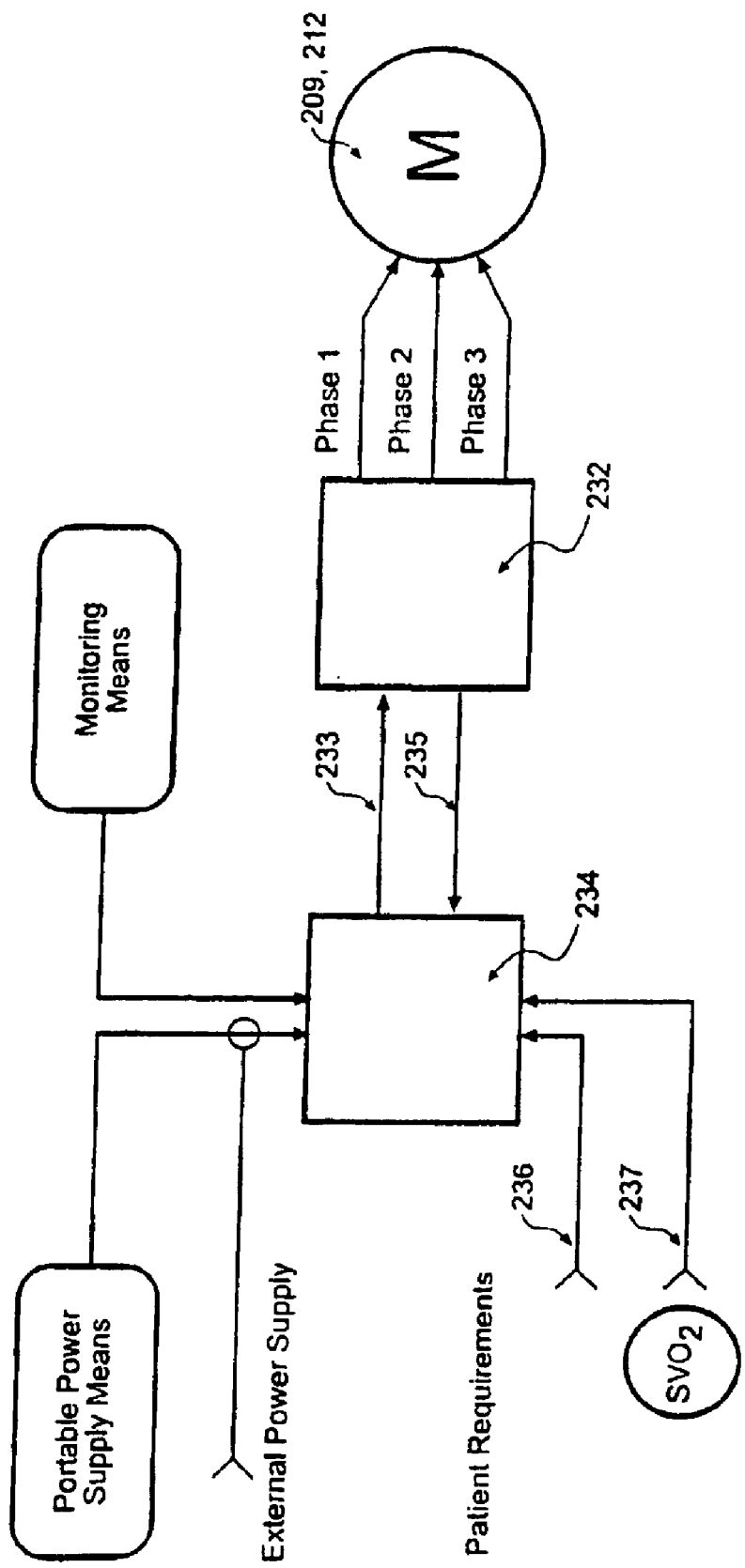
FIG. 12 is a block diagram of an electronic driver circuit for the pump assembly of FIG. 7.

The windings 212 and 209 are supplied from the electronic controller of FIG. 12 as for the first embodiment the windings are arranged to receive a three phase electrical supply and so as to set up a rotating magnetic field within cavity 203 which exerts a torque on magnets 205 within the impeller 204 so as to urge the impeller 204 to rotate substantially about central axis TT of cavity 203 and in line with the longitudinal axis of inlet 210. The impeller 204 is caused to rotate so as to urge fluid (in this case blood) around volute 215 and through outlet 216.

The assembly is bolted together in the manner indicated by screws 217. The yokes 211, 214 are held in place by fasteners 218. Alternatively, press fitting is possible provided sufficient integrity of seal can be maintained.

In a particularly preferred form the components are welded together.

Figure 8:
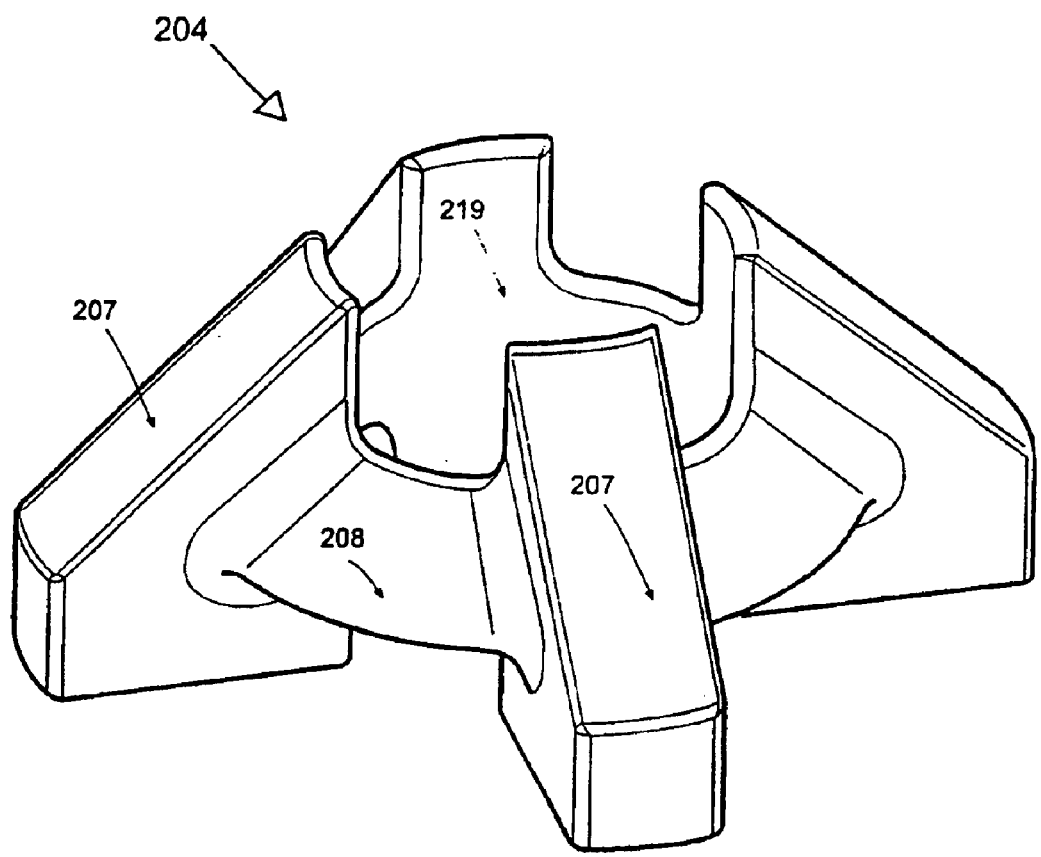
FIG. 8 is a perspective view of the impeller of the assembly of FIG. 7.

FIG. 8 shows the impeller 204 of this embodiment and clearly shows the support 208 from which the blades 207 extend. The axial cavity 219 which is arranged, in use, to be aligned with the longitudinal axis of inlet 210 and through which blood is received for urging by blades 207 is clearly visible.

Figure 9:
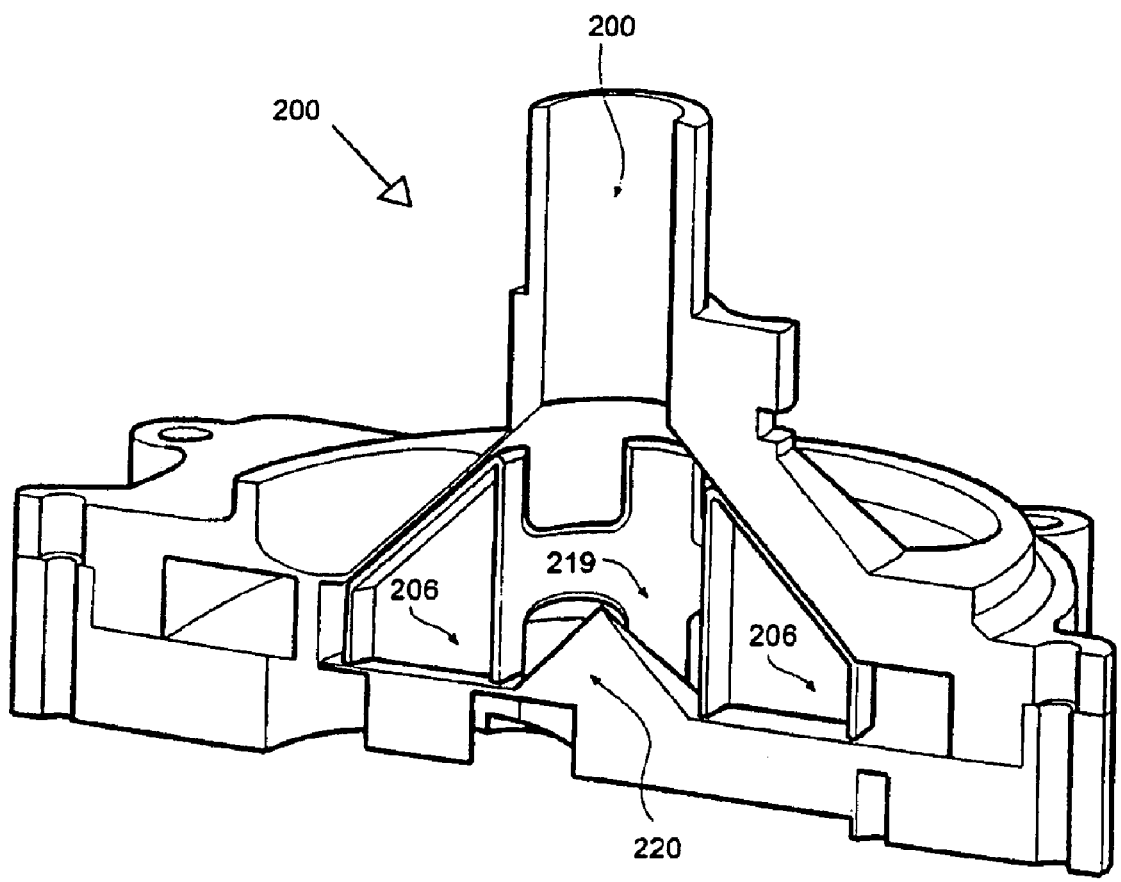
FIG. 9 is a perspective, cut away view of the impeller of FIG. 8 within the pump assembly of FIG. 7.

The cutaway view of FIG. 9 shows the axial cavity 219 and also the magnet cavities 206 located within each blade 207. The support structure 220 extending from housing cover 202 aligned with the axis of inlet 210 and axial cavity 219 of impeller 204 is also shown.

Figure 10:
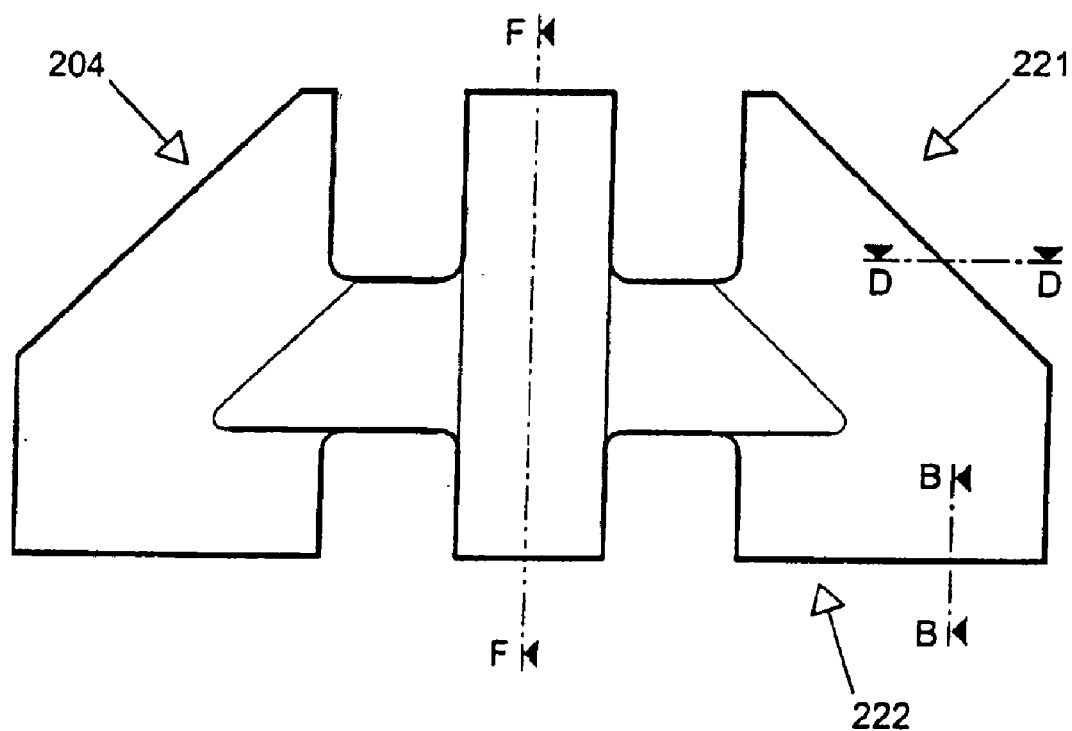
FIG. 10 is a side section indicative view of the impeller of FIG. 8.
Figure 11:
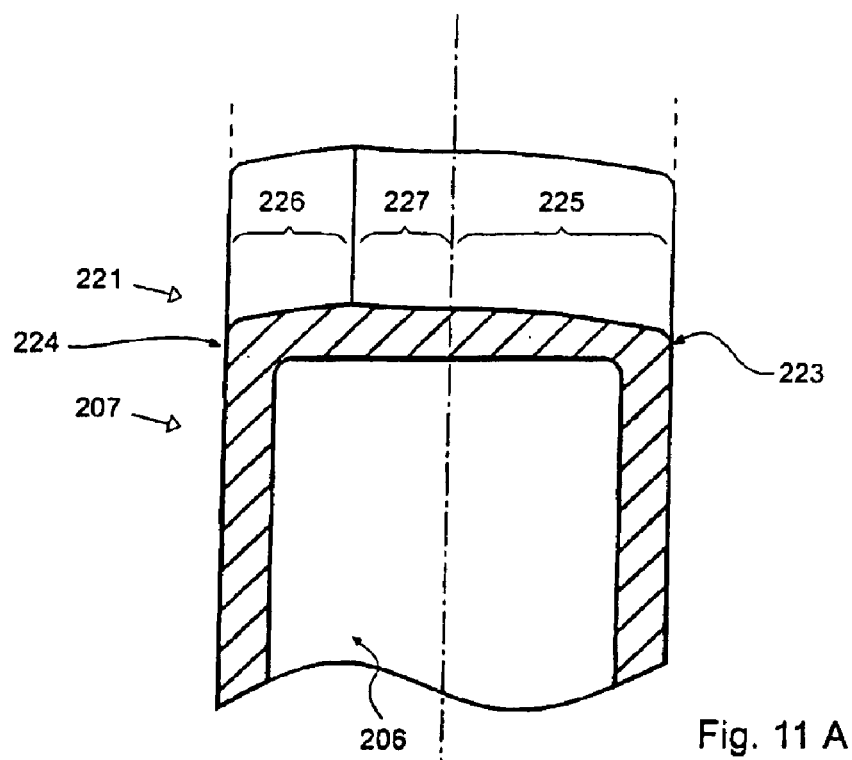
FIG. 11 is a detailed view in side section of blade portions of the impeller of FIG. 10.
Figure 11:
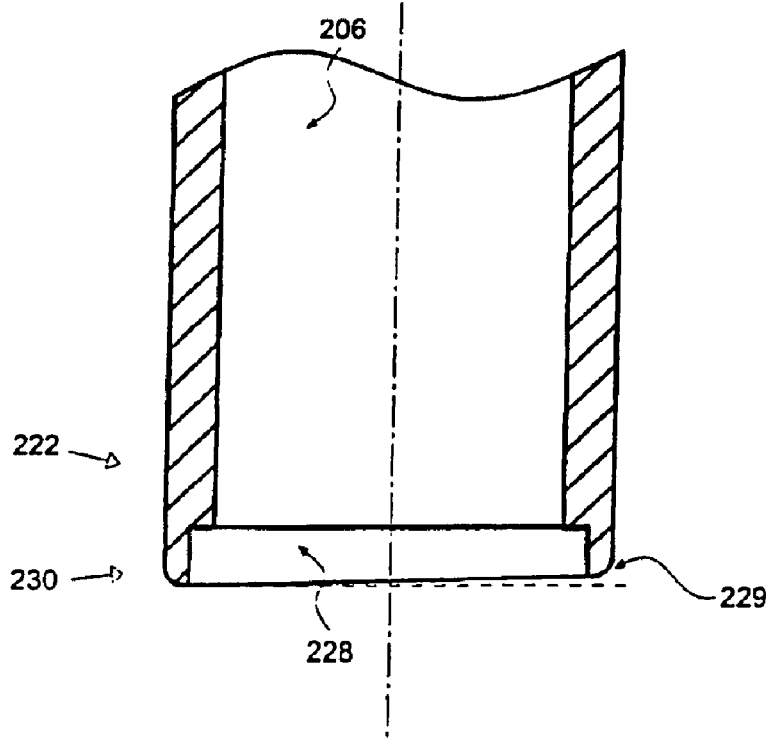

FIG. 10 is a side section, indicative view of the impeller 204 defining the orientations of central axis FF, top taper face DD and bottom taper face BB, which tapers are illustrated in FIG. 11 in side section view.

FIG. 11A is a section of a blade 207 of impeller 204 taken through plane DD as defined in FIG. 10 and shows the top edge surface 221 to be profiled from a leading edge 223 to a trailing edge 224 as follows: central portion 227 comprises an ellipse with centre on the dashed midline having a semi-major axis of radius 113 mm and a semi-minor axis of radius 80 mm and then followed by leading conical surface 225 and trailing conical surface 226 on either side thereof as illustrated in FIG. 11A. The leading surface 225 has radius 0.05 mm less than the trailing surface 226. This prescription is for a taper which can be achieved by a grinding wheel, but many alternative prescriptions could be devised to give a taper of similar utility.

The leading edge 223 is radiused as illustrated.

FIG. 11B illustrates in cross-section the bottom edge face 222 of blade 207 cut along plane BB of FIG. 10.

The bottom face includes cap 228 utilised for sealing magnet 205 within cavity 206.

In this instance substantially the entire face comprises a straight taper with a radius of 0.05 mm at leading edge 229 and a radius of 0.25 mm at trailing edge 230.

The blade 207 is 6.0 mm in width excluding the radii at either end.

FIG. 12 comprises a block diagram of the electrical controller suitable for driving the pump assembly 200 and comprises a three phase commutation controller 232 adapted to drive the windings 209, 212 of the pump assembly. The commutation controller 232 determines relative phase and frequency values for driving the windings with reference to set point speed input 233 derived from physiological controller 234 which, in turn, receives control inputs 235 comprising motor current input and motor speed (derived from the commutation controller 232). Whilst not preferred, patient blood flow 236, and venous oxygen saturation 237 can be input as well. The pump blood flow can be approximately inferred from the motor speed and current via curve-fitted formulae.

Figure 13:
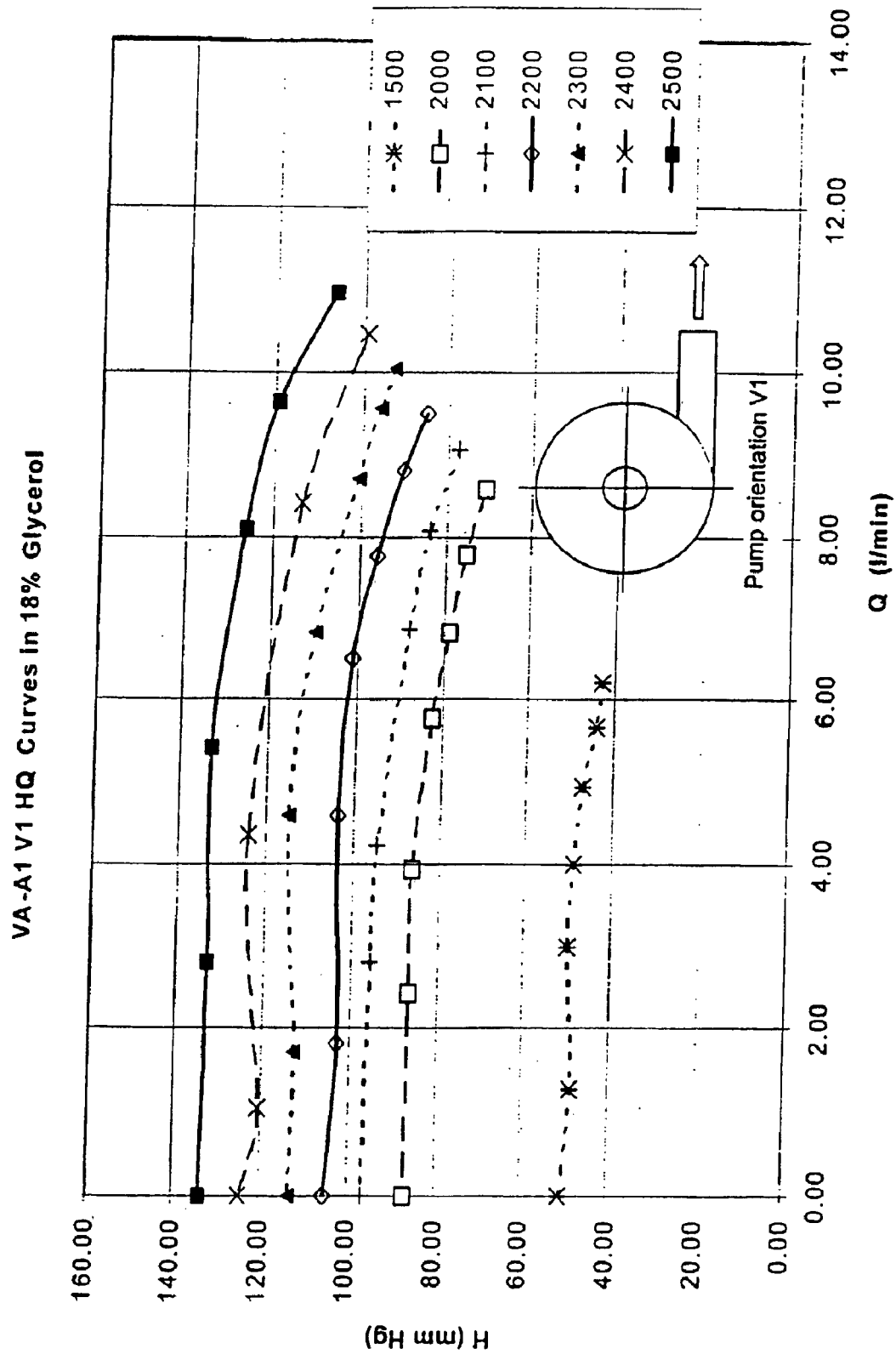
FIG. 13 is a graph of head versus flow for the pump assembly of FIG. 7.

FIG. 13 is a graph of pressure against flow for the pump assembly 200 where the fluid pumped is 18% glycerol for impeller rotation velocity over the range 1500 RPM to 2500 RPM. The 18% glycerol liquid is believed to be a good analogue for blood under certain circumstances, for example in the housing gap.

Figure 14:
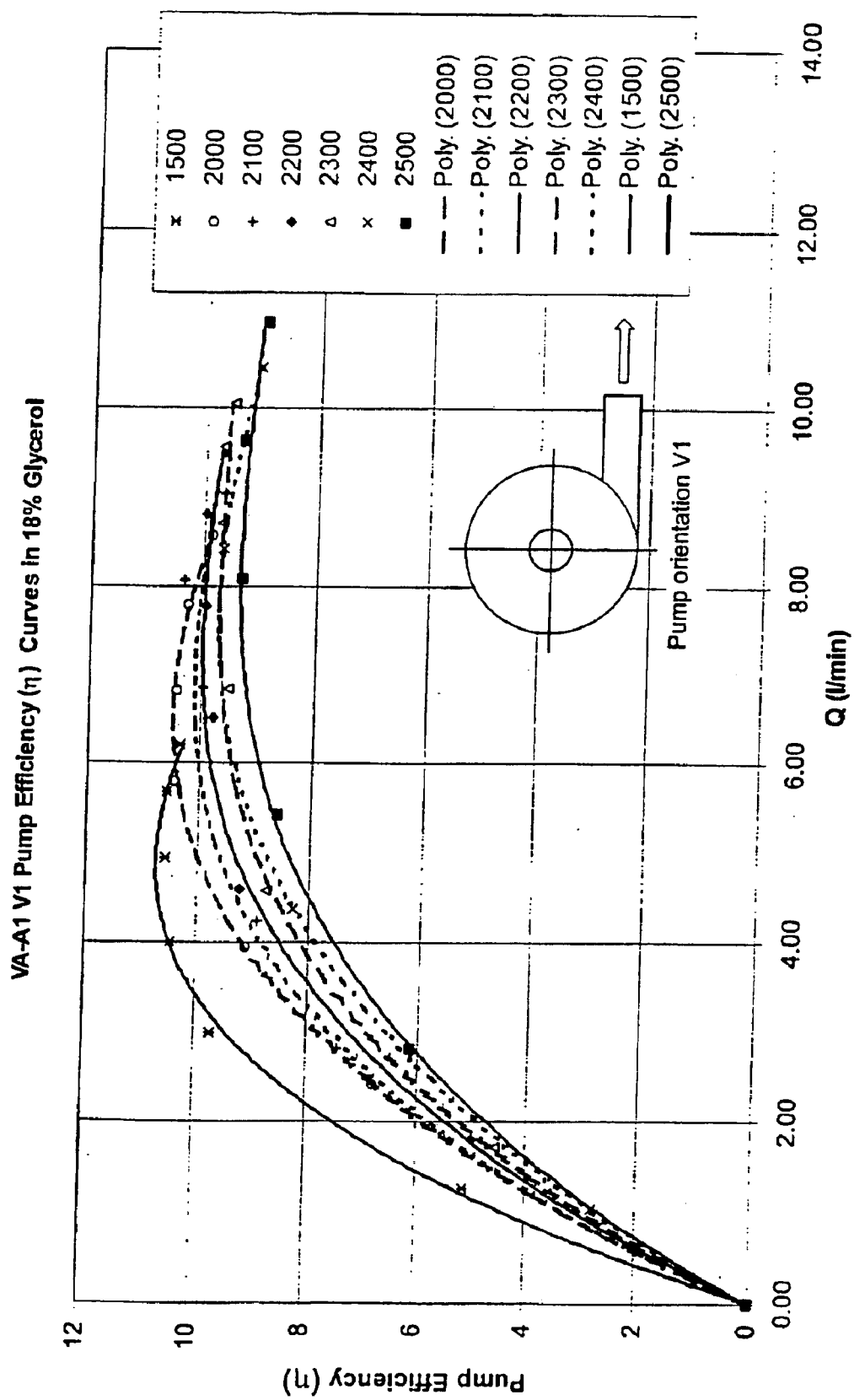
FIG. 14 is a graph of pump efficiency versus flow for the pump assembly of FIG. 7.

FIG. 14 graphs pump efficiency against flow for the same fluid over the same speed ranges as for FIG. 13.

Figure 15:
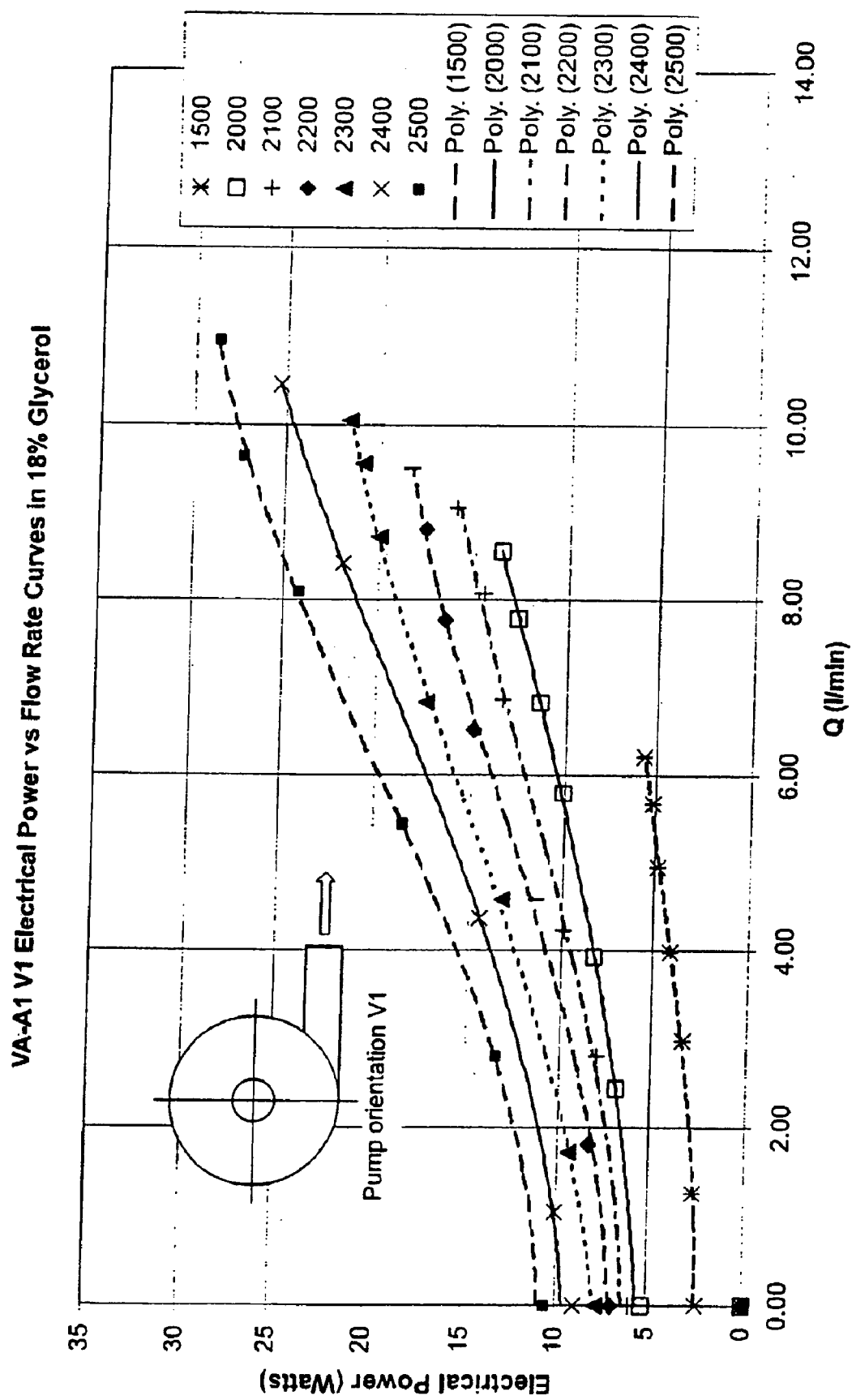
FIG. 15 is a graph of electrical power consumption versus flow for the pump assembly of FIG. 7.
Figure 16:
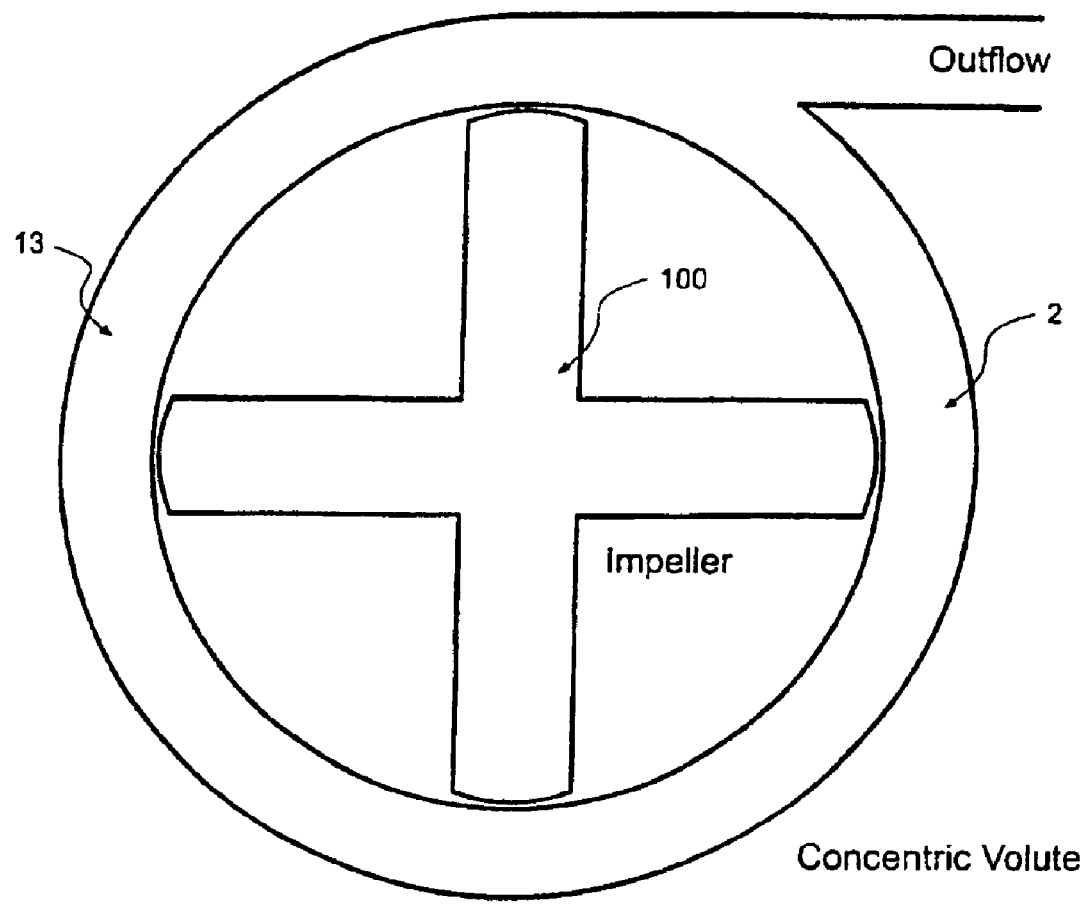
FIG. 16 is a plan, section view of the pump assembly showing a volute arrangement according to a preferred embodiment.

FIG. 15 is a graph of electrical power consumption against flow for the same fluid over the same speed ranges as for FIG. 13.

The common theme running through the first, second and third embodiments described thus far is the inclusion in the impeller of a taper or other deformed surface which, in use, moves relative to the adjacent housing wall thereby to cause a restriction with respect to the line of movement of the taper or deformity thereby to generate thrust upon the impeller which includes a component substantially normal to the line of movement of the surface and also normal to the adjacent internal pump wall with respect to which the restriction is defined for fluid located therebetween.

In order to provide both radial and axial direction control at least one set of surfaces must be angled with respect to the longitudinal axis of the impeller (preferably at approximately 45° thereto) thereby to generate or resolve opposed radial forces and an axial force which can be balanced by a corresponding axial force generated by at least one other tapered or deformed surface located elsewhere on the impeller.

In the forms thus far described top surfaces of the blades 8, 207 are angled at approximately 45° with respect to the longitudinal axis of the impeller 100, 204 and arranged for rotation with respect to the internal walls of a similarly angled conical pump housing. The top surfaces of the blades are deformed so as to create the necessary restriction in the gap between the top surfaces of the blades and the internal walls of the conical pump housing thereby to generate a thrust which can be resolved to both radial and axial components.

In the examples thus far the bottom faces of the blades 8, 207 comprise surfaces substantially lying in a plane at right angles to the axis of rotation of the impeller and, with their deformities define a gap with respect to a lower inside face of the pump housing against which a substantially only axial thrust is generated.

Other arrangements are possible which will also, relying on these principles, provide the necessary balanced radial and axial forces. Such arrangements can include a double support arrangement where the conical top surface of the blades is mirrored in a corresponding bottom conical surface. The only concern with this arrangement is the increased depth of pump which can be a problem for in vivo applications where size minimisation is an important criteria.

Fourth Embodiment

Figure 18:
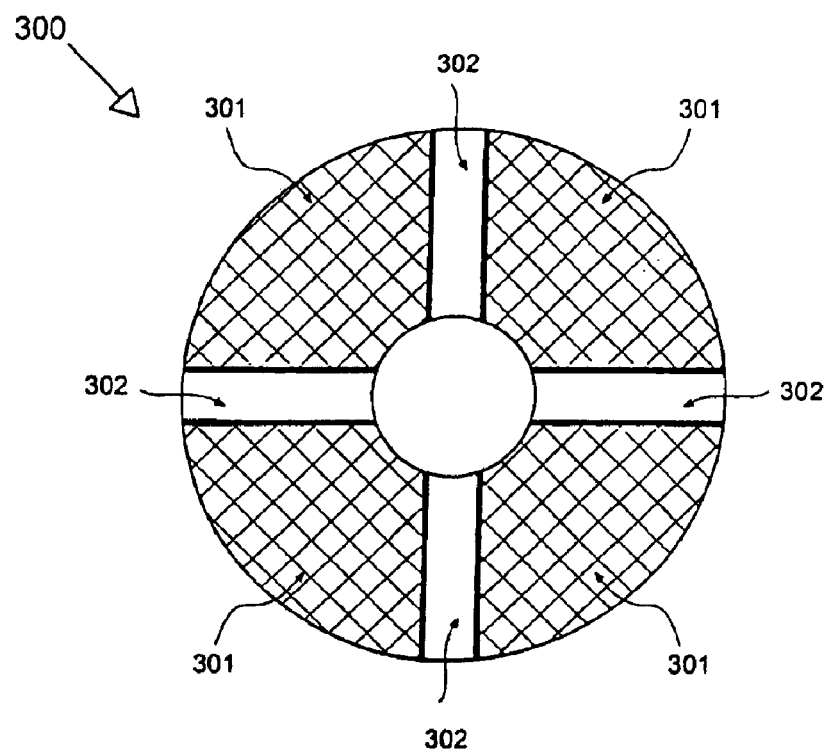
FIG. 18 is a plan view of an impeller according to a further embodiment of the invention.

With reference to FIG. 18 a further embodiment of the invention is illustrated comprising a plan view of the impeller 300 forming part of a "channel" pump. In this embodiment the blades 301 have been widened relative to the blades 207 of the third embodiment to the point where they are almost sector-shaped and the flow gaps between adjacent blades 301, as a result, take the form of a channel 302, all in communication with axial cavity 303.

Figure 19:
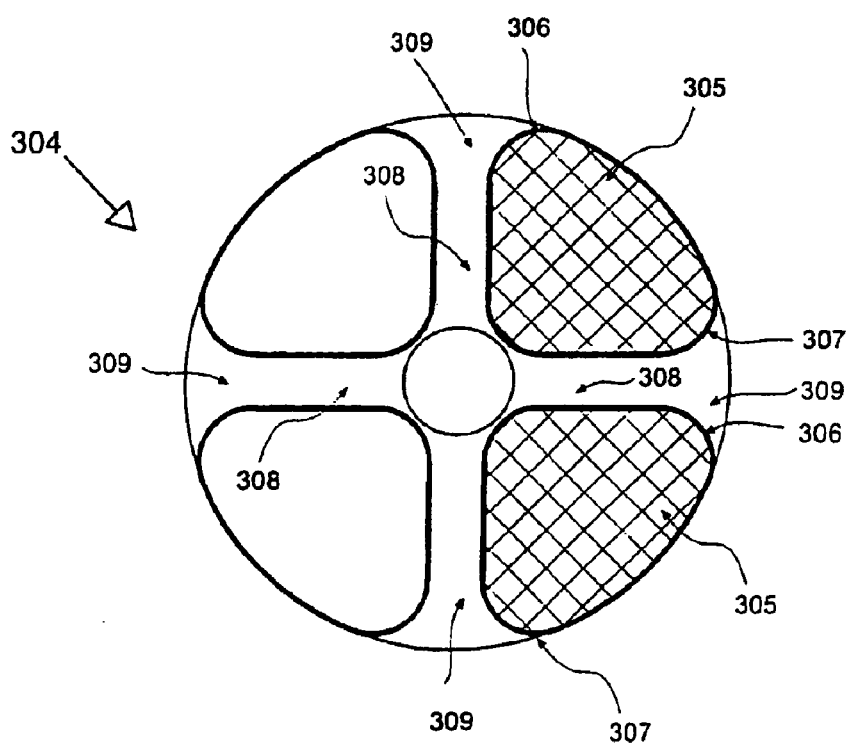
FIG. 19 is a plan view of an impeller according to a further embodiment of the invention.

A further modification of this arrangement is illustrated in FIG. 19 wherein impeller 304 includes sector-shaped blades 305 having curved leading and trailing portions 306, 307 respectively thereby defining channels 308 having fluted exit portions 309.

As with the first and second embodiments the radial and axial hydrodynamic forces are generated by appropriate profiling of the top and bottom faces of the blades 301, 305 (not shown in FIGS. 18 and 19).

Figure 20:
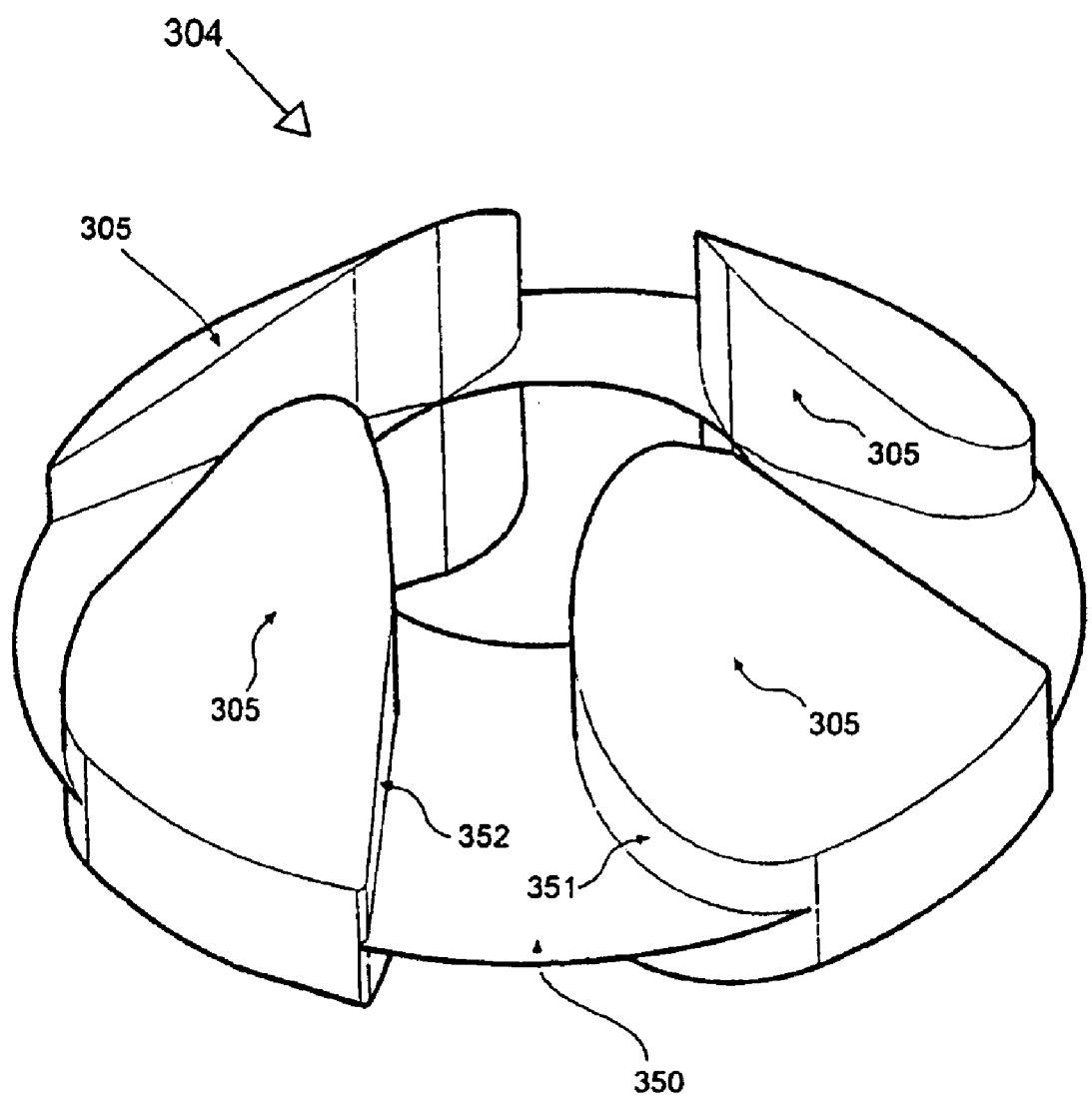
FIG. 20 is a perspective view of an impeller according to a further embodiment of the invention.

FIG. 20 illustrates a perspective view of an impeller 304 which follows the theme of the impeller arrangement of FIGS. 18 and 19 in perspective view and where like parts are numbered as for FIG. 19. In this case the four blades 305 are joined at mid-portions thereof by a blade support in the form of a conical rim 350 and have face portions which are shaped so as to have an increased curvature on the pressure face 351 thereof compared with the suction face 352.

Fifth Embodiment

Figure 21:
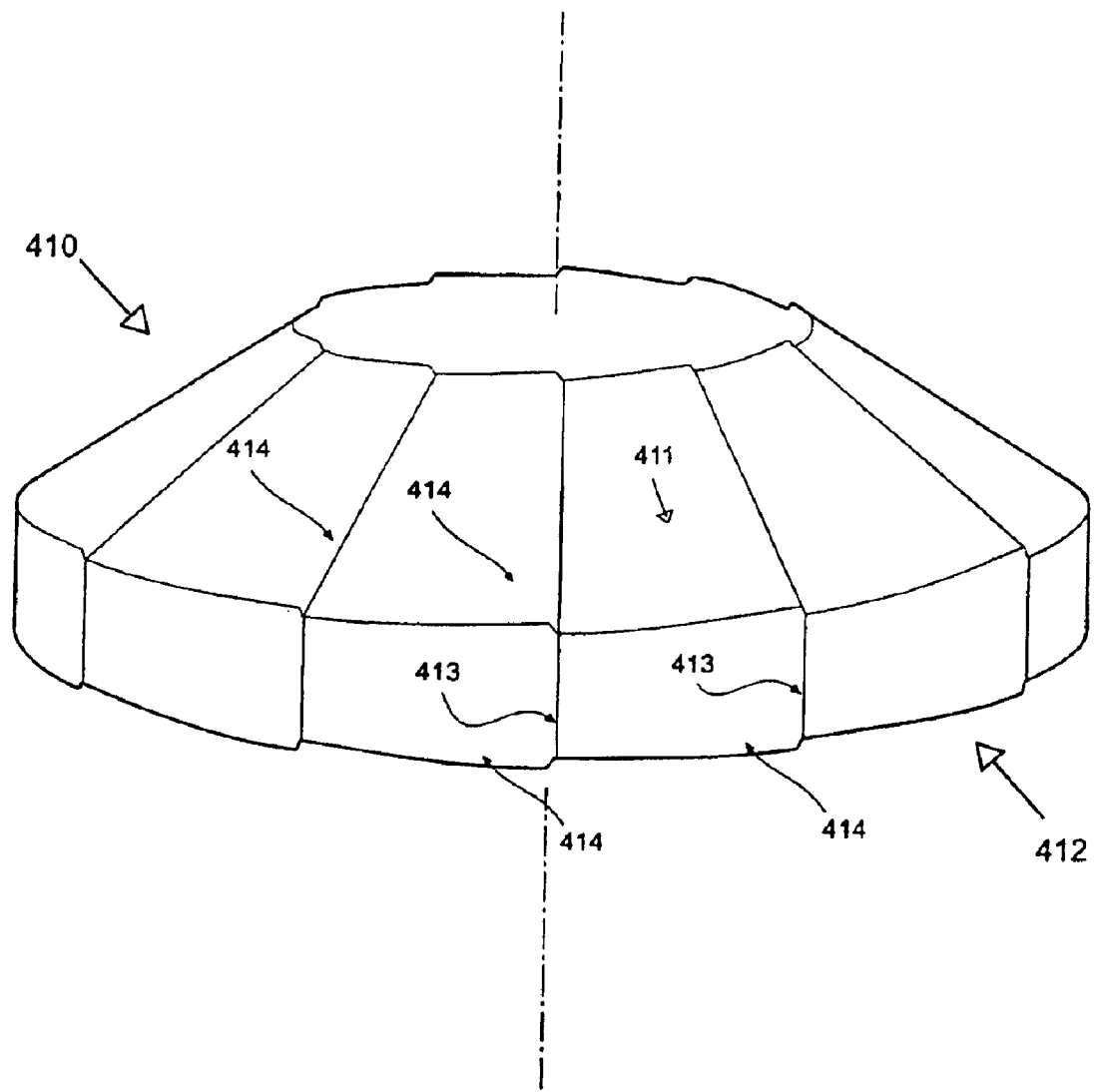
FIG. 21 is a perspective view of an impeller according to yet a further embodiment of the invention.

A fifth embodiment of a pump assembly according to the invention comprises an impeller 410 as illustrated in FIG. 21 where, conceptually, the upper and lower surfaces of the blades of previous embodiments are interconnected by a top shroud 411 and a bottom shroud 412. In this embodiment the blades 413 can be reduced to a very small width as the hydrodynamic behaviour imparted by their surfaces in previous embodiments is now given effect by the profiling of the shrouds 411, 412 each of which, in this instance, comprise a series of smoothed wedges 414 with the leading edge of one wedge directly interconnected to the trailing edge of the preceding wedge.

As for previous embodiments the top shroud 411 is of overall conical shape thereby to impart both radial and axial thrust forces whilst the bottom shroud 412 is substantially planar thereby to impart substantially only axial thrust forces.

It is to be understood that, whilst the example of FIG. 21 shows the surfaces of the shroud 411 angled at approximately 45° to the vertical, other inclinations are possible extending to an inclination of 0° to the vertical which is to say the impeller 410 can take the form of a cylinder with surface rippling or other deformations which impart the necessary hydrodynamic lift, in use.

Figure 22:
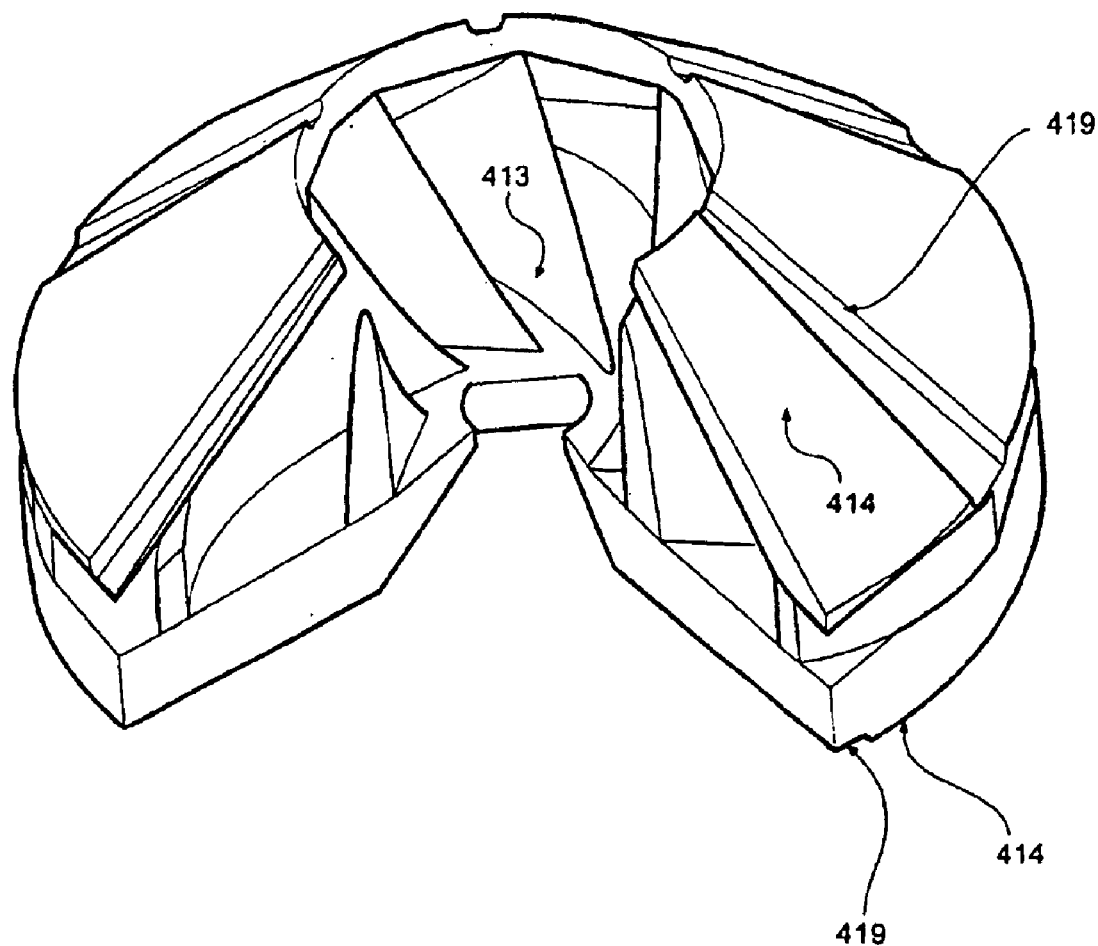
FIG. 22 is a perspective, partially cut away view of an impeller according to yet a further embodiment of the invention.
Figure 23:
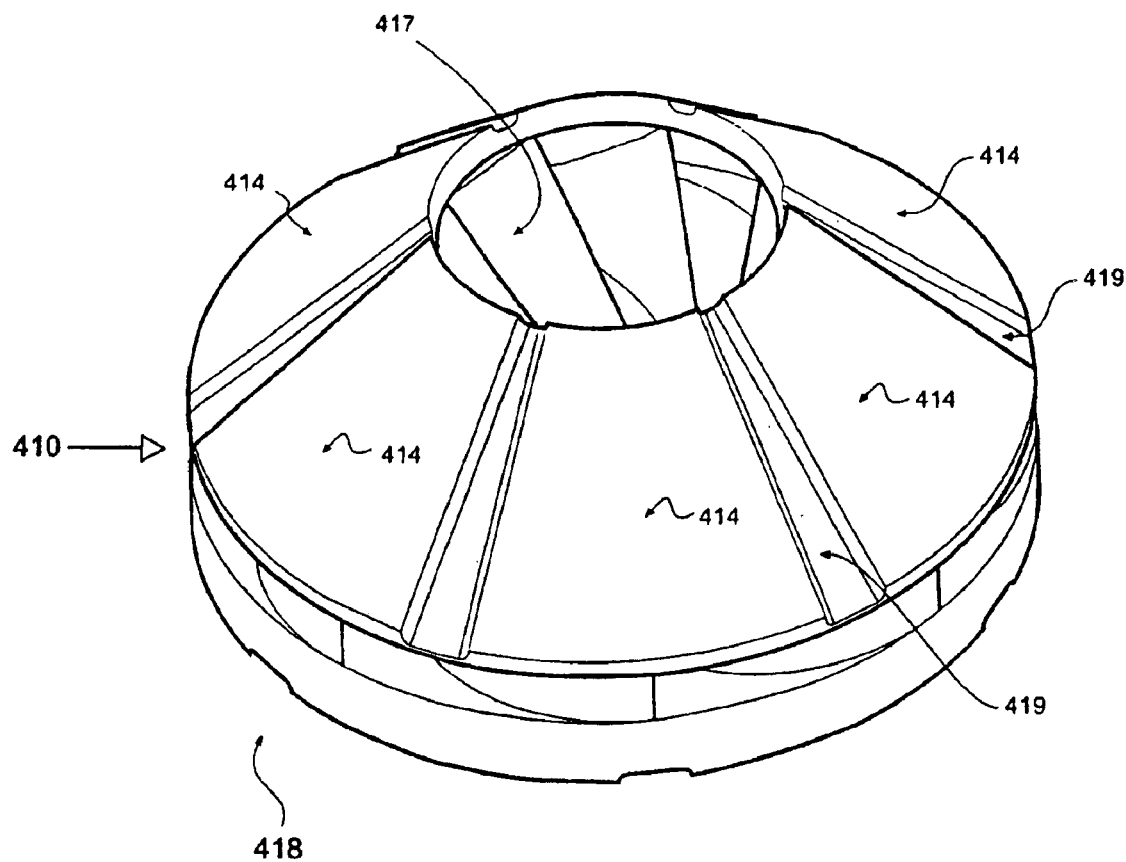
FIG. 23 is a top, perspective view of the impeller of FIG. 22.
Figure 24:
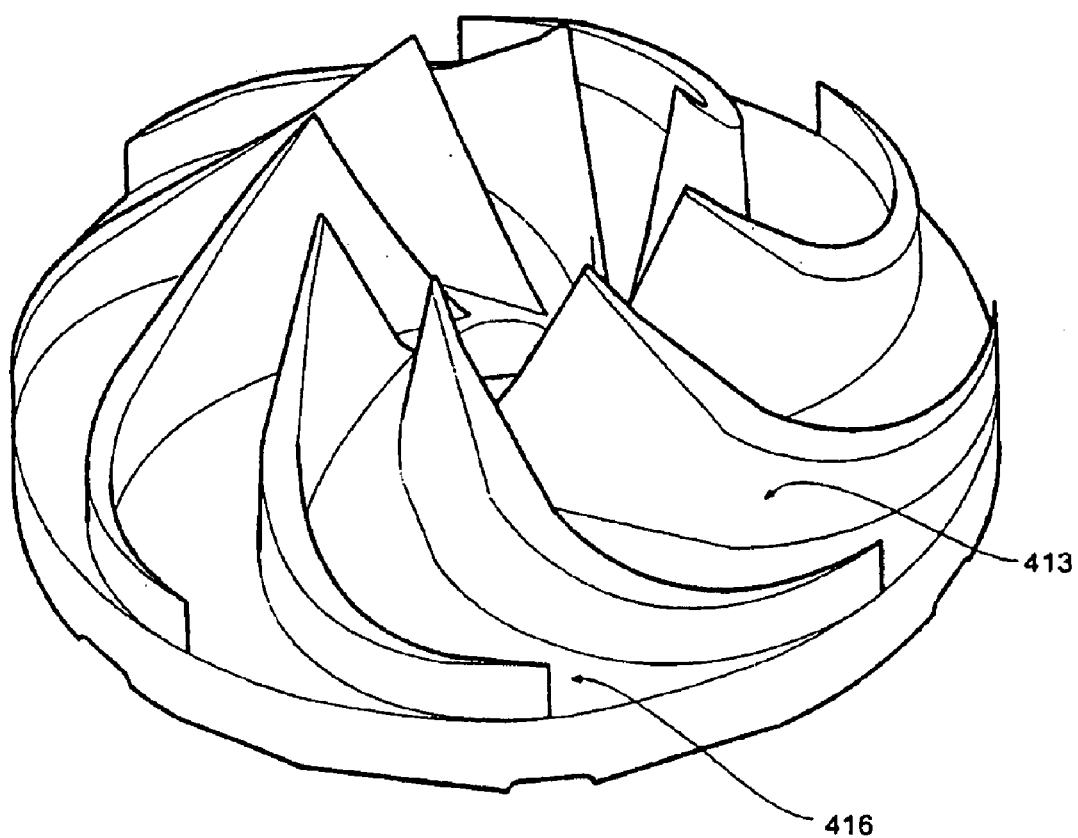
FIG. 24 is a perspective view of the impeller of FIG. 22 with its top shroud removed.

With reference to FIGS. 22 to 24 a specific example of the concept embodied in FIG. 21 is illustrated and wherein like components are numbered as for FIG. 21.

It will be observed that, with reference to FIG. 24, the blades 413 are thin compared to previous embodiments and, in this instance, are arcuate channels 416 therebetween which allow fluid communication from a centre volume 417 to the periphery 418 of the impeller 410.

In this arrangement it will be noted that the wedges 414 are separated one from the other on each shroud by channels 419. The channels extend radially down the shroud from the centre volume 417 to the periphery 418.

In such designs with thin blades, the magnets required for the driving torque can be contained within the top or bottom shroud or both, along with the optional soft magnetic yokes to increase motor efficiency.

A variation of this embodiment is to have the wedge profiling cut into the inner surfaces of the housing and have smooth shroud surfaces.

Sixth Embodiment

Figure 25:
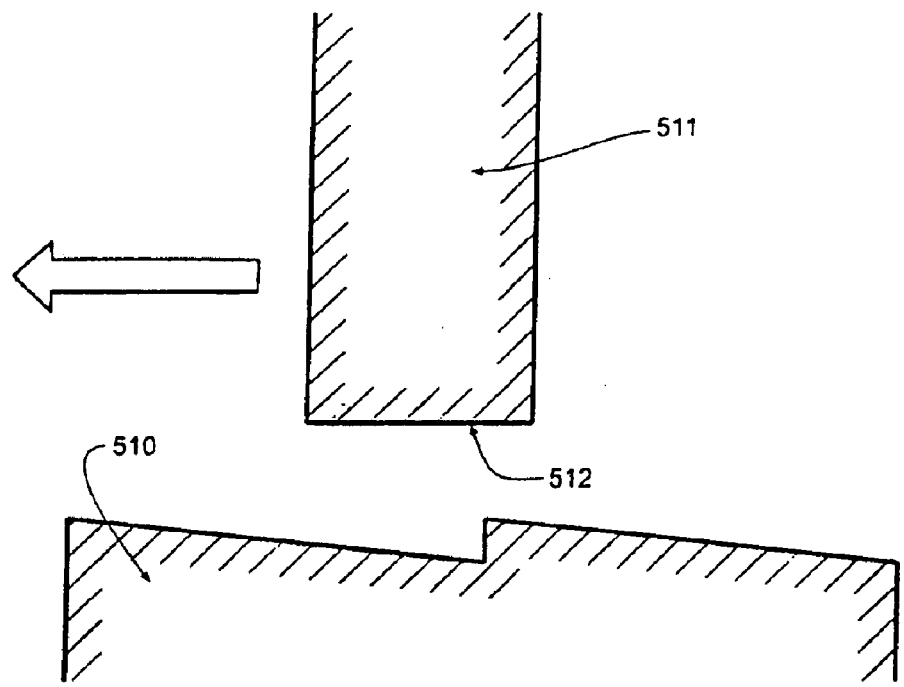
FIG. 25 illustrates an alternative embodiment wherein the deformed surface is located on the pump housing.

In contrast to the embodiments illustrated with respect to FIGS. 3A, 3B and 3C an arrangement is shown in FIG. 25 wherein the "deformed surface" comprises a stepped formation 510 forming part of an inner wall of the pump housing (not shown). In this instance the rotor including blade 511 includes a flat working surface 512 (and not having a deformed surface therein) which is adapted for relative movement in the direction of the arrow shown with respect to the stepped formation 510 thereby to generate hydrodynamic thrust therebetween.

Seventh Embodiment

Figure 26:
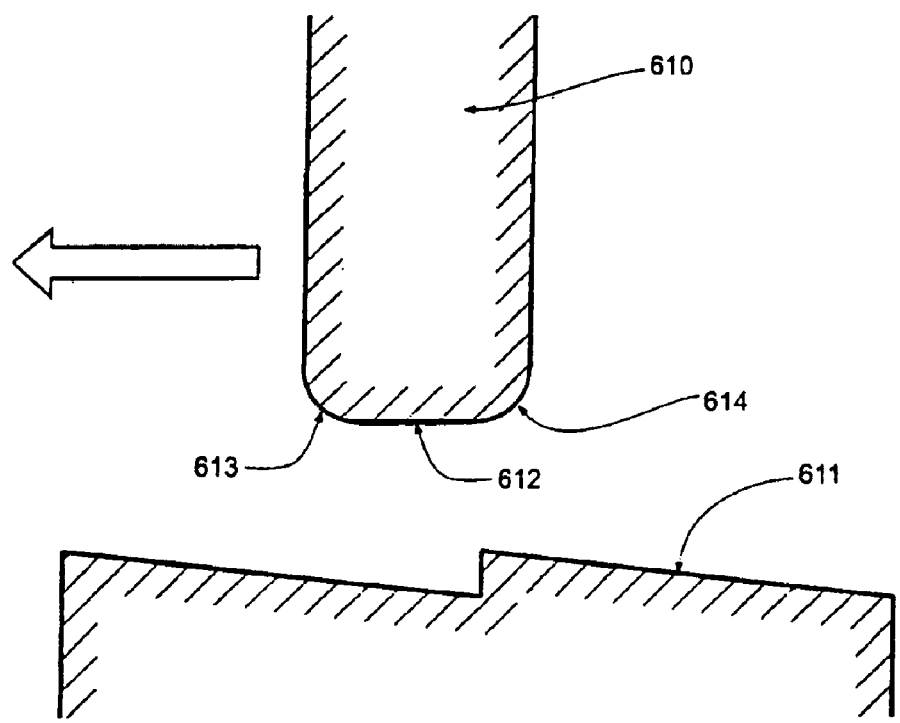
FIG. 26 illustrates a further embodiment wherein deformed surfaces are located both on the impeller and on the housing.

With reference to FIG. 26 there is shown an arrangement having facing deformed surfaces. The rotor blade 610 includes a deformed surface 612 at a working face thereof. In this instance the deformation comprises curved edge 613. Relative movement of the rotor blade 610 in the direction of the arrow with respect to deformed facing surface 611 forming part of the pump housing (not shown) causes relative hydrodynamic thrust therebetween.

The foregoing describes principles and examples of the present invention, and modifications, obvious to those skilled in the art, can be made thereto without departing from the scope and spirit of the invention.

Principles of Operation

Figure 27:
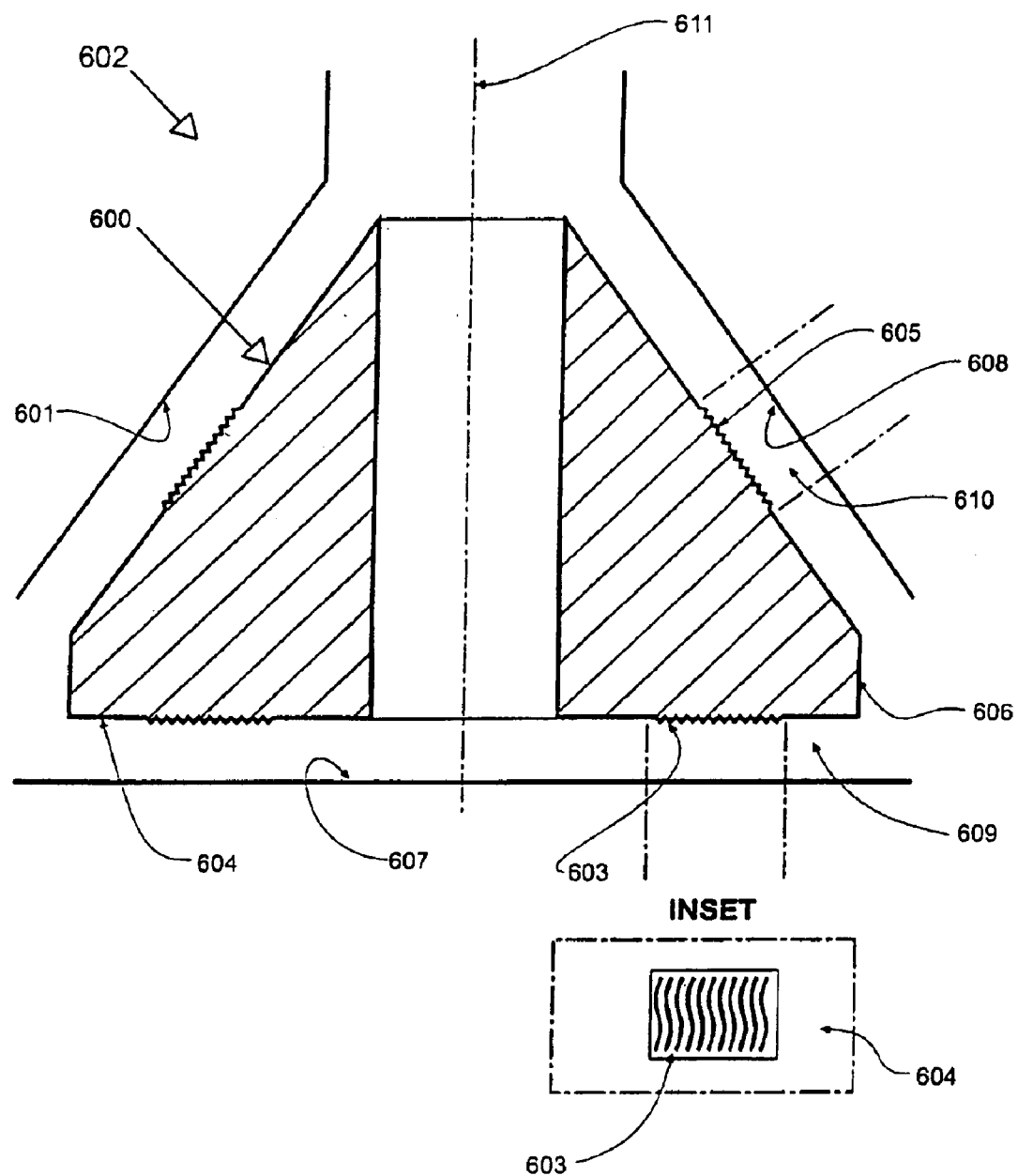
FIG. 27 illustrates diagrammatically the basis of operation of the "deformed surfaces" utilised for hydrodynamic suspension of embodiments of the invention.

With particular reference to FIG. 27 this specification describes the suspension of an impeller 600 within a pump housing 601 by the use of hydrodynamic forces. In this specification the suspension of the impeller 600 is performed dominantly which is to say exclusively by hydrodynamic forces.

The hydrodynamic forces are forces which are created by relative movement between two surfaces which have a fluid in the gap between the two surfaces. In the case of the use of the pump assembly 602 as a rotary blood pump the fluid is blood.

The hydrodynamic forces can arise during relative movement between two surfaces even where those surfaces are substantially entirely parallel to each other or non-deformed. However, in this specification, hydrodynamic forces are caused to arise during relative movement between two surfaces where at least one of the surfaces includes a "deformed surface".

In this specification "deformed surface" means a surface which includes an irregularity relative to a surface which it faces such that, when the surface moves in a predetermined direction relative to the surface which it faces the fluid located in the gap therebetween experiences a change in relative distance between the surfaces along the line of movement thereby to cause a hydrodynamic force to arise therebetween in the form of a thrust force including at least a component substantially normal to the plane of the gap defined at any given point between the facing surfaces.

In the example of FIG. 27 there is a first deformed surface 603 forming at least part of a first face 604 of impeller 600 and a second deformed surface 605 on a second face 606 of the impeller 600.

The inset of FIG. 27 illustrates conceptually how the first deformed surface 603 may form only part of the first face 604.

The first deformed surface 603 faces first inner surface 607 of the pump housing 601 whilst second deformed surface 605 faces second inner surface 608 of the pump housing 601.

In use first gap 609 defined between first deformed surface 603 and first inner surface 607 has a fluid comprising blood located therein whilst second gap 610 defined between second deformed surface 605 and second inner surface 608 also has a fluid comprising blood located therein.

In use impeller 600 is caused to rotate about impeller axis 611 such that relative movement across first gap 609 between first deformed surface 603 and first inner face 607 occurs and also relative movement across second gap 610 between second deformed surface 605 and second inner surface 608 occurs. The orientation of the deformities of first deformed surface 603 and second deformed surface 605 relative to the line of movement of the deformed surfaces 603, 605 relative to the inner surfaces 607, 608 is such that the fluid in the gaps 609, 610 experiences a change in height of the gap 609, 610 as a function of time and with the rate of change dependant on the shape of the deformities of the deformed surfaces and also the rate of rotation of the impeller 600 relative to the housing 601. That is, at any given point on either inner surface 607 or 608, the height of the gap between the inner surface 607 or 608 and corresponding deformed surface 603 or 605 will vary with time due to passage of the deformed surface 603 or 605 over the inner surface.

Hydrodynamic forces in the form of thrust forces normal to the line of relative movement of the respective deformed surfaces 603, 605 relative to the inner surfaces 607, 608 thus arise.

With this configuration it will be noted that the first gap 609 lies substantially in a single plane whilst the second gap 610 is in the form of a support and angled at an acute angle relative to the plane of the first gap 609.

Accordingly, the thrust forces which can be enlisted to first gap 609 and second gap 610 are substantially normal to and distributed across both the predominantly flat plane of first deformed surface 603 and normal to the substantially conical surface of second deformed surface 605 thereby permitting restoring forces to be applied between the impeller 600 and the pump housing 601 thereby to resist forces which seek to translate the impeller 600 in space relative to the pump housing 601 and also to rotate the impeller 600 about any axis (other than about the impeller axis 611) relative to the pump housing 601. This arrangement substantially resists five degrees of freedom of movement of impeller 600 with respect to the housing 601 and does so predominantly without any external intervention to control the position of the impeller with respect to the housing given that disturbing forces from other sources, most notably magnetic forces on the impeller due to its use as rotor of the motor are net zero when the impeller occupies a suitable equilibrium position. The balance of all forces on the rotor effected by manipulation of magnetic and other external sources may be adjusted such that the rotor is predominantly hydrodynamically born.

It will be observed that these forces increase as the gaps 609, 610 narrow relative to a defined operating position and decrease as the gaps 609, 610 increase relative to a defined operating gap. Because of the opposed orientation of first deformed surface 603 relative to second deformed surface 605 it is possible to design for an equilibrium position of the impeller 600 within the pump housing 601 at a defined equilibrium gap distance for gaps 609, 610 at a specified rotor rotational speed about axis 611 and rotor mass leading to a close approximation to an unconditionally stable environment for the impeller 600 within the pump housing 601 against a range of disturbing forces.

In this state the impeller 600 is effectively suspended exclusively by hydrodynamic thrust faces.

Characteristics and advantages which flow from the arrangement described above and with reference to the embodiments includes:

1. Low running speed, hence low haemolysis and controlled fluid dynamics (especially shear stress) in the gap between the casing and impeller. This in turn can lead to the selection of radial off-flow and minimal incidence at on-flow to the rotor;
2. Radial or near-radial off-flow from the impeller can be chosen in order to yield a "flat" pump characteristic (HQ) curve.

Control System—Detailed Description

Figure 28:
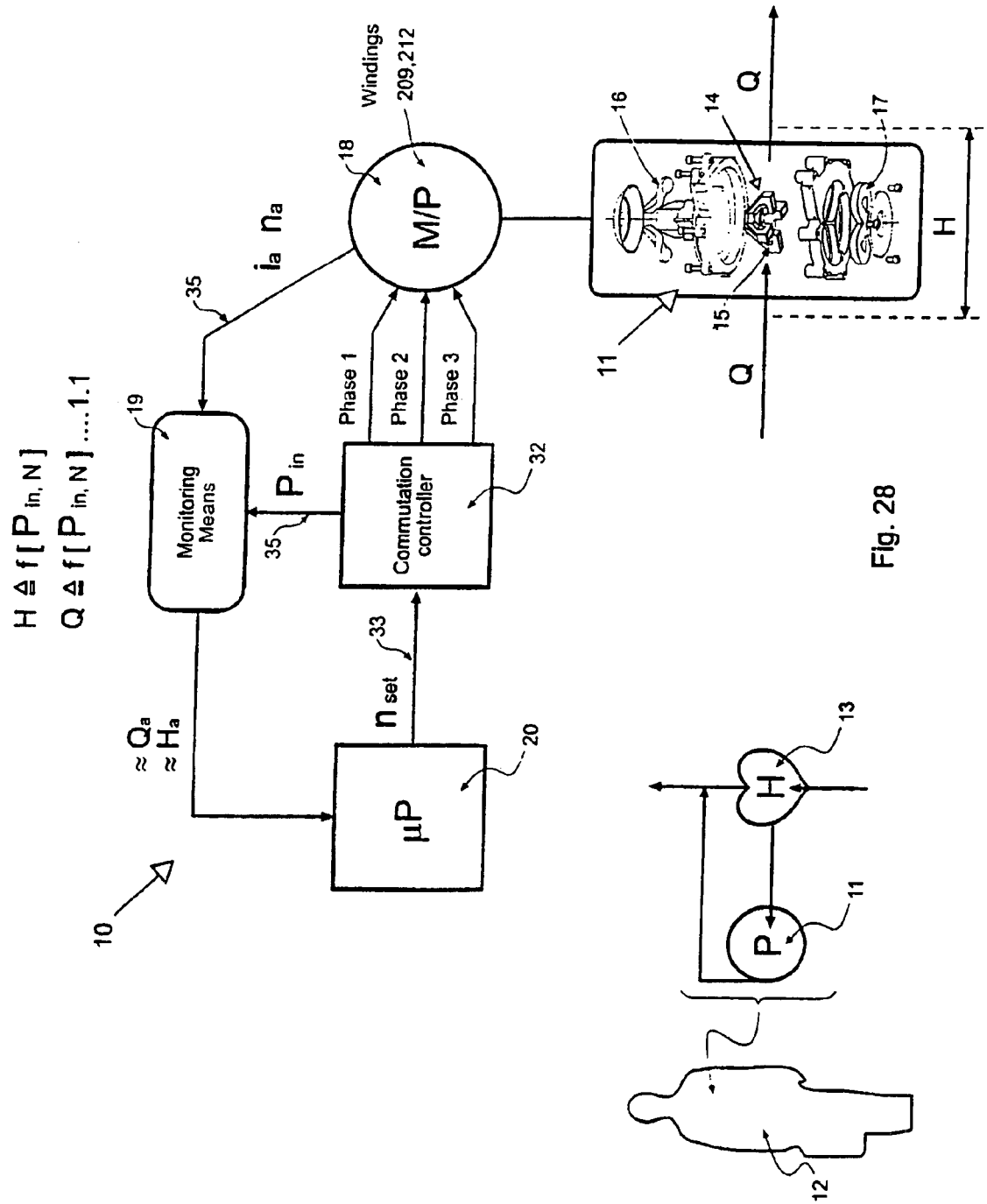
FIG. 28 is a block diagram of a non-contact estimation and control system in accordance with a first embodiment of the invention applied to a blood pump.

Embodiments of the present invention relate to a non-contact estimation and control system usable, although not exclusively, with blood pump systems of the type illustrated in FIG. 28.

In this instance the estimation and control system 10 operates on and receives sensor feedback from pump assembly 11 adapted for implantation in human body 12 and arranged to operate in parallel across at least a part of the heart 13 so as to at least assist if not fully take over the pumping function of heart 13.

The pump assembly 11 includes an impeller 14 having vanes 15 which, when urged to rotate by a magnetic field generated in one or more of coils 16, 17 generates a pressure head H across the pump assembly 11 and causes a flow of blood Q therethrough. In this instance the impeller 14 is both a radial pump impeller and a rotor of motor 18 by virtue of the inclusion of magnets (not shown) within at least part of the impeller 14.

Monitoring means 19 is adapted to sense electric current appearing in one or more of coils 16, 17 via sensing line 35 which, in conjunction with monitoring of voltage derived from commutation controller 32 (which injects current into one or more of the same coils 16, 17) permits the monitoring means 19 to derive power input ($P_{in}$) consumed by motor 18 and actual rate of rotation of the motor/impeller 14 ($n_a$).

By means of equation 1.1 (in FIG. 28) it is thereby possible for monitoring means 19 to calculate an estimation of flow Q (and/or head H) for input into microprocessor 20. Microprocessor 20 accepts these estimates and, together with other desired set points and predetermined values calculates a desired set motor speed $n_{set}$ which commutation controller 32 accepts via line 33. The commutation controller 32 then injects current into one or more of coils 16, 17 in order to cause impeller 14 to rotate at that set (desired) speed.

FIG. 20 illustrates the impeller 14 utilised in example 1 (to follow) in greater detail.

Figure 29:
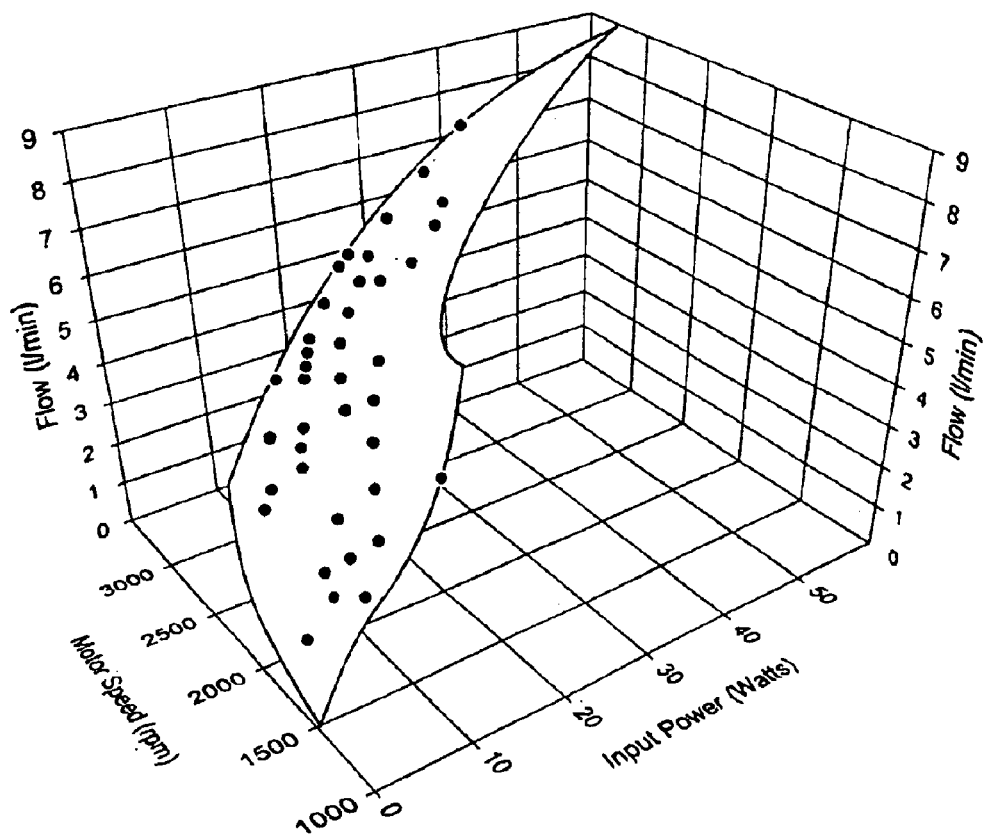
FIG. 29 is a characteristic estimation curve utilised by the non-contact estimation and control system of FIG. 1.

FIG. 3 illustrates the head versus flow characteristic achievable with the impeller of FIG. 20 for a number of different motor powers (Pin). FIG. 29 illustrates the characteristic curve used by the monitoring means 19 for example 1 (to follow) in accordance with the equation 1.1.

EXAMPLE 1

Flow rate and pressure difference (or head) are key variables needed in the control of implantable rotary blood pumps. However, use of invasive flow and/or pressure probes can decrease reliability and increase system power consumption and expense. For given fluid viscosity, the flow state is determined by any two of the four pump variables: flow, pressure difference, speed and electromagnetic torque (apart from the possibility of non uniqueness of solutions). Instead of torque, motor current or input power can be used. Thus if viscosity is known, or if its influence is sufficiently small, flow rate and pressure difference can be estimated from the motor speed and input power, which can be determined from current and voltage measurements on the motor input leads.

The centrifugal blood pumps of previously described embodiments use a hydrodynamic bearing and can be constructed so that the variation with viscosity is sufficiently small to enable flow and pressure difference estimation using signals derived from the coils 16, 17.

For this example a flow loop was set up consisting of the pump and 2.4 m of ⅜" tubing giving a net fluid volume of 177 ml.

The fluid filled tubing was sunk into a water bath with a controlled heater. Temperature sensors were attached to the tubing to provide visual feedback on fluid temperature. Pressure taps were made on the inlet and outlet nozzles of the pump which interfaced to a differential pressure transducer with digital display to measure pressure across the pump. A Clamp on Transonics flow probe and meter were used to measure flow rate and input power (motor supply voltage and current) was monitored via digital panel meters on the power supply. Pressure was varied by adjustment of a tubing clamp and motor speed by wuitable electrical adjustment.

Two tests were conducted. The first with 5% saline, the second with red blood cell suspensions, haematocrit being 32%. In both cases the circulating fluids were heated to 37° C. 5% saline was chosen since its viscosity is about that of water at 23 deg C.

Flow rate, pressure head, pump speed and electrical input power were measured for both fluids.

Data for saline and blood was combined and correlated on a surface plot describing both flow rate as a function of motor speed and input power as illustrated in FIG. 29.

Curve fitting of this plot produced the equation Q=20.29+ 4.73 ln(Pin)−0.55 √(n) where Q is flow rate in L/min, Pin is electrical input power to the motor in Watts and n is motor speed in rpm. The maximum error for this prediction was 4% for the combined data. Pressure head across the pump was described by the relationship ΔP=−13.68−6.59 ln(Pin)+2.18 e−5 (n)² with equivalent accuracy. Two different rotor designs have been tested in this manner to date both yielding similar accuracy curve fits of the form Q=a+b.ln(Pin)+c.√(n) and of the form ΔP=a+b.ln(Pin)+c.(n)².

The viscosity of saline is approximately 1 mPas. The Viscosity of blood (Hct=32%) given pump shear rates of greater than 100 s⁻¹ is near 3 mPas. Blood viscosity varies from approximately 2.4 to 4.5 mPas over the physiological range in question for shear rates greater than 100 s⁻¹. The variation in viscosity from 1 to 3 mPas produced a maximum error of 4% in the prediction of flow rate.

The pump of FIGS. 1–6 has characteristics such that the model for flow rate prediction based on motor input power and speed is not greatly affected by variation in viscosity. This suggests for this pump it is possible to determine flow with acceptable accuracy without using a separate flow sensor.

The reasons for low error in prediction given change in viscosity are postulated as follows: Firstly that the "flat" H–Q curves for this pump give small variation in pressure head for given flow rates. Secondly the nature of the hydro-dynamic bearing. Although the pump has relatively high disc friction forces, which tend to be most sensitive to viscosity changes, the rotor in this case conserves energy by repositioning in free space according to the fluid viscosity.

Thirdly, the size, where surface roughness is relatively smaller than for smaller higher speed pumps. Fourthly, allowing speed to vary around a set point due to choosing a comparatively long time constant.

Figure 30:
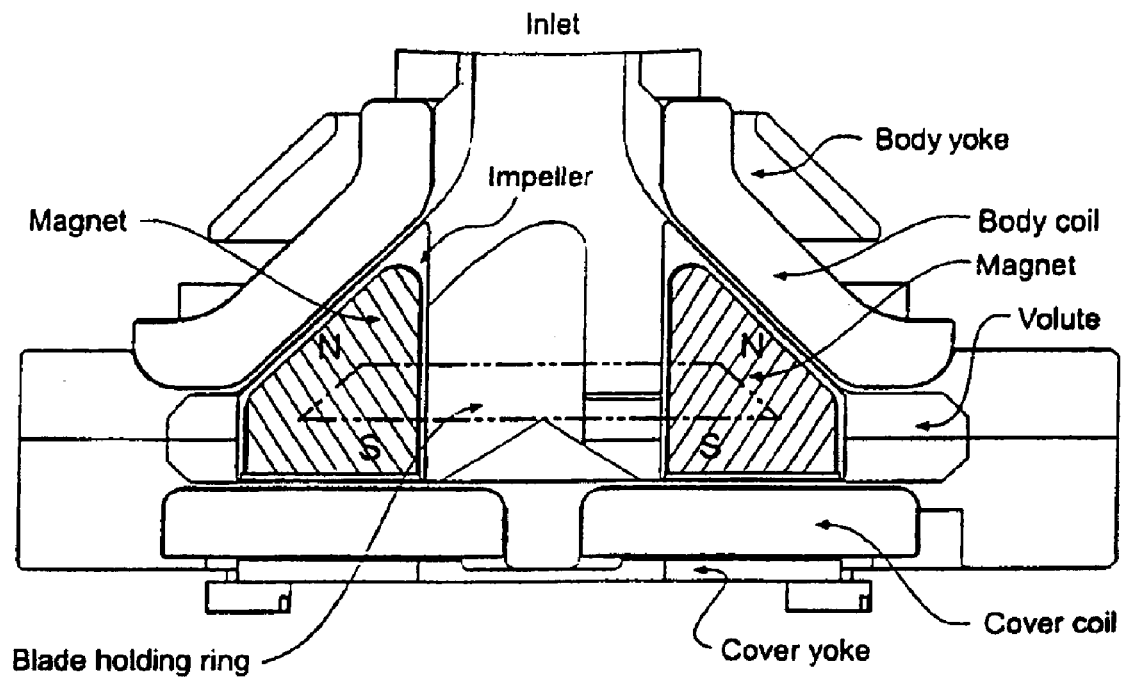
FIG. 30 is a side, cut-away view of the pump of FIG. 1.

FIG. 30 illustrates the pump assembly 11 in cross section as utilised with example 1.

Figure 31:
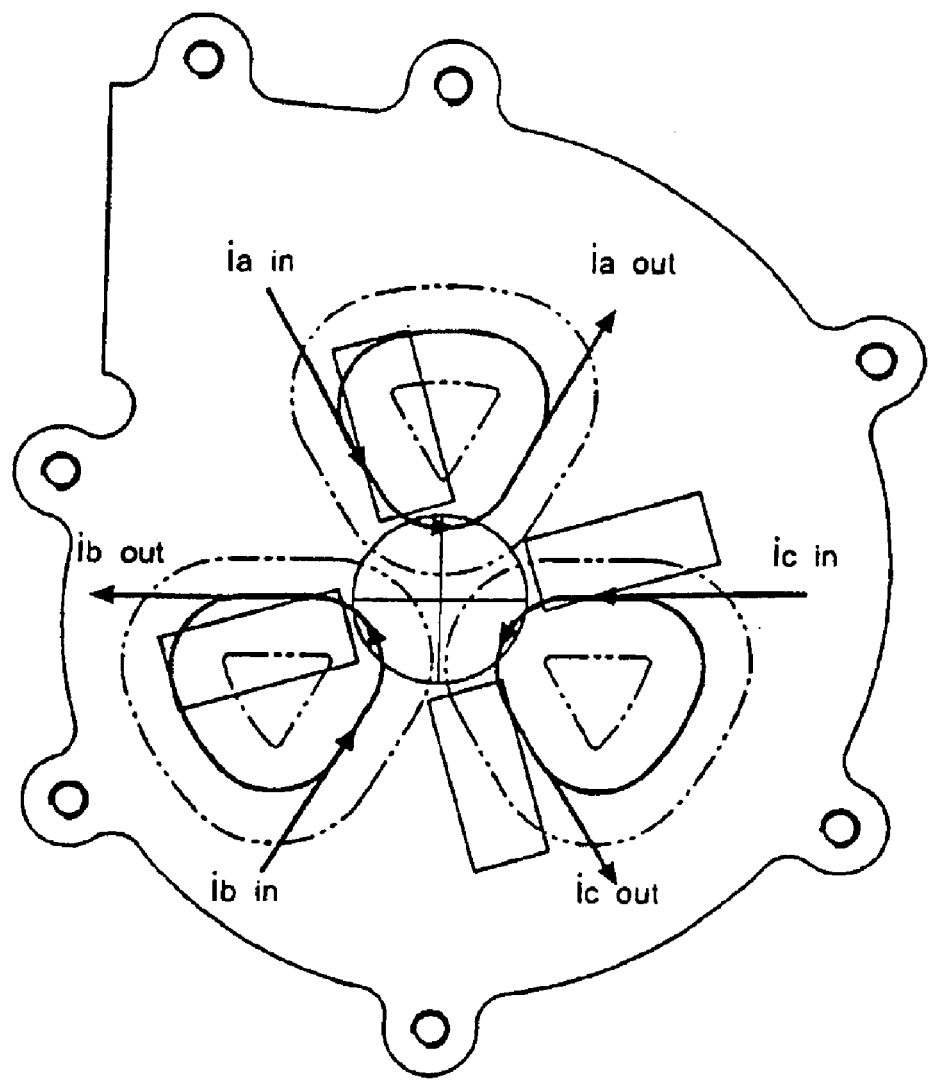
FIG. 31 is a plan, cut-away view of the coil and magnet system of the pump of FIG. 1.

FIG. 31 illustrates in cross section the coil and magnet arrangement used in conjunction with example 1.

With reference to FIGS. 20, 30 and 31 iron yokes are placed outside the coils to increase the magnetic flux and hence increase motor efficiency, and also to reduce stray magnetic fields in the body. The yokes are positioned so that the axial magnetic force on the impeller is zero when it is central in the housing cavity. Furthermore, the yokes are placed at considerable distances from the impeller to keep the negative magnetic stiffness sufficiently low that is places only a small additional demand on the hydrodynamic suspension when the impeller shifts away from the cavity mid-position.

Given the large distance to the yokes, a slotless winding and axisymmetric yokes were chosen. The use of axisymmetric yokes implies zero "cogging" torque. The winding topology coil chosen is of "second harmonic" type with just three coils, one per phase, in each of the body and cover windings. FIG. 31 depicts the cover winding. The body windings align axially with the cover windings but must be bent in several directions to avoid the volute and inlet. This second harmonic topology avoids coil overlaps and is consequently neat and compact and gives low copper mass. However, it is less efficient than other winding options with greater coil mass.

The efficiency is increased by tilting the magnet alignment to an angle of 22.5° from the pump axis (as indicated in FIG. 30 by the magnet hatching), intermediate between the 45° conical body and the flat cover. The cover coil and axial flux form an axial flux motor, and the body coil and flux are intermediate between an axial and radial flux motor.

The motor can be driven by a six-step, sensorless commutation inverter. Superimposed over the coils in FIG. 31 are magnets at an instant when the currents are switched from phases a and c conducting to phases b and c conducting (or v.v.). Parallel coil connection of the cover and body coils (each connected in star configuration) enables some redundancy, in that the motor still runs with the loss of a coil.

The materials used were Ti-6Al-4V for the housing and impeller shell, high remanence NdFeB magnets (VACODYM 510 HR) embedded in the impeller, iron for the yokes (mild steel in prototypes but to be laminated silicon steel) and varnished copper wire for the coils.

The measured negative magnetic stiffness of the teardrop impeller is −4000 N/m (±10%). The axial clearance gaps are 0.1 mm when the impeller is central (this is to match a 0.05 mm taper on the blades for thrust generation so that after a shift of 0.05 mm, the thrust forces are maximal from one impeller face and negligibly small from the other face). Thus if the impeller is shifted axially by the full amount possible (as at start-up if axis vertical), then the magnetic force on the impeller is 0.4 N force. This is less than the impeller weight of 46 gforce, and is considered acceptable. If the yokes were any closer, the force would be higher, increasing the risk of touchdown. Similarly, if the clearance gaps are increased to slacken manufacturing tolerances, then the maximal magnetic force can be increased.

The measured motor efficiency is between 45% and 48% curves, for speed between 2000 rpm and 2500 rpm and motor output power between 3 and 7 W. For example, at 2250 rpm and 3 W motor output (roughly rated conditions), the copper loss was 1.7 W, the eddy loss in the titanium was 1.0 W, and the iron loss in mild steel yokes was 0.7 W, giving a motor efficiency of 47%.

Figure 32:
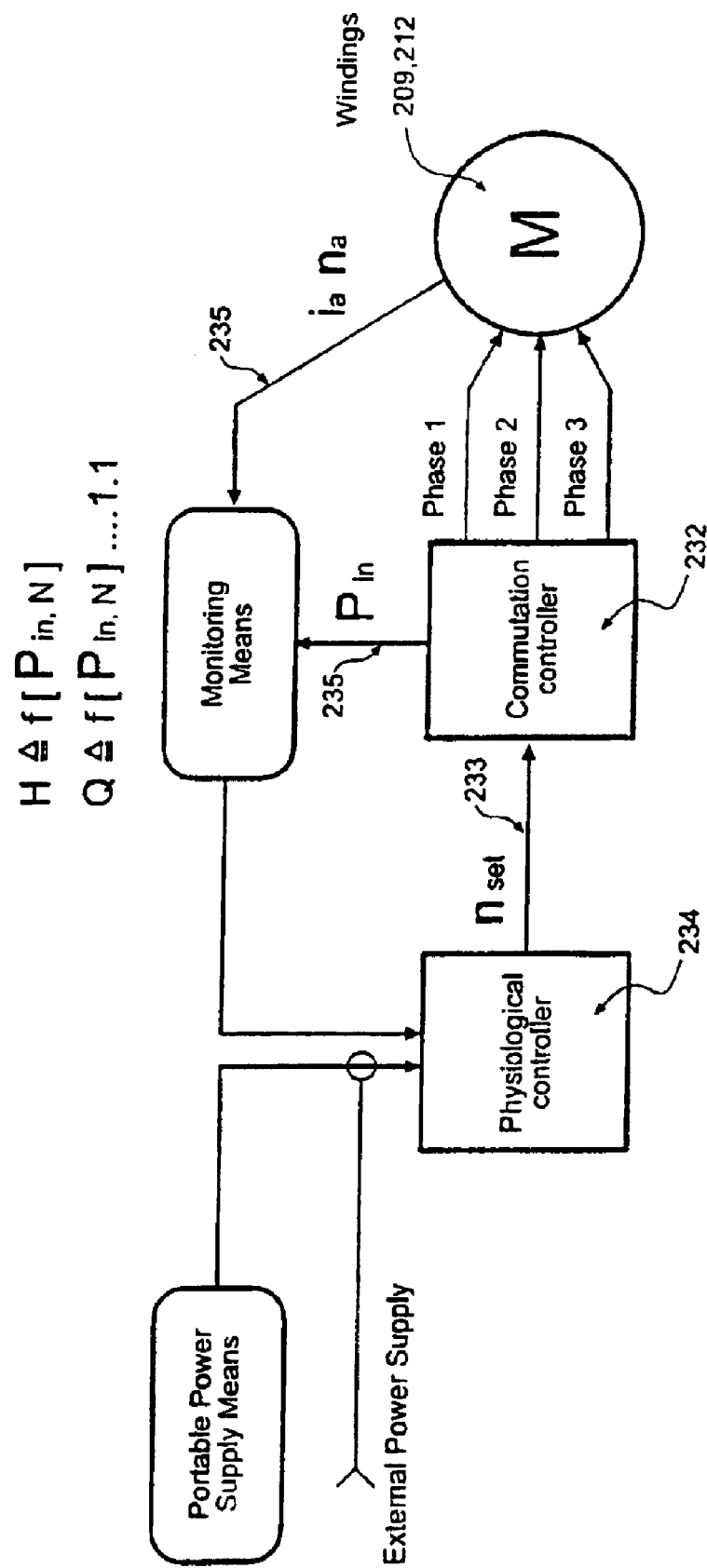
FIG. 32 is a block diagram of an electronic driver circuit for the pump assembly of FIG. 7.
Figure 33:
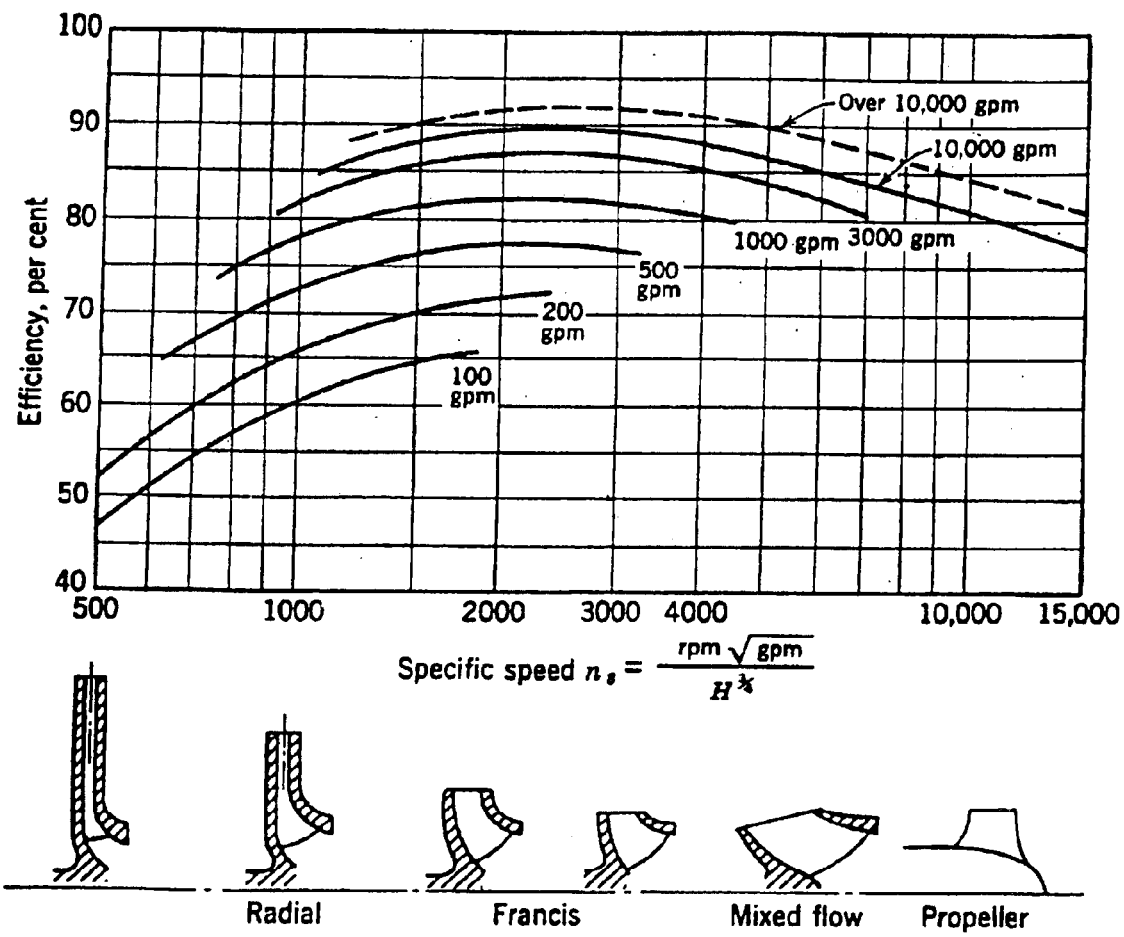
FIG. 33 illustrates efficiency versus specific speed for a range of pump types, to be contrasted with the flat HQ curves of FIG. 13.

With reference to FIG. 32 the example 1 can be applied to the preferred embodiment of FIG. 7 to 15 comprising pump assembly 200 incorporating an estimating and control system of the type described with reference to FIGS. 28 to 31.

With particular reference initially to FIG. 7 the pump assembly 200 comprises a housing body 201 adapted for bolted connection to a housing cover 202 and so as to define a centrifugal pump cavity 203 therewithin.

The cavity 203 houses an impeller 204 adapted to receive magnets 205 within cavities 206 defined within blades 207. As for the first embodiment the blades 207 are supported from a support 208.

Exterior to the cavity 203 but forming part of the pump assembly 200 there is located a body winding 209 symmetrically mounted around inlet 210 and housed between the housing body 201 and a body yoke 211.

Also forming part of the pump assembly 200 and also mounted external to pump cavity 203 is cover winding 212 located within winding cavity 213 which, in turn, is located within housing cover 202 and closed by cover yoke 214.

The windings 212 and 209 are supplied from the electronic controller of FIG. 32. Otherwise the structure is as described with reference to the third embodiment.

Further Embodiments

In the forms thus far described top surfaces of the blades 8, 207 are angled at approximately 45° with respect to the longitudinal axis of the impeller 100, 204 and arranged for rotation with respect to the internal walls of a similarly angled conical pump housing. The top surfaces are deformed so as to create the necessary restriction in the gap between the top surfaces of the blades and the internal walls of the conical pump housing thereby to generate a thrust which can be resolved to both radial and axial components.

In the examples thus far the bottom faces of the blades 207 comprise surfaces substantially lying in a plane at right angles to the axis of rotation of the impeller and with their deformities define a gap with respect to a lower inside face of the pump housing against which a substantially only axial thrust is generated.

Other arrangements are possible which will also, relying on these principles, provide the necessary balanced radial and axial forces. Such arrangements can include a double support arrangement where the conical top surface of the blades is mirrored in a corresponding bottom conical surface. The only concern with this arrangement is the increased depth of pump which can be a problem for in vivo applications where size minimisation is an important criteria.

Summary of Operation Principles

The estimation and control system described with reference to Example 1 and the previous embodiments is "sensorless" in that it derives an estimate of relevant pump parameters from signals available from one or more of the drive coils of the motor. Hence no separate sensor device is required to control the pump assembly in use.

It is hypothesized that the ability to control the pump assembly in this manner to a sufficiently good approximation derives from shaping the impeller of the pump so that a relatively flat head versus flow characteristic is obtained over the flow rate range expected and/or required of the pump, in use.

It is postulated that relative radial off-flow and lack of constraint of the fluid within the impeller derived from the relatively low number of impeller blades aids in achieving the relatively flat pump characteristic curves as shown for example in FIGS. 3 and 13.

It is also postulated that, in the embodiments described in the specification, the impeller blades are arranged to guide fluid carefully through the rotor so as to reduce re-circulation. There are also relatively large gaps between the blades so that the fluid is relatively poorly constrained leading to loosely constrained flow of fluid within the pump housing.

EXAMPLE 2

With reference to FIGS. 33 to 39 a specific example of a particularly preferred rotor, centrifugal flow pump assembly incorporating the rotor and a control system therefor will now be provided.

Figure 35:
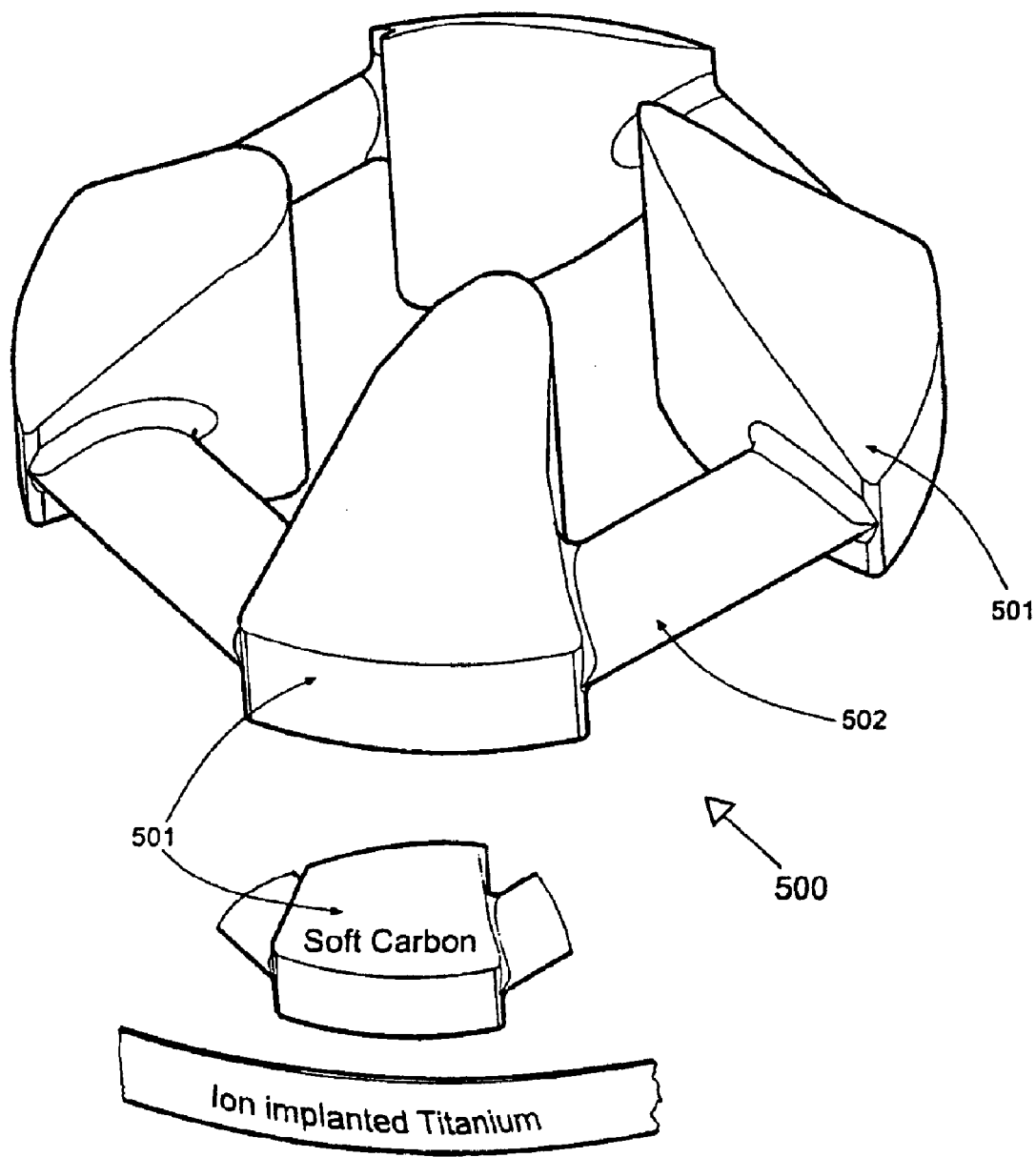
FIG. 35 illustrates a particular preferred form of impeller described with reference to example 2.

The rotor 500 of this example is illustrated in FIG. 35 and is arranged to operate within a housing structure as previously described in this specification with reference to FIG. 7. The rotor 500 is urged to rotate by an electromagnetic field supplied via coil structures again as previously described with reference to FIG. 7. The control system which maintains control over the operation of the rotor within the housing is determined by a non-contact estimation and control system as previously described in this specification but further subject to an optimal pumping condition strategy as will be described below.

With particular reference to FIG. 35 it will be noted that the impeller blades 501 are held in mechanical relationship with each other by struts 502.

By increasing the smallest radius from the centerline to the blades (i.e. to the nose of the blades) at the top and not at the bottom of the impeller, an axial thrust force can be imposed on the impeller toward the bottom. This arrangement can be carefully designed so as to bias the load to the bottom bearing and relieve the top bearing which is more highly loaded (in that it must resist both axial and radial loads).

Operation Region for the Pump

Figure 34:
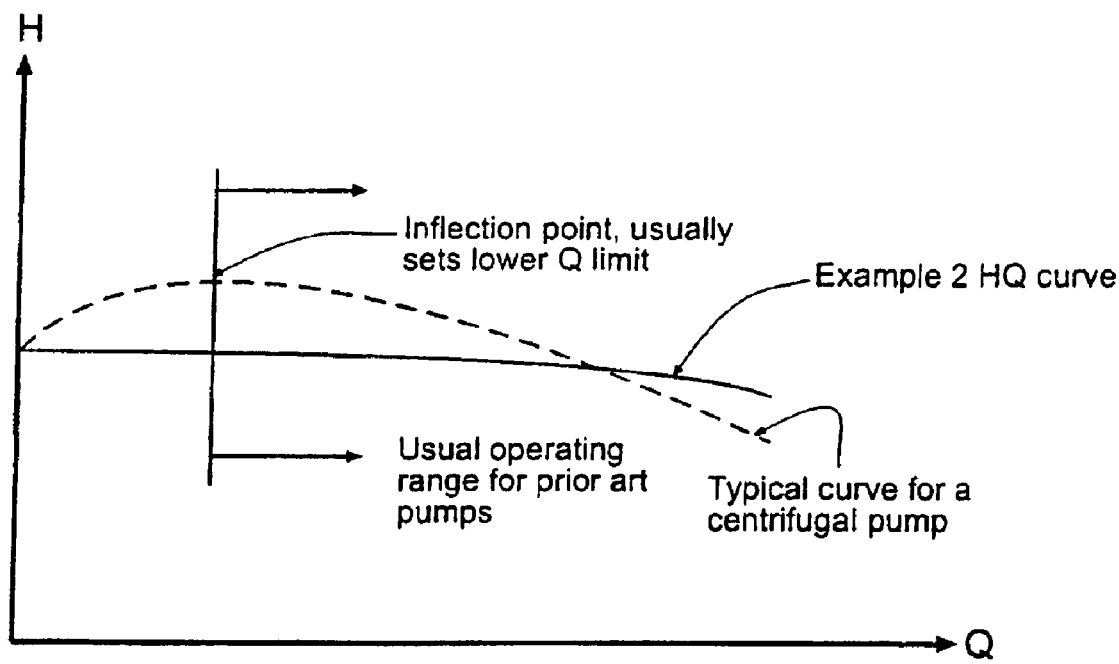
FIG. 34 provides a graphical comparison of HQ curves for pump constructions according to embodiments of the invention compared with typical centrifugal pump HQ curves.

With reference to FIG. 34 the pump of this example is arranged to follow an HQ curve that does not roll-off towards shut-off. That is, if the pressure head (H) developed by the pump at any given operating speed (N) is plotted against flow rate delivered (Q), then at low flow rates (and even at zero flow) there is no loss of head compared with the head developed at the nominal operating point. Typically in other centrifugal pumps of the prior art pressure head developed increases with increasing flow rate from zero or "shut-off" to a point of inflection in the HQ curve then head reduces with further increases in flow rate. It is normal practice in the prior art to operate a pump to the right of the inflection point to avoid instabilities known as surge which occur because at a given pump speed a pressure head required might be met by one of two flow rates delivered by the pump—one at either side of the inflection point. To the right of the inflection point, typically the HQ curve falls steeply.

In the pump of this example, since there is no inflection point in the HQ curve, the pump can be operated stably throughout its entire range of flow rates. This means that the pump is operating in the flattest part of the HQ curve and enables better prediction of flow and pressure from parameters which may be attained readily from motor performance characteristics (viz.: Voltage, current and speed).

Factors which contribute to the flat HQ curve of the pump of this example, with an absence of an inflection point, include near-radial off-flow from the impeller, low specific-speed design of the pump and a low number of impeller blades.

An optimal control strategy will now be described with reference to FIGS. 33 to 39.

Optimal Control Strategy

It is the aim of the rotary blood pump and its associated control system of Example 2 to restore normal cardiac output levels such that the demand for perfusion is supplied by pumping as much blood from the ventricle as is returned to it from the lungs.

Rate responsive control of the pump is described in this example to determine the optimum point for unloading the heart while at the same time avoiding over pumping leading to suction or under pumping leading to regurgitation during the varying physiological climate of every day life.

Figure 36:
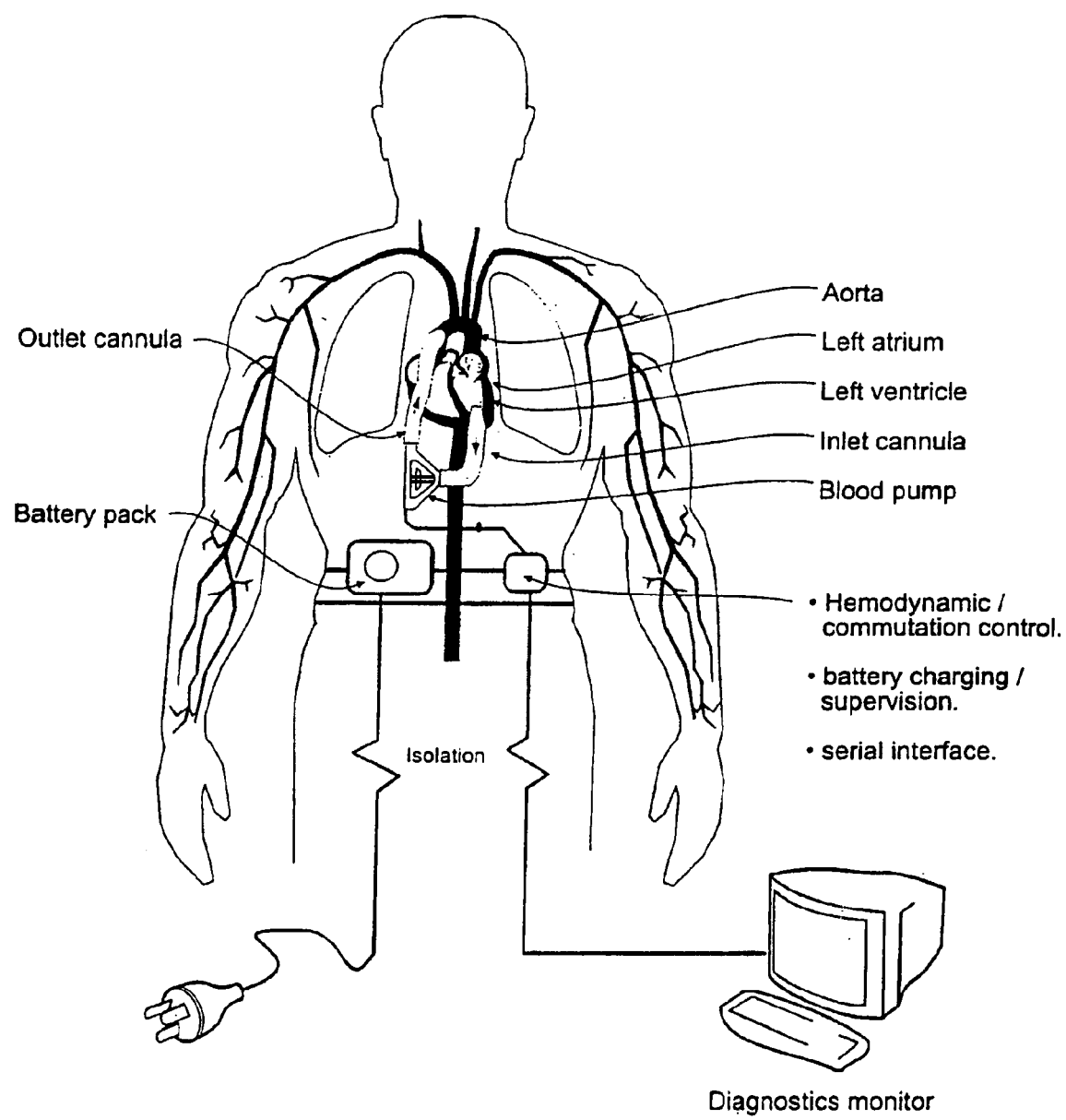
FIG. 36 illustrates an implanted rotary pump assembly and associated control system according to example 2.

Since the pump has no valves, there is a possibility of back flow when the pump speed is low. FIG. 36 shows the normal direction for flow of blood through the pump from the left ventricle to descending aorta. This point changes with preload (left ventricle pressure) and afterload (arterial pressure) across the pump. Furthermore, as pump speed is increased the aortic valve will eventually remain closed and additional increases in speed will cause collapse of the ventricle.

The rotary blood pump is sensitive to pre load and after load if the pump speed set point has no feed back. Instantaneously increasing the pressure head across the pump will cause an increase in impeller speed and decrease in electrical input power and pump flow rate. Decreasing it will have opposite effects.

In this example the time constant of the control system is set to be relatively slow to the extent that disturbances induced in the speed of blood flow by the action of the heart will be counteracted by the control system relatively slowly. The resulting variation in speed of the impeller, in use, is then utilised to calculate an estimate of the operating point to an improved level of accuracy.

The long time constant means that instantaneous pump speed and electrical input power will vary cyclically under the influence of the pumping action of the heart or, in other words, will be modulated by the heart beat.

In this example the time constant of the control system is set to be greater than the rotational inertial time constant of the impeller. Specifically, in this example, the time constant is set at 5 seconds which is longer than one cardiac cycle.

Optimal Pumping and Avoiding Over Pumping

If pump speed is set such that maximal unloading of the ventricle is achieved and venous return is reduced as in the case from exercise to resting, over pumping from the ventricle will result in suction and collapse of the ventricle may occur.

Figure 37:
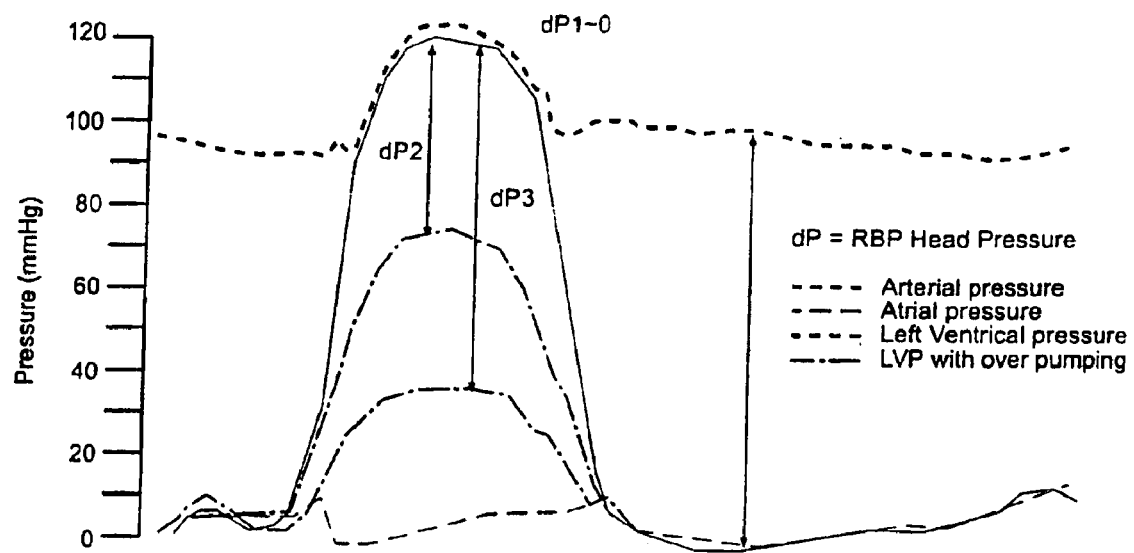
FIG. 37 illustrates graphically a control strategy to avoid over pumping for the system of example 2.
Figure 38:
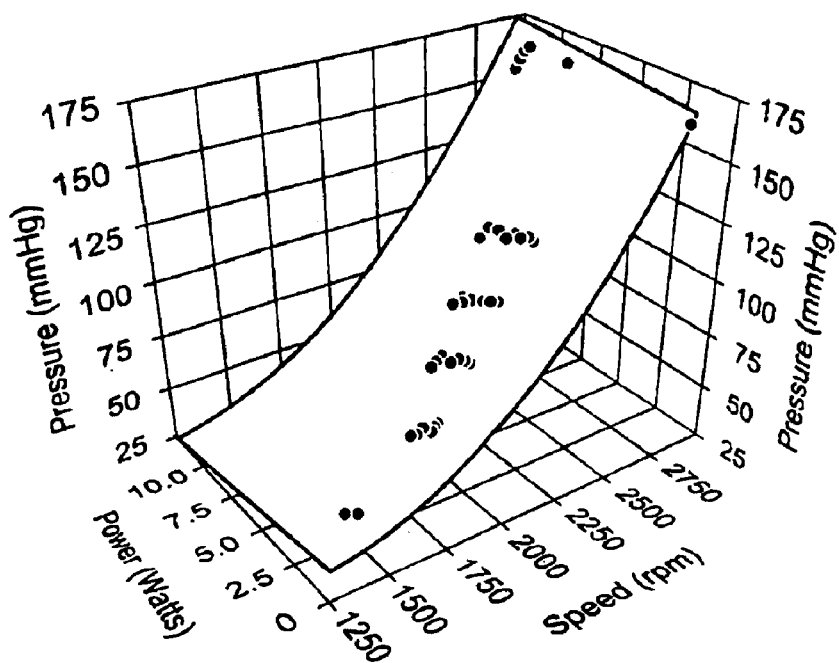
FIG. 38 is a graphical illustration of application of the algorithms of the control system to estimate pressure head for example 2.
Figure 39:
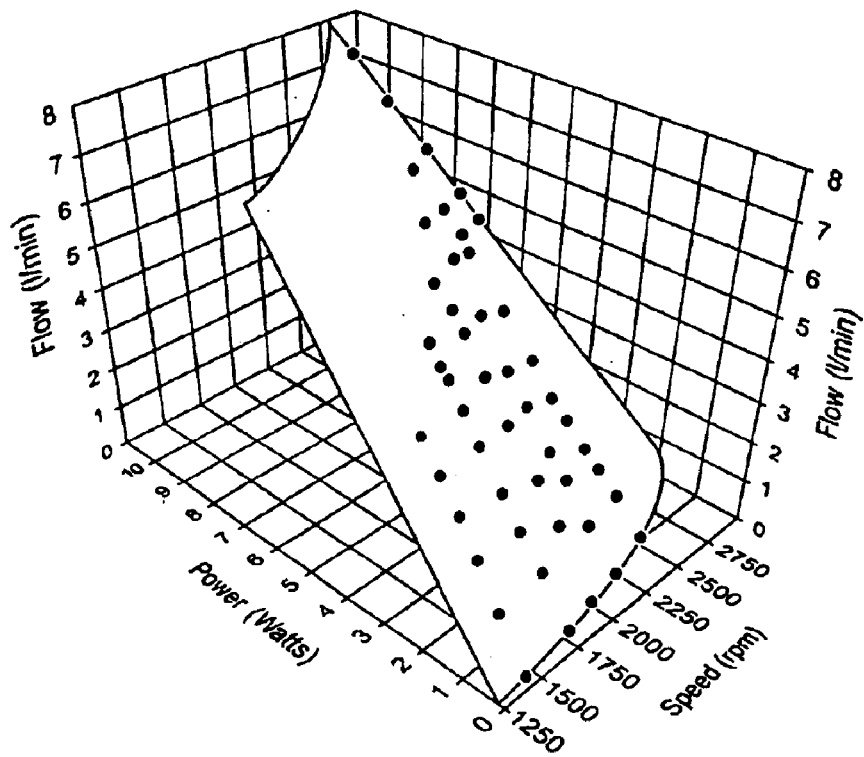
FIG. 39 is a graphical illustration of application of the algorithms of the control system to provide a flow rate estimate for the system of example 2.

As the pump speed is increased the ventricle empties and the pressure in the ventricle during systole decreases. This is shown in FIG. 37 as dP is reduced from dp1 to dP3 during systole. If the amount of emptying of blood from the ventricle matches the amount of filling, the pump is on the verge of producing suction or negative pressures in the ventricle. Beyond the point that the aortic valve remains closed and the peak left ventricular pressure during systole continues to decrease and suction will begin to occur during the diastolic phase.

Further increases in pump speed will cause the peak left ventricular pressure to become so low that the ventricle walls will occlude blood flow through the inlet cannula over the entire cardiac cycle, even during systole. Suction should be avoided even during diastole. The optimum point of pumping is just allowing the aortic valve to open. Over pumping is considered increasing pump flow beyond this point.

The solution to detection of the point of optimal pumping in this example lies in the time domain.

The point at which the aortic valve just remains closed is the point of total assist given the name OCA (optimal cardiac assistance). This is the point at which minimum head pressure across the pump begins to rise with increasing pump speed. In other words during systole the left ventricle peak pressure begins to decrease as average pump speed is increased.

Therefore for a given preload, afterload and contractile strength of the ventricle there will be a point where optimum unloading of the ventricle occurs. Increase in pump speed beyond this point will result in collapse of the ventricle. This minimum pressure across the pump during systole will produce a maximum flow through the pump, maximum torque on the impeller and minimum instantaneous speed.

Therefore pumping at the point of optimal cardiac assistance and avoiding over pumping, the control algorithm should maintain minimum pump speed such that the minimum head pressure across the pump does not increase. Therefore the new desired set point Nnew to hold the optimal cardiac assistance point can be defined by the old speed value Nold reduced by a factor proportional to the increase in minimum systolic head pressure ($\Delta Hsys$) beyond the minimum possible head pressure ($\Delta Hmin$). Kp is the proportional constant. This is described by equation 1.

$$Nnew=Nold-[Kp*(\Delta Hsys-\Delta Hmin)] \quad \text{equation 1}$$

The instantaneous head pressure can be estimated by non-contact methods as previously described in this specification with reference to Example 1.

This is a simple control equation that can be readily implemented in an embedded microcontroller system.

Avoiding Under Pumping

The other boundary condition of under pumping occurs when flows through the pump become negative with diastole. Regurgitation can cause stagnation of blood and lead to thrombus formation as well as increasing atrial pressures leading to pulmonary adaema.

Regurgitant or negative flow in the pump begins to occur as pump set point speed is decreased to the extent where levels and phase lags between pump outlet and inlet pressures during diastole cause flow reversal.

$$Nregurg=N(t) \text{ for Qdiastole}=OL/min \quad \text{equation 2}$$

where N(t) is the instantaneous impeller rotational speed, Qdiastole is the minimum flow rate through the pump during diastole and Nregurg is the minimum speed at which non regurgitant flow occurs. Flow rate can be estimated by non-contact methods as previously described as a function of motor speed and input power as shown earlier with reference to Example 1.

Summary of Operational Forces Experienced

In practical operation of Example 2 the rotor 500 should be made to operate such that blood flow is adequate in accordance with the constraints and the optimal control strategy described above. In addition, whilst in operation, the rotor 500 ideally should never make contact with the inside walls of the housing in which it rotates. Should such contact be made then the control system should be able to recover from this condition so as to return the rotor to an operational condition and, in addition, damage sustained during a touchdown must be minimised so that, upon return to normal operation after touchdown, there is no effect on steady state operation.

Touchdown is countered by ensuring that there is sufficient restoring hydrodynamic force exerted upon the rotor 500 to counteract any disturbing force experienced by the rotor 500 such that probability of touchdown is reduced to a sufficiently low value.

Broadly, for the centrifugal pump structure described with reference to this example and having a rotor 500 of the type described with reference to this example it has been found that worst case restoring forces occur when the rotor is rotating in a low viscosity medium and running at its lowest speed. For example, running at approximately 1800 rpm in a blood substitute representing the lowest viscosity likely to be encountered in practice the axial restoring force available is approximately 2 Newton. The corresponding radial restoring force is approximately 0.5 Newton under these conditions.

In a more usual and expected operating environment with blood viscosity of the order of 2.5 mPs and with the rotor running at approximately 3000 rpm the axial restoring force available is approximately 9 Newton whilst the radial restoring force is approximately 2.25 Newton. If the speed is reduced to around 2400 rpm then the axial restoring force is approximately 5.3 Newton and the radial restoring force is approximately 1.3 Newton.

An expected typical steady state disturbing force can be of the order of 0.45 Newton including the effects of gravity upon rotor 500. Magnetic field disturbances arising from the drive mechanism can add a further 0.1 Newton of disturbing forces. Allowing for acceleration effects on the entire assembly in vivo and in use it is expected that typical maximum disturbing forces encountered by rotor 500 will be of the order of 1 Newton.

Use of a shrouded rotor as described earlier in the specification can double the radial resistance force available to counteract disturbing forces.

In addition appropriate coatings and/or structure materials will be used on the respective rotor 500 and at least inner walls of the housing to minimise damage and/or damaging effects arising from a touchdown.

Coatings and/or inherent structural materials will be selected so as to reduce the friction co-efficient between the rotor and the casing and also to reduce specific damage such as gouging.

Current particularly preferred materials for this purpose include amorphous carbon based materials or microcrystalline carbon based materials and titanium nitride. In a particular form it has been found advantageous to have different materials on opposing surfaces such as, for example, titanium nitride on one of the surfaces and the carbon based materials on the other.

Carbon based material against carbon based material corresponding surfaces has been found to give a very low co-efficient of friction (typically 0.05) and low damage. Conversely, titanium against titanium has been found to give the reverse effect and is not recommended.

Further particular preferred coating arrangements are as follows:

Application of coatings to the Ti-6Al-4V substrate of a blood pump:

These coatings specifically include carbon with a graphitic microcrystalline structure, prepared using unbalanced magnetron sputter deposition and amorphous carbon coatings.

These coatings provide a biocompatible lining for the device, with enhanced hardness, high elastic recovery under impact conditions, low friction coefficients of <0.06 under lubricated conditions, and high wear resistance.

Also coatings applied using plasma immersion ion implantation of nitrogen, titanium nitride and carbon, or combinations of these treatments, for enhancement of hardness, improved elastic recovery under impact conditions, low friction and high wear resistance.

Other potential candidates include pyrolitic carbon, illumina, zirconia or combinations thereof.

Overall the desirable characteristics to be achieved by the coatings are:

1. Zero eddy current loss in the casing;
2. A hard material on at least one surface to give a good bearing property; and
3. The materials must be biocompatible, particularly in relation to blood contact.

More generally in relation to modification to surfaces attention can be paid to other characteristics of the surface structure of both the rotor 500 and the at least inner wall of the housing with a view to providing flexibility or other dynamic characteristics which can aid hydrodynamic bearing behaviour. Elasto-hydrodynamic bearings are one such arrangement which can be achieved by further attention to the materials of which the rotor and/or housing inner walls are constructed as will now be described.

Elastohydrodynamic Bearings (EHD Bearings)

Elastohydrodynamic (EHD) bearings rely on the principle that if forces applied to bearings are sufficiently large then the bearing surface will distort. This distortion can lead to a greater efficacy of the bearings allowing greater loads to be carried for a given bearing dimension. Of course the magnitude of force necessary to distort the bearing surface must be viewed relative to the modulus of elasticity of the material from which the bearing surface is manufactured. For EHD to be applicable to rotary blood pumps, the modulus of elasticity of the bearing surfaces must be low in order for them to be distorted by forces of a few Newtons magnitude. For these reasons polymeric materials such as polyurethane or silicone may prove acceptable materials from which to fabricate the bearing surfaces (these materials should sit on a harder substrate of, say, titanium or a ceramic). The fundamental shape of the hydrodynamic bearing, including particularly the "deformed surfaces" would need to remain substantially the same as for the hydrodynamic bearings previously described in this application for use in a blood pump.

Bio-EHD Bearings

An alternative approach is to allow tissue overgrowing the bearing substrate to act as the EHD component. The substrate may be porous such that it allows a pseudoneointimal cell lining to grow into the pores on the substrate surface. It is commonly reported that the pseudoneointimal lining thickness is stable and around one cell deep. The advantage of using a "bio-EHD" component on the surface is that damage to the EHD component may regenerate within a few hours of damage occurring. Possible drawbacks may be a tendency for a bio-EHD component to sustain damage under relatively low shear stresses commonly seen in a rotary blood pump and for sections of bio-EHD to be stripped away forming potentially dangerous embolii. This may be countered by additional surface treatments which promote stability of the pseudoneointima. Once again, the fundamental shape of the bearing, that is the "deformed surfaces" should remain substantially the same as for the hydrodynamic bearings of the blood pump embodiments previously described.

The above describes only some embodiments and some examples of a rotary blood pump and control system therefor and modifications, obvious to those skilled in the art, can be made thereto without departing from the scope and spirit of the present invention.

Industrial Applicability

The pump assembly 1, 200 is applicable to pump fluids such as blood on a continuous basis. With its inherently simple mechanical and control structure it is particularly applicable as an in vivo heart assist pump.

The pump assembly can also be used with advantage for the pumping of other fluids where damage to the fluid due to high shear stresses should be avoided or where leakage of the fluid should be prevented with a very high degree of reliability—for example where the fluid is a dangerous fluid.

What is claimed is:

1. A rotary blood pump for use in a heart assist device, the pump comprising:
    an impeller an even number of blades and generally circumferentially extending struts interconnecting the blades at an outer periphery of the impeller; and
    a pump housing wherein the impeller is suspended in use within the pump housing exclusively by hydrodynamic thrust forces generated by relative movement of the impeller with respect to and within the pump housing; and wherein at least one of the impeller and the pump housing includes at least a first deformed surface lying on at least part of a first face and a second deformed surface lying on at least a part of a second face which, in use, move relative to respective facing surfaces on the other of the at least one of the impeller and the pump housing thereby to form at least two relatively moving surface pairs which generate relative hydrodynamic thrust between the impeller and the pump housing which includes everywhere a localized thrust component substantially and everywhere normal to the plane of movement of the first deformed surface and the second deformed surface with respect to the facing surfaces; and wherein the combined effect of the localized normal forces generated on the surfaces of the impeller is to produce resistive forces against movement in three translational and two rotational degrees of freedom.

2. The blood pump of claim 1 wherein the first deformed surface lies on at least part of a first face of the impeller.

3. The blood pump of claim 1 wherein the second deformed surface lies on a second face of the impeller.

4. The blood pump of claim 1 wherein the first deformed surface lies on a first inner face of the housing.

5. The blood pump of claim 1 wherein the second deformed surface lies on a second inner face of the housing.

6. The blood pump of claim 2 wherein the first deformed surface covers entirely the first face.

7. The blood pump of claim 2 wherein the first deformed surface covers entirely the second face.

8. The blood pump of claim 1 wherein the first face lies at an acute angle relative to the second face.

9. The blood pump of claim 1 wherein the hydrodynamic forces are augmented by at least one secondary force to support the impeller for rotation within the housing.

10. The blood pump of claim 9 wherein the at least one secondary force comprises magnetic force.

11. The blood pump of claim 1 wherein the first deformed surface comprises deformation in the first face of the impeller whereby a gap between the first deformed surface and a first facing surface on the housing forms, in use, a restriction in the form of a reducing distance between the surfaces with respect to the relative line of movement of the first deformed surface.

12. The blood pump of claim 11 wherein the gap takes the form of a wedge shaped restriction which generates a thrust in use.

13. The blood pump of claim 1 wherein the pump is of centrifugal type or mixed flow type with impeller blades open on both front and back faces of the pump housing.

14. The blood pump of claim 1 wherein the front face of the pump housing is made conical, in order that the thrust perpendicular to a conical surface of the impeller has a radial component, which provides a radial restoring force to a radial displacement of the impeller axis during use.

15. The blood pump of claim 1 wherein the driving torque of the impeller derives from magnetic interaction between permanent magnets within blades of the impeller and oscillating currents in windings encapsulated in the pump housing.

16. The pump of claim 15 wherein the blades include magnetic material therein, the magnetic material being encapsulated within a biocompatible shell or coating.

17. The pump of claim 16 wherein the biocompatible shell or coating comprises a coating which can be applied at low temperature.

18. The pump of claim 16 wherein internal walls of the pump which can come into contact with the blades during use are coated with a hard material.

19. The pump of claim 1 wherein the impeller comprises an upper conical shroud having a deformed surface thereon and wherein blades of the impeller are supported below the shroud.

20. The pump of claim 19 wherein the impeller further includes a lower shroud mounted in opposed relationship to the upper conical shroud and wherein the blades are supported within the upper conical shroud and the lower shroud.

21. The pump of claim 1 wherein at least one of the deformed surfaces is located on the impeller.

22. The pump of claim 1 wherein at least one of the deformed surfaces are located on the housing.

23. The pump of claim 1 wherein the combined effect of the localized normal forces generated on the surfaces of the impeller is to produce resistive forces against movement so as to support the impeller for rotational movement within the housing by the hydrodynamic thrust forces in an adaptive manner whereby the impeller is repositioned, in use, so as to conserve energy as a function of fluid viscosity.

24. The pump of claim 1 wherein the combined effect of the localized normal forces is to produce resistive forces against movement in three translational and two rotational degrees of freedom so as to support the impeller for rotational movement within the housing by the hydrodynamic thrust forces.

25. The pump of claim 1 wherein forces imposed on the impeller in use are controlled by design so that, over a predetermined range of operating parameters, the hydrodynamic thrust forces provide sufficient thrust to maintain the impeller suspended in use within the pump housing.

26. The pump of claim 1 further comprising an electrical drive which urges the impeller to rotate with respect to the pump housing and a controller sensing the speed and input power from electrical parameters of the electrical drive to estimate, in use, head pressure and/or flow rate of the pump.

27. The pump of claim 25 further comprising a regulator in communication with the controller and the electrical drive so as to sense and inhibit under pumping and regurgitation.

28. An estimation and control system for a pump, the pump of the type having an impeller located within a pump cavity in a pump housing, the housing having a fluid inlet in fluid communication with the cavity, the housing having a fluid outlet in fluid communication with the pump cavity, the impeller urged to rotate about an impeller axis so as to cause fluid to be urged from the inlet through the pump cavity to the pump outlet, the impeller urged to rotate by a drive, the impeller supported for rotational movement by an impeller support, the impeller maintained at or near a predetermined speed of rotation by a controller acting on the drive, the controller receiving as input variables a first input variable comprising power consumed by the drive, the controller receiving a second input variable comprising actual speed of rotation of the impeller; the controller thereby estimating at least one of head across the pump and rate of flow of the fluid to an approximation of predetermined accuracy relying on signals available from the drive, wherein the control system is adapted to maintain the speed of rotation of the impeller within a range whereby the impeller, in use, substantially resists five degrees of freedom of movement with respect to the pump housing solely via hydrodynamic forces and predominantly without any external intervention from the control system to control the position of the impeller with respect to the housing.

29. The system of claim 28 wherein the pump has a substantially constant steady state head versus flow rate characteristic over a predetermined flow rate range.

30. The system of claim 28 wherein blades of the impeller are such that a midline chord angle of the blades is inclined substantially radially to internal walls of the pump cavity.

31. The system of claim 28 which relies on sensing of EMF induced in one or more coils forming part of the drive.

32. The system of claim 28 wherein the impeller includes blades inclined such that relative velocity of fluid off-flow from the blades is substantially radial with respect to the impeller axis.

33. The system of claim 28 wherein the pump is a low specific speed pump.

34. The system of claim 33 wherein the pump has a specific speed in the range 100–2000 rev/min(gal/min)$^{1/2}$ ft$^{-3/4}$.

35. The system of claim 33 wherein the pump has a specific speed of approximately 900–1000 rev/min(gal/min)$^{1/2}$ ft$^{-3/4}$.

36. The system of claim 28, wherein the pump comprises a rotary blood pump and wherein the impeller is suspended hydrodynamically within a pump housing by thrust forces generated by the impeller during movement in use of the impeller as it rotates about an impeller axis.

37. The blood pump and estimation and control system of claim 36 wherein the thrust forces are generated by blades of the impeller.

38. The blood pump and estimation and control system of claim 37 wherein the thrust forces are generated by forces of the blades of the impeller.

39. The blood pump and estimation and control system of claim 38 wherein the blades are tapered or non-planar, so that a thrust is created between the edges and the pump housing during relative movement therebetween.

40. The blood pump and estimation and control system of claim 37 wherein the blades are shaped such that the gap at the leading edge of the blade is greater than at the trailing edge and thus the fluid which is drawn through the gap experiences a wedge shaped restriction which generates a thrust.

41. The blood pump and estimation and control system of claim 36 wherein the pump is of centrifugal type or mixed flow type with blades of the impeller open on both front and back faces of the pump housing.

42. The blood pump and estimation and control system of claim 41 wherein the front face of the pump housing is made conical, in order that the thrust force perpendicular to the conical surface has a radial component, which provides a radial restoring force to a radial displacement of the impeller axis during use.

43. The blood pump and estimation and control system of claim 37 wherein the driving torque of the impeller derives from the magnetic interaction between permanent magnets within the blades of the impeller and oscillating currents in windings encapsulated in the pump housing.

44. The rotary blood pump and estimation and control system of claim 36 wherein the pump is of axial type.

45. The rotary blood pump and estimation and control system of claim 44 wherein, within a uniform cylindrical section of the pump housing, the impeller includes tapered blade bearing surfaces which form a radial hydrodynamic bearing.

46. The rotary blood pump and estimation and control system of claim 45 wherein an interior of the pump housing is made with reducing radius at the two ends, and wherein the end hydrodynamic thrust forces have an axial component which can provide the axial bearing.

47. The rotary blood pump and estimation and control system of claim 45 wherein magnetic forces provide the axial bearing.

48. The rotary blood pump and estimation and control system of claim 36, further comprising a housing within which the impeller acts by rotation about an impeller axis to cause a pressure differential between an inlet side of the pump housing of the pump and an outlet side of the pump housing of the pump, wherein the impeller is suspended hydrodynamically by thrust forces generated by the impeller during movement in use of the impeller.

49. The rotary blood pump and estimation and control system of claim 48 wherein the impeller includes magnetic material therein, the magnetic material encapsulated within a biocompatible shell or coating.

50. The rotary blood pump and estimation and control system of claim 49 wherein the biocompatible shell or coating comprises of a material which can be applied at low temperature.

51. The rotary blood pump and estimation and control system of claim 48 wherein internal walls of the pump which can come into contact with blades of the impeller during use are coated with a hard material.

52. The rotary blood pump and estimation and control system of claim 36, wherein the pump is a seal-less and shaft-less pump and wherein the housing defines a chamber therein and has a liquid inlet to the chamber and a liquid outlet from the chamber; the impeller being located within the chamber; the arrangement between the impeller, the inlet, the outlet and the internal walls of the chamber being such that upon rotation of the impeller about an impeller axis relative to the housing, liquid is urged from the inlet through the chamber to the outlet; and wherein thrust forces are generated by relative movement of the impeller with respect to the housing.

53. The pump of claim 52 wherein the thrust forces are generated by blades of the impeller.

54. The pump of claim 53 wherein the thrust forces are generated by surfaces of the blades of the impeller.

55. The pump of claim 54 wherein the surfaces of the blades are tapered or non-planar.

56. The pump of claim 52 wherein the surfaces of the blades are shaped such that a gap at the leading edge of each of the blades is greater than at a trailing edge thereof whereby fluid which is drawn through the gap experiences a wedge shaped restriction which generates a thrust relative to the housing.

57. The pump of claim 53 wherein the pump is of centrifugal type or mixed flow type with the blades of the impeller open on both front and back faces of the pump housing.

58. The pump of claim 57 wherein the front face of the pump housing is made conical, in order that the thrust perpendicular to its conical surface at any point has a radial component, which provides a radial restoring force to a radial displacement of the impeller axis.

59. The pump of claim 57 wherein the driving torque of the impeller derives from magnetic interaction between permanent magnets within the blades of the impeller and oscillating currents in windings encapsulated in the pump housing.

60. The pump of claim 52 wherein the pump is of axial type.

61. The pump of claim 60 wherein, within a uniform cylindrical section of the pump housing, tapered blade surfaces form a radial hydrodynamic bearing.

62. The pump of claim 60 wherein the pump housing is made with reducing radius at opposed ends, and wherein the end hydrodynamic thrust forces have an axial component which can provide the axial bearing.

63. The pump of claim 60 wherein magnetic forces provide the axial bearing.

64. The rotary blood pump and estimation and control system of claim 48, wherein the impeller is suspended hydrodynamically in at least one of a radial or axial direction by thrust forces generated by the impeller during movement in use of the impeller.

65. The pump of claim 64 wherein the impeller includes magnetic material therein, the magnetic material encapsulated within a biocompatible shell or coating.

66. The pump of claim 65 wherein the biocompatible shell or coating comprises a diamond coating.

67. The pump of claim 65 wherein internal walls of the pump which can come into contact with the impeller during use are coated with a hard material.

68. The pump of claim 64 wherein at least upper and lower surfaces of blades of the impeller are interconnected by a structure having deformities in the outer surfaces thereof so that a thrust is created between the surfaces and the adjacent pump casing during relative movement therebetween.

69. An estimation and control system for a pump; the pump of the type having an impeller located within a pump cavity in a pump housing; the housing having a fluid inlet in fluid communication with the cavity; the housing having a fluid outlet in fluid communication with the pump cavity; the impeller urged to rotate about an impeller axis so as to cause fluid to be urged from the inlet through the pump cavity to the pump outlet; the impeller urged to rotate by an impeller drive; impeller supported for rotational movement by an impeller support; the pump maintained at or near a predetermined operating point by a controller acting on the impeller drive; the controller receiving as input variables at least a first input variable derived from the impeller drive; the controller receiving at least a second input variable also derived from the impeller drive; the controller thereby calculating an estimate of the operating point to an approximation of predetermined accuracy relying on signals available from the impeller drive; the controller controlling the pump by comparing the predetermined operating point with the estimate of the operating point; and wherein instantaneous pump speed and electrical input power are allowed to be modulated by a heart, in use, by appropriate selection of a control time constant to reduce over and under pumping.

70. The system of claim 69 in combination with the pump.

71. The system of claim 69 wherein the control time constant of the control system is greater than the rotational, inertial time constant of the impeller.

72. The system of claim 69 wherein the control time constant is at least one cardiac cycle.

73. The system of claim 69 wherein the first input variable comprises instantaneous pump speed.

74. The system of claim 69 wherein the second input variable is representative of electrical input power to the impeller drive.

75. The system of claim 69 wherein the pump is arranged to operate according to a relatively flat pressure versus flow rate characteristic.

76. The system of claim 69 wherein variation in speed of the impeller, in use, is permitted and then utilized to calculate an improved estimate of pressure rise across the pump and flow through it.

77. The system of claim 75 wherein the pressure versus flow rate characteristic is sufficiently flat that the pressure will remain constant to a sufficient approximation over a predetermined operating range whereby, over the operating range, the system can assume that pump speed will be proportional to flow rate.

78. The system of claim 62 wherein the predetermined operating point is calculated so as to maintain minimum pump speed such that the minimum head pressure across the pump does not increase.

79. The system of claim 78 wherein the system ensures that minimum pump speed is always at least the minimum speed at which non-regurgitant flow will occur.

80. The system of claim 79 wherein the speed at which regurgitant or negative flow will begin to occur is determined as that pump set point speed where levels and phase lags between pump outlet and inlet pressures fall during diastole cause flow reversal.

81. The system of claim 80 wherein the pump speed at which regurgitation is calculated to occur is calculated according to:

$$Nregurg=N(t) \text{ for } Qdiastole=0L/min.$$

82. A physiological controller for use in association with a pump; the controller monitoring estimated flow of fluid within the pump and pressure across the pump by non-contact means thereby to control speed of rotation of an impeller within the pump; and wherein the controller permits impeller speed to vary under a pulsating fluid load thereby to assist in calculation and adjustment of impeller speed set point.

83. The controller of claim 82 wherein the fluid is blood; the controller including a processor which determines optimal pump output for the pump to meet demand for blood at all physiological states of a mammal in which the pump is installed.

84. The controller of claim 83 wherein the processor includes as a control aim to adjust pump output so as to eliminate suction collapse of blood vessels.

85. The controller of claim 84 wherein the processor calculates flow and head to discern optimal pumping based on collapse and overpumping.

86. The controller of claim 84 wherein the processor calculates values of speed and power (peak and RMS values) to discern optimal pumping based on collapse and overpumping.

87. The controller of claim 84 wherein the processor includes a control aim which adjusts optimal pump output to a point close to where the aortic valve just opens or just fails to open.

88. The controller of claim 87 wherein the pump comprises a ventricular assist device adapted to assist operation of a ventricle of a heart and wherein the processor adjusts pump output so that, in alternating fashion, the ventricle in conjunction with the aortic valve is allowed to eject blood over a predetermined number of cardiac cycles and then the ventricle in conjunction with the aortic valve is caused to not eject blood over a following predetermined number of cardiac cycles.

* * * * *

UNITED STATES PATENT AND TRADEMARK OFFICE
CERTIFICATE OF CORRECTION

PATENT NO. : 6,866,625 B1
DATED : March 15, 2005
INVENTOR(S) : Ayre et al.

It is certified that error appears in the above-identified patent and that said Letters Patent is hereby corrected as shown below:

Title page,
Item [75], Inventors, delete "Neutral Bay" and insert -- Crows Nest --.
Item [56], References Cited, U.S. PATENT DOCUMENTS, "5,326,344 A" reference, delete "623/314" and insert -- 623/3.14 --.

Column 30,
Line 62, delete "deformation" and insert -- deformations --.

Column 35,
Line 44, after "diastole" insert -- so as to --.

Signed and Sealed this

Twentieth Day of September, 2005

JON W. DUDAS
*Director of the United States Patent and Trademark Office*